United States Patent
Kay et al.

(10) Patent No.: US 8,629,269 B2
(45) Date of Patent: Jan. 14, 2014

(54) DYE FOR A DYE-SENSITISED SOLAR CELL, AND A SOLAR CELL COMPRISING THE SAME

(75) Inventors: Kwang-Yol Kay, Suwon-si (KR); Kang-Jin Kim, Seoul (KR); Jong-Hyung Kim, Incheon (KR); Young-Jin Kwon, Seoul (KR)

(73) Assignee: Solarsys Co., Ltd., Gyeonggi-do (KR)

( * ) Notice: Subject to any disclaimer, the term of this patent is extended or adjusted under 35 U.S.C. 154(b) by 239 days.

(21) Appl. No.: 12/866,347

(22) PCT Filed: Feb. 5, 2009

(86) PCT No.: PCT/KR2009/000561
§ 371 (c)(1), (2), (4) Date: Aug. 5, 2010

(87) PCT Pub. No.: WO2009/099302
PCT Pub. Date: Aug. 13, 2009

(65) Prior Publication Data
US 2011/0028716 A1    Feb. 3, 2011

(30) Foreign Application Priority Data

Feb. 5, 2008 (KR) .................. 10-2008-0011757
Feb. 13, 2008 (KR) .................. 10-2008-0012929
Apr. 16, 2008 (KR) .................. 10-2008-0035194
Feb. 3, 2009 (KR) .................. 10-2009-0008472

(51) Int. Cl.
*C07D 487/22* (2006.01)
*C07D 279/18* (2006.01)

(52) U.S. Cl.
USPC ............................. 540/145; 544/35

(58) Field of Classification Search
USPC ............................. 540/145; 544/35
See application file for complete search history.

(56) References Cited

U.S. PATENT DOCUMENTS

| 4,526,705 A | 7/1985 | Arndt et al. |
| 6,084,176 A | 7/2000 | Shiratsuchi et al. |
| 2007/0191600 A1 | 8/2007 | Yu et al. |

FOREIGN PATENT DOCUMENTS

JP     2008021496    1/2008

*Primary Examiner* — Brian McDowell
(74) *Attorney, Agent, or Firm* — The Webb Law Firm

(57) ABSTRACT

The present invention relates to a dye for a dye-sensitized solar cell. The dye according to the present invention has a high degree of light absorbency and can improve the photoelectric current conversion efficiency when employed in a light-absorbing layer for a solar cell. Chemical Formula 1 illustrates the present invention.

[Chemical Formula 1]

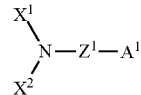

wherein $X^1$, $X^2$, N, $Z^1$, and $A^1$ are described herein.

3 Claims, 10 Drawing Sheets

DYE FOR A DYE-SENSITISED SOLAR CELL, AND A SOLAR CELL COMPRISING THE SAME

TECHNICAL FIELD

The present invention relates to a dye for use in a dye-sensitised solar cell and a dye-sensitised solar cell using the same, and in particular, to a novel dye having high light absorbance and capable of being applied to a light-absorbing layer of a solar cell to improve the photoelectric current conversion efficiency and to increase the open circuit voltage.

BACKGROUND

Recently, active studies have been conducted to develop a substitute for the existing fossil fuels in order to reduce emission of carbon dioxide regarded as a main cause of global warming and to solve the energy-related problems at hand. Intensive studies about the use of natural energy sources, such as wind, atomic force and solar light, have been made to allow those energy sources to substitute for petroleum sources that may be exhausted in the near future. Among those energy sources, solar cells using solar energy are the most eco-friendly and are inexhaustible, unlike the other energy sources, with the proviso that adequate methods of utilizing solar energy are developed. Since solar cells using selenium (Se) were developed in 1983, silicon solar cells have been spotlighted more recently. However, silicon solar cells require high manufacturing cost and thus are not commercially practical, and are insufficient in terms of cell efficiency. To overcome such problems, many workers have studied intensively to develop economical dye-sensitised solar cells.

While organic light emitting displays (OLEDs) use electric energy as their driving mechanism, dye-sensitised solar cells are based on the mechanism in which they absorb light energy in the visible range to produce electron-hole pairs. In addition, dye-sensitised solar cells are photoelectrochemical solar cells including photosensitive dye molecules and transition metal oxides transporting the resultant electrons as their main constitutional elements. Typical examples of such dye-sensitised solar cells include those using titanium dioxide nanoparticles, which are developed in 1991 by Michael Graetzel and coworkers of Ecole Polytechnique Federale de Lausanne (EPFL).

The above dye-sensitised solar cells developed by Michael Graetzel and coworkers are advantageous in that they may be applied to outer wall windows of buildings and glass greenhouses due to their transparent electrodes and they are cost-efficient as compared to the existing silicon solar cells. However, such solar cells have low photoelectric current conversion efficiency, and thus may not be commercially practical.

Photoelectric current conversion efficiency is in proportion to the amount of electrons generated by the absorption of solar light. In order to increase the efficiency of a solar cell, electron generation may be increased by increasing solar light absorption or the amount of dye adsorption, or by preventing loss of the excited electrons caused by electron-hole recombination. It is possible to increase the reflectivity of a platinum electrode in order to increase solar light absorbance. It is also possible to provide oxide semiconductor particles with a nano-scaled size in order to increase the dye adsorption per unit area. Addition of a semiconductor oxide light scattering agent having a size of several micrometers is also known in the art.

However, improvement in photoelectric current conversion efficiency is still limited in the above-mentioned methods. Therefore, there is an imminent need for developing novel technologies to improve photoelectric current conversion efficiency, in particular, for developing a novel dye having high light absorbance as well as a broad range of light absorption to improve photoelectric current conversion efficiency.

DETAILED DESCRIPTION

Technical Problems

An embodiment of the present invention is directed to providing a dye for a dye-sensitised solar cell having high light absorbance. Another embodiment of the present invention is directed to providing a dye-sensitised solar cell including the above dye to improve photoelectric current conversion efficiency.

Technical Solutions

In one general aspect, there are provided a compound having a structure represented by Chemical Formula 1 or 2, and a dye for a dye-sensitised solar cell including the same:

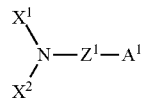

[Chemical Formula 1]

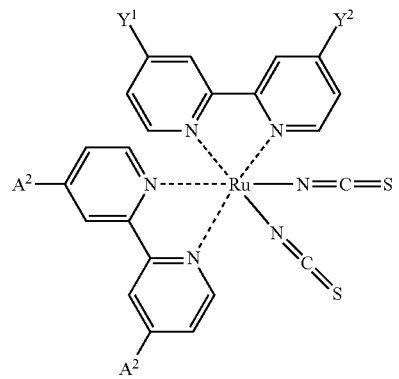

[Chemical Formula 2]

wherein $X^1$ and $X^2$ independently represent (C6-C60)aryl, (C3-C60)heteroaryl or a combination thereof, with the proviso that at least one of $X^1$ and $X^2$ includes porphyrinyl, phenothiazinyl, coumarinyl or phthalocyanyl;

$Y^1$ and $Y^2$ are independently selected from (C6-C60)aromatic hydrocarbyl, (C3-C60)aromatic heterocyclic group or a combination thereof and

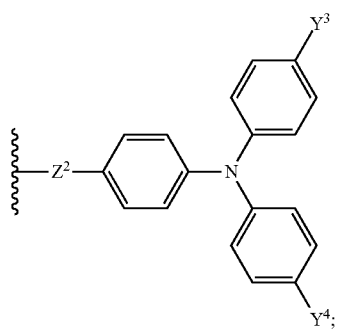

$Y^3$ and $Y^4$ independently represent (C6-C60)aryl, (C3-C60)heteroaryl or a combination thereof, with the proviso that at least one of $Y^1$ to $Y^4$ includes porphyrinyl, phenothiazinyl, coumarinyl or phthalocyanyl;

$Z^1$ and $Z^2$ are independently selected from a chemical bond, (C6-C30)arylene, one or more (C3-C30)heteroarylene, one or more vinylene and a combination thereof;

$A^1$ and $A^2$ represent an acidic group; and the aryl, heteroaryl, arylene, heteroaryl or vinylene may be further substituted with one or more substituent(s) selected from (C1-C20)alkyl, (C1-C20)alkoxy, halogen atoms, amino, nitro and cyano (CN).

Other features and aspects will be apparent from the following detailed description.

When a dye-sensitised solar cell is driven, photogenerated charges are produced first from light energy. In general, a dye material is used to produce the photogenerated charges and the dye material is excited by absorbing the light transmitted through a transparent conductive substrate.

As the dye material, metal complexes have been used widely. Among such metal complexes, mono-, bis- or tris-(substituted 2,2'-bipyridine) complex salts of ruthenium, etc. are used in general. Particularly, such metal complex salts use both the absorption of the ligands thereof and the absorption caused by the metal to ligand charge transfer (MLCT), and thus have relatively high efficiency. However, their efficiency is still insufficient, because the electrons excited by light from the ground state of the metal complexes drop back to the ground state relatively at a high rate. To solve such problems, methods of introducing various electron transfer materials into the metal complexes through covalent bonding have been reported. However, introduction of electron transfer materials through covalent bonding is complicated and sophisticated. Thus, it is difficult to introduce various electron transfer materials. In addition, a broader range of light absorption and higher light absorbance are advisable to improve the efficiency of a solar cell. However, the ruthenium complexes are problematic in that they have low light absorbance.

The dye for a solar cell according to the present invention is a compound or ruthenium complex having an aniline structure to which porphyrinyl, phenothiazinyl, coumarinyl or phthalocyanyl group is introduced so that it has high light absorbance. Thus, it is expected that the dye improves the photoelectric current conversion efficiency when used in a dye-sensitised solar cell.

The dye for a dye-sensitised solar cell according to the present invention is selected from the compounds represented by Chemical Formulas 1 and 2.

In Chemical Formulas 1 and 2, the aryl is an aromatic hydrocarbyl group and is selected from the group consisting of phenyl, naphthyl, anthracenyl, fluorenyl, biphenyl and a combination thereof, and preferably, a C6-C30 carbocyclic aromatic compound. The heteroaryl is an aromatic heterocyclic group and forms an aromatic ring with a hetero atom, such as nitrogen (N), sulfur (S), oxygen (O), etc., contained therein. The heteroaryl is preferably selected from the group consisting of pyrane, pyrrole, thiophene, carbazole and a combination thereof.

In addition, $Z^1$ and $Z^2$ independently represent a chemical bond or take the form of a radical, both ends of which are capable of forming a bond, and are selected from the group consisting of arylene, heteroarylene, vinylene and a combination thereof. More particularly, $Z^1$ and $Z^2$ are independently selected from the group consisting of vinylene, polyvinylene, phenylene, naphthylene, anthracenylene, fluorenylene, biphenylnene, pyranylene, pyrrolene, thiophenylene, carbazolylene and a combination thereof $A^1$ and $A^2$ independently represent an acidic group, and are preferably selected from the group consisting of carboxyl, phosphite, sulfonate, phosphinate, hydroxyl, oxycarboxylate, acid amide and a combination thereof, more preferably, carboxyl.

Further, the dye includes at least one functional group selected from porphyrinyl, phenothiazinyl, coumarinyl and phthalocyanyl. More preferably, two or more functional groups selected from porphyrinyl, phenothiazinyl, coumarinyl and phthalocyanyl are present in one compound.

More particularly, the compound represented by Chemical Formula 1 is selected from the compounds represented by Chemical Formula 3, and the compound represented by Chemical Formula 2 is selected from the compounds represented by Chemicals Formula 4 and 5:

[Chemical Formula 3]

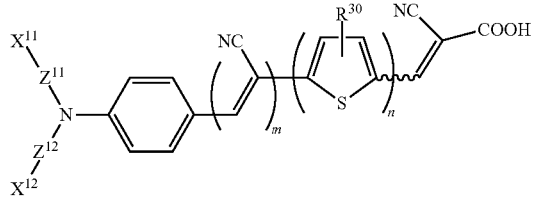

-continued
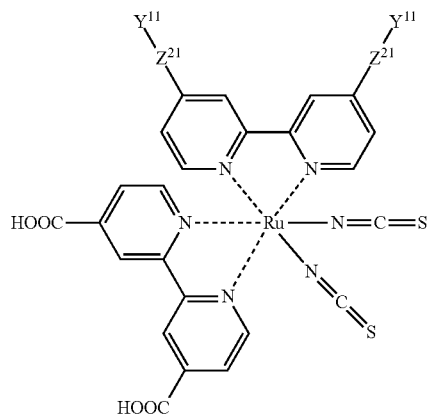
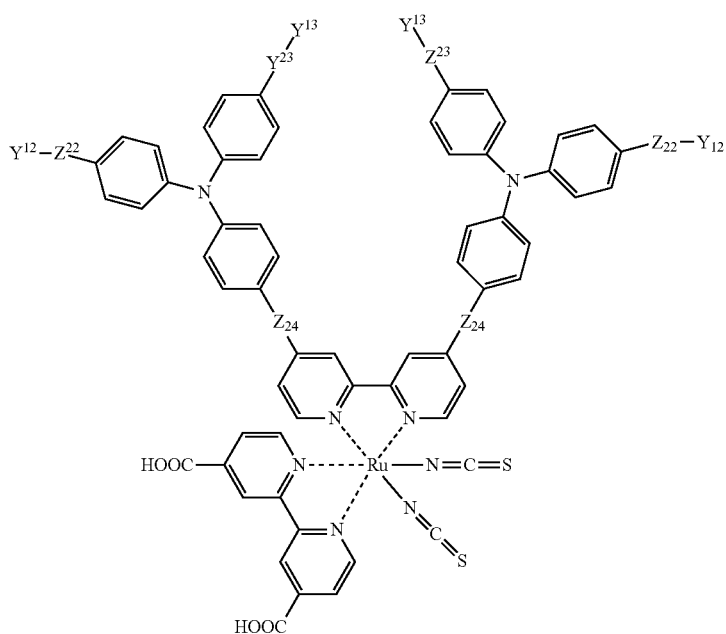
wherein
$X^{11}$ and $Y^{11}$ through $Y^{13}$ are independently selected from the following structures:
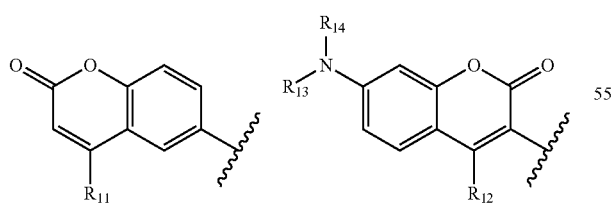
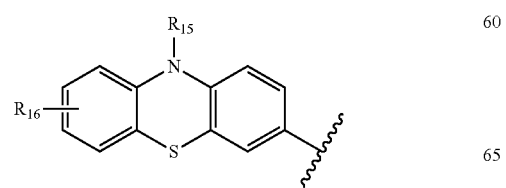
[Chemical Formula 4]
[Chemical Formula 5]
-continued
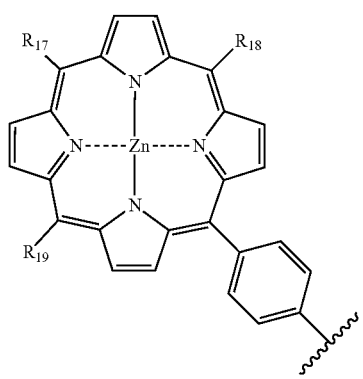

-continued

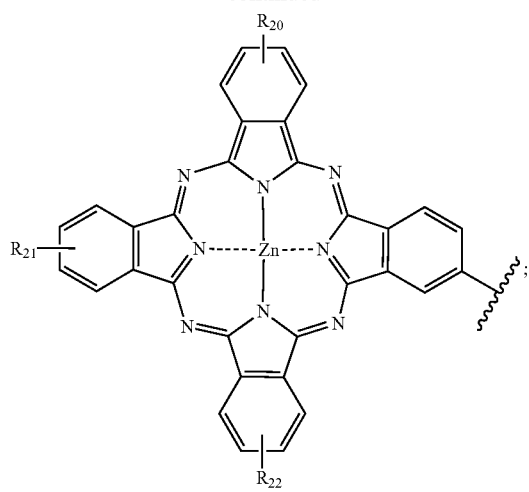

$X^{12}$ is selected from the following structures:

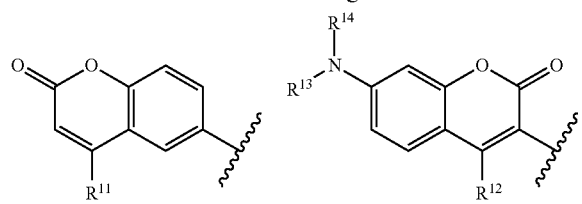

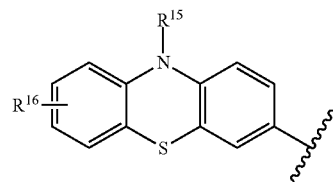

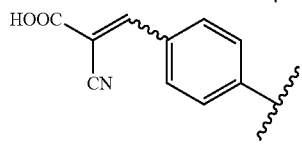

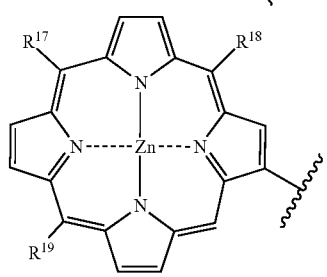

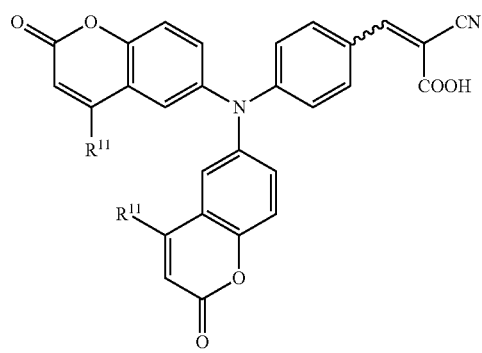

-continued

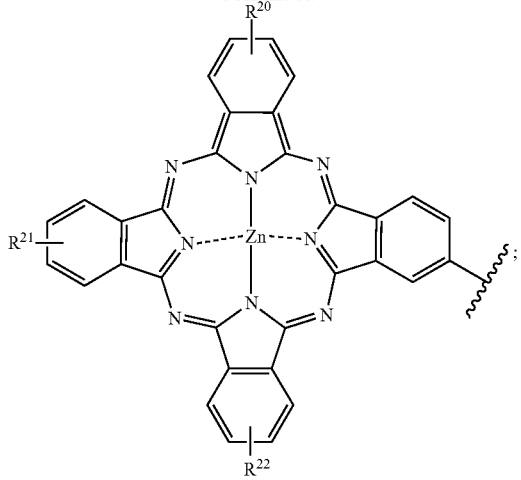

$Z^{11}$ and $Z^{12}$ independently represent

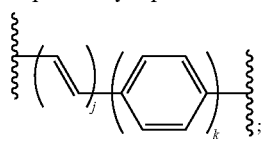

$Z^{21}$ through $Z^{24}$ independently represent

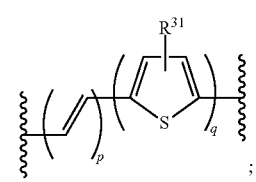

m is an integer from 0 to 2, and n is an integer from 0 to 4;
s an integer from 0 to 2, and k is an integer from 0 to 4;
p is an integer from 0 to 2, and q is an integer from 0 to 4; and $R^{11}$ through $R^{22}$, $R^{30}$ and $R^{31}$ independently represent hydrogen, or are independently selected from (C1-C20)alkyl, (C1-C20)alkoxy, halogen atoms, amino, nitro and cyano (CN).

More particularly, the compounds represented by Chemical Formulas 3 to 5 are selected from the compounds of the following list, wherein $R^{11}$ through $R^{22}$, $R^{31}$, $R^{32}$ and $R^{40}$ are independently selected from hydrogen and (C1-C20)alkyl, n is an integer from 0 to 4, a is an integer 0 or 1, b is an integer from 0 to 2, c is an integer 0 or 1, and d is an integer from 0 to 2:

-continued
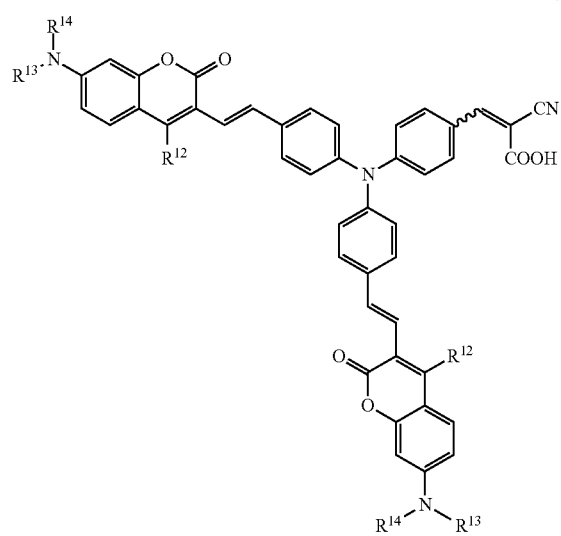
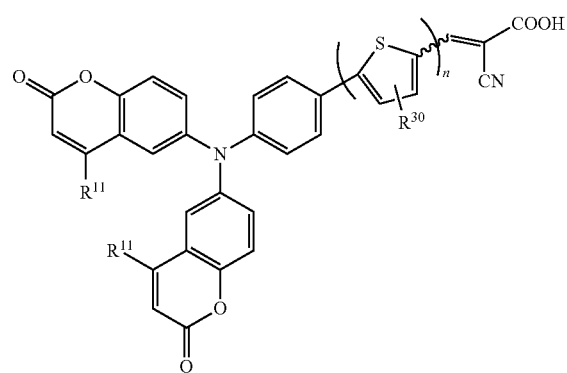
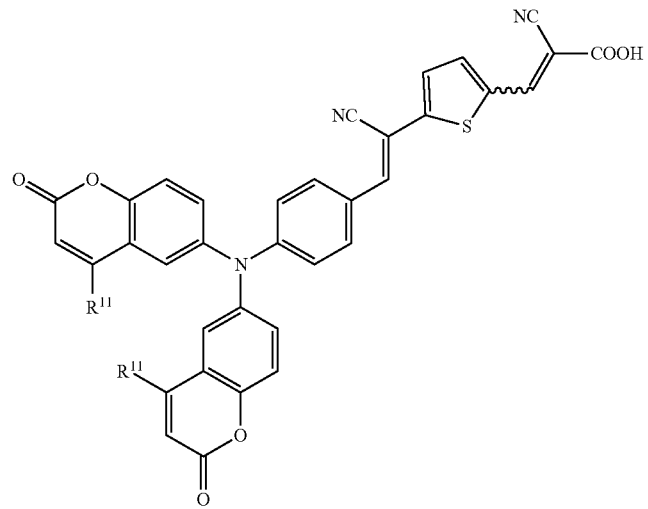

-continued
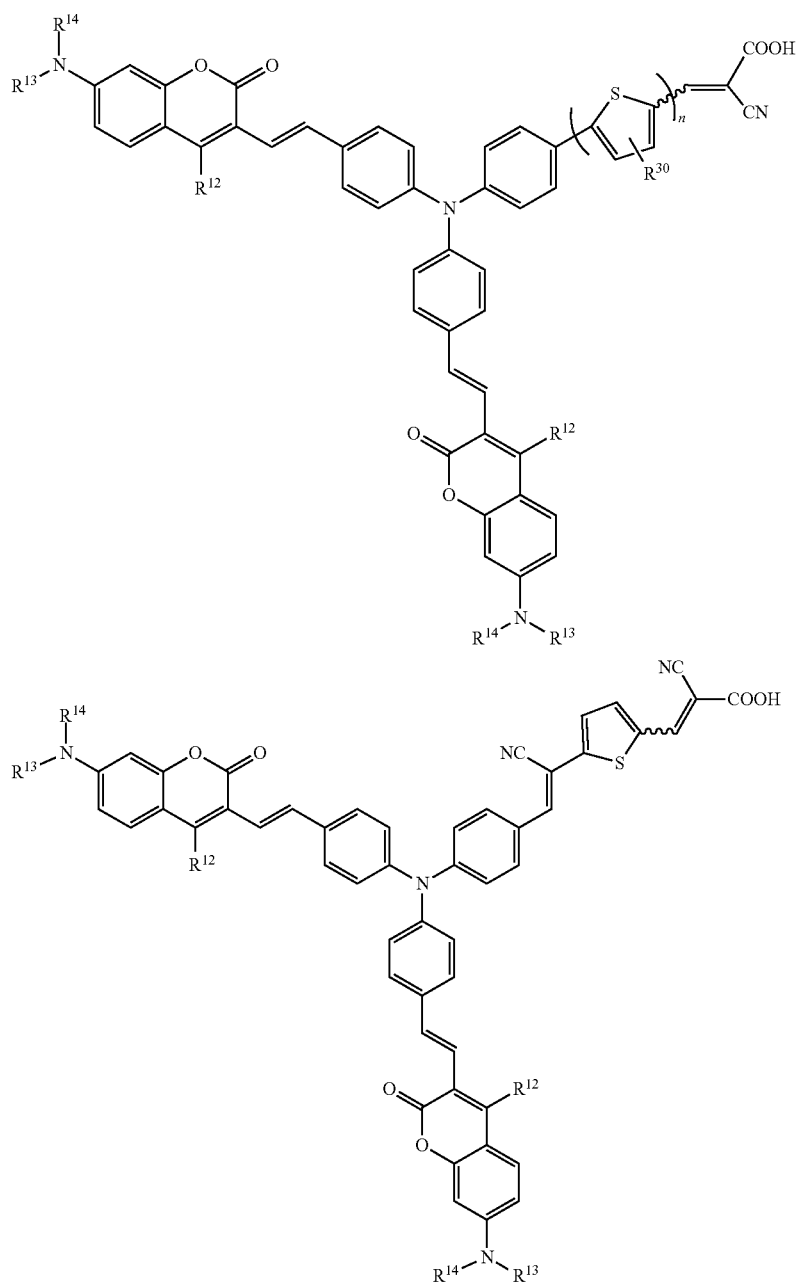
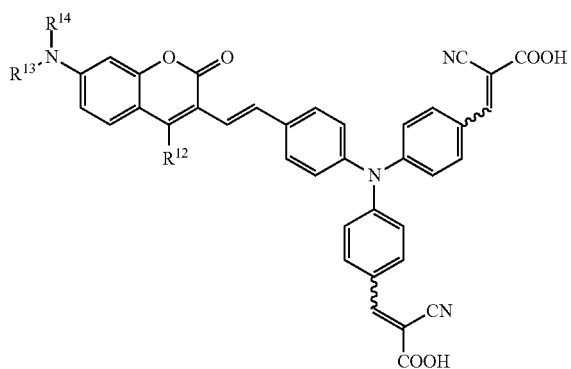

-continued
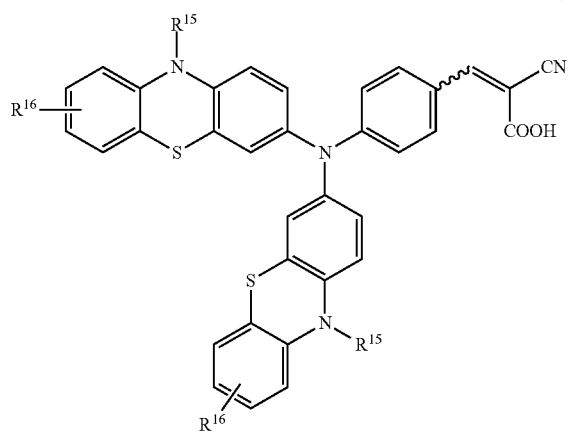
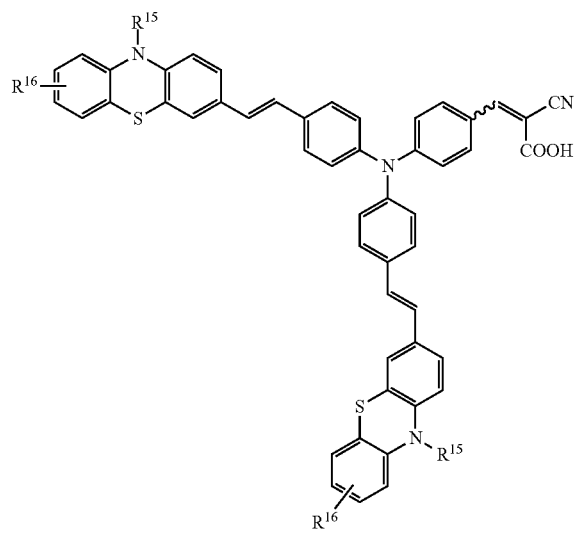
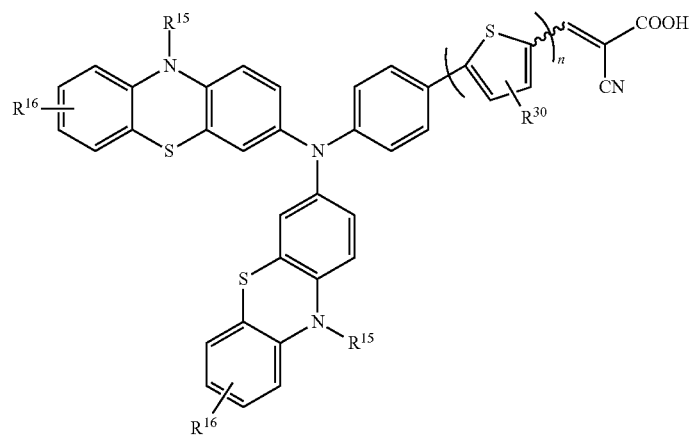

-continued
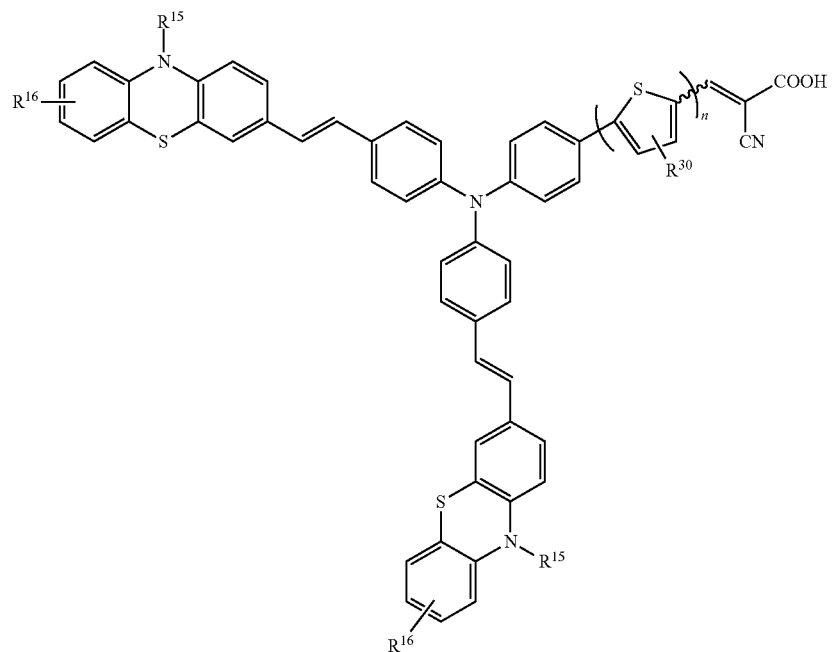
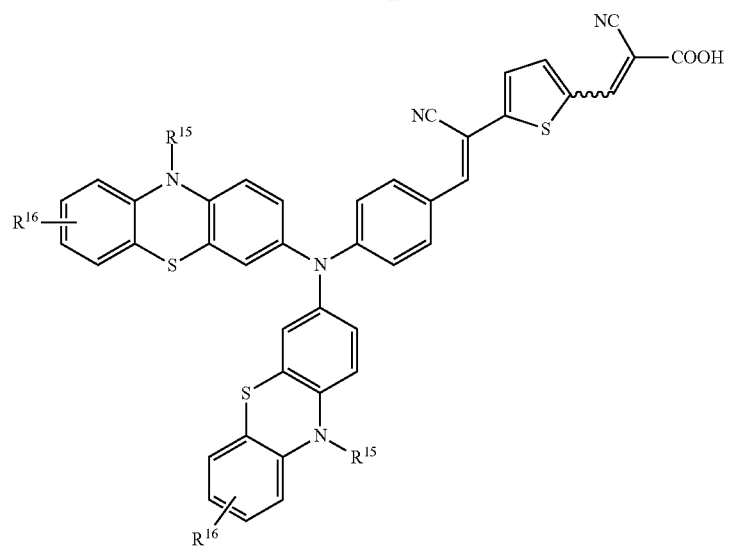
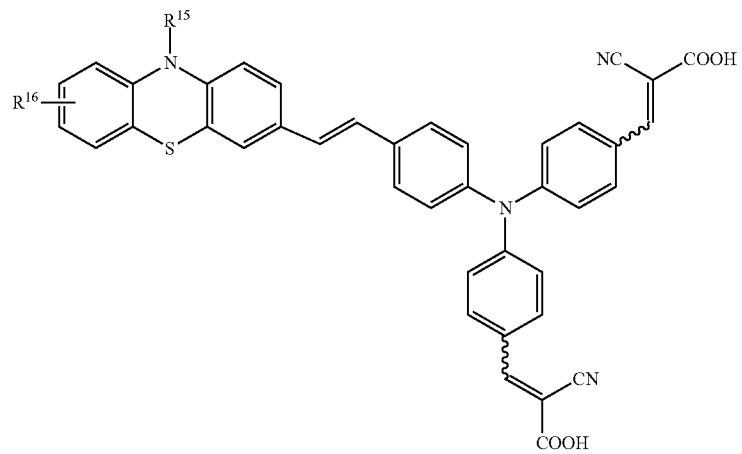

-continued
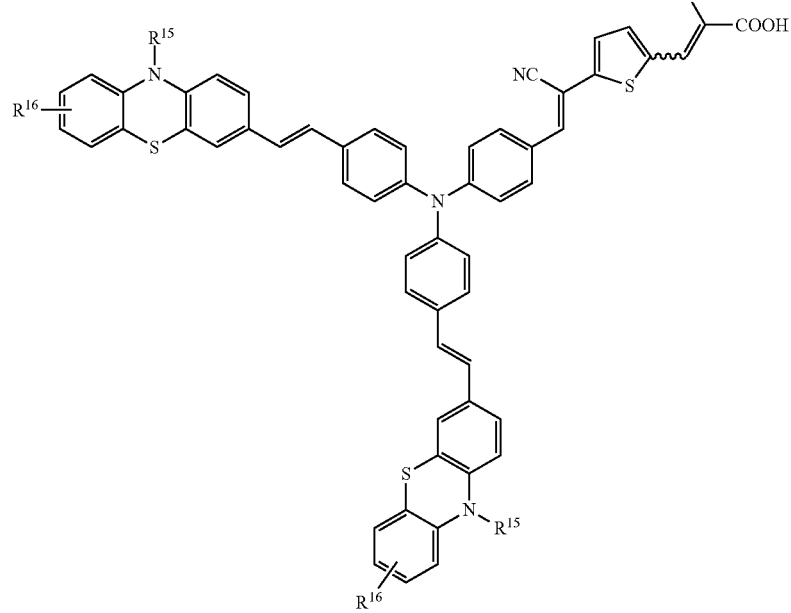
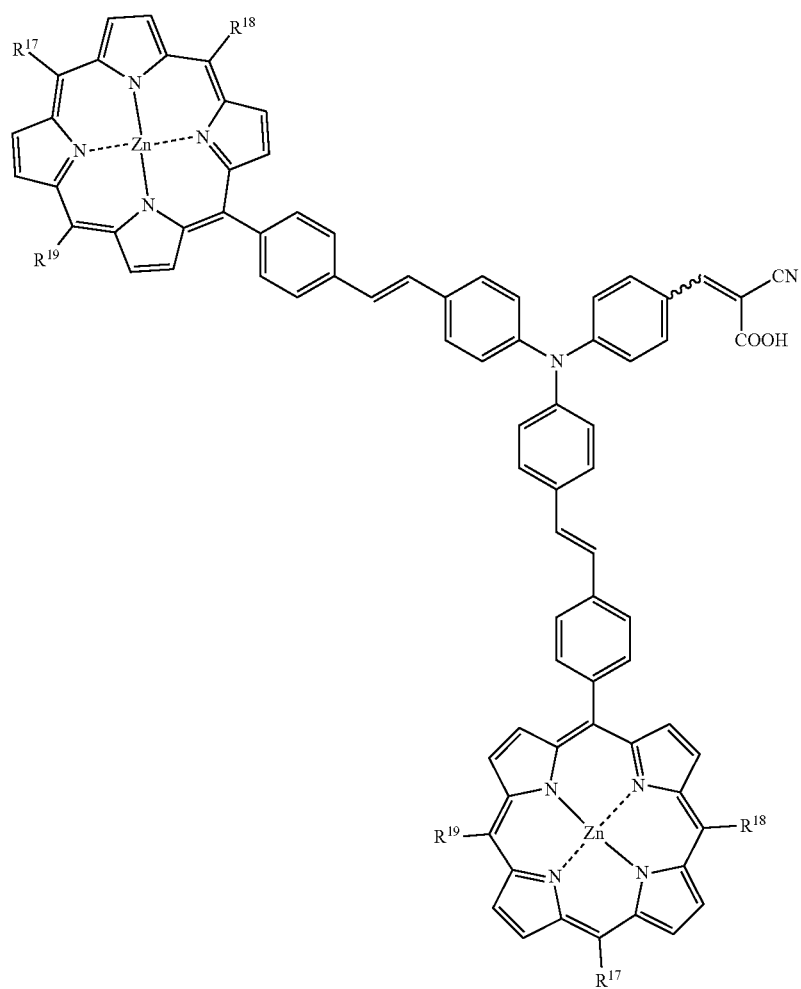

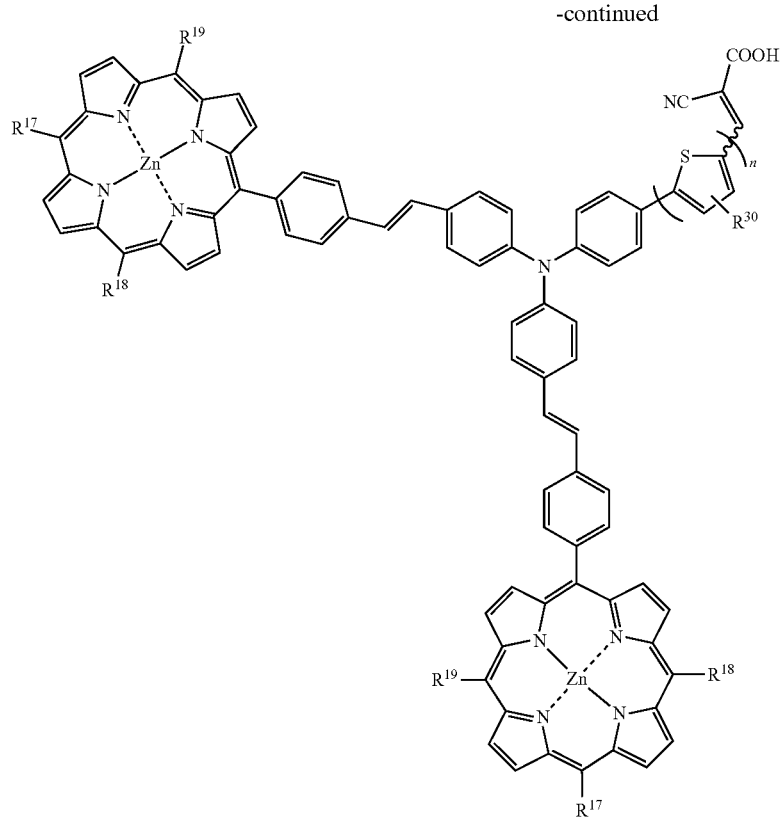
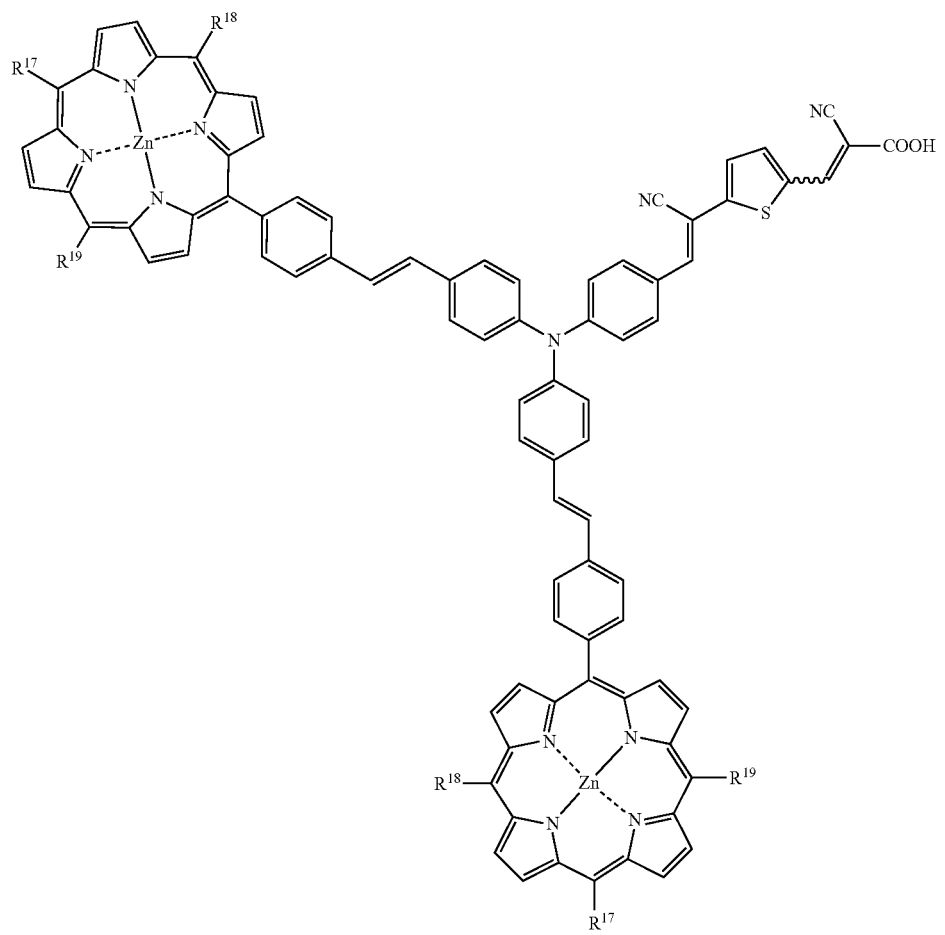

-continued
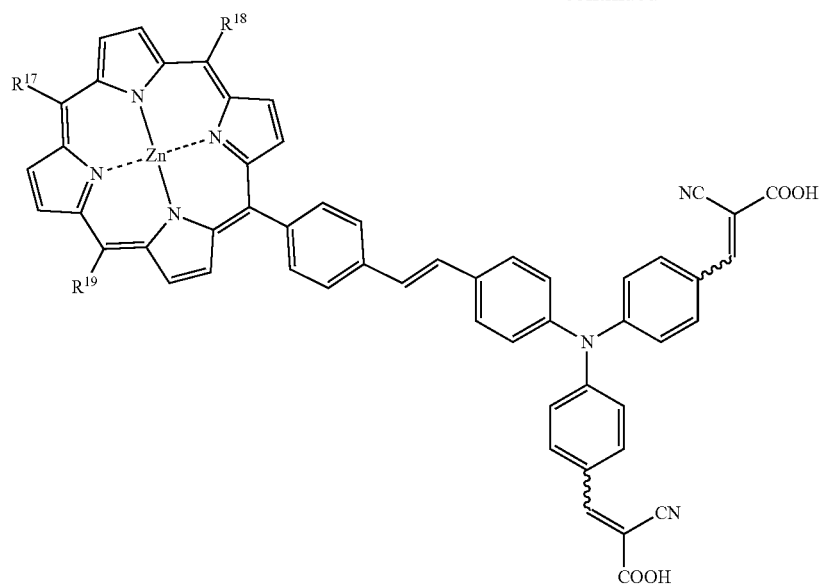
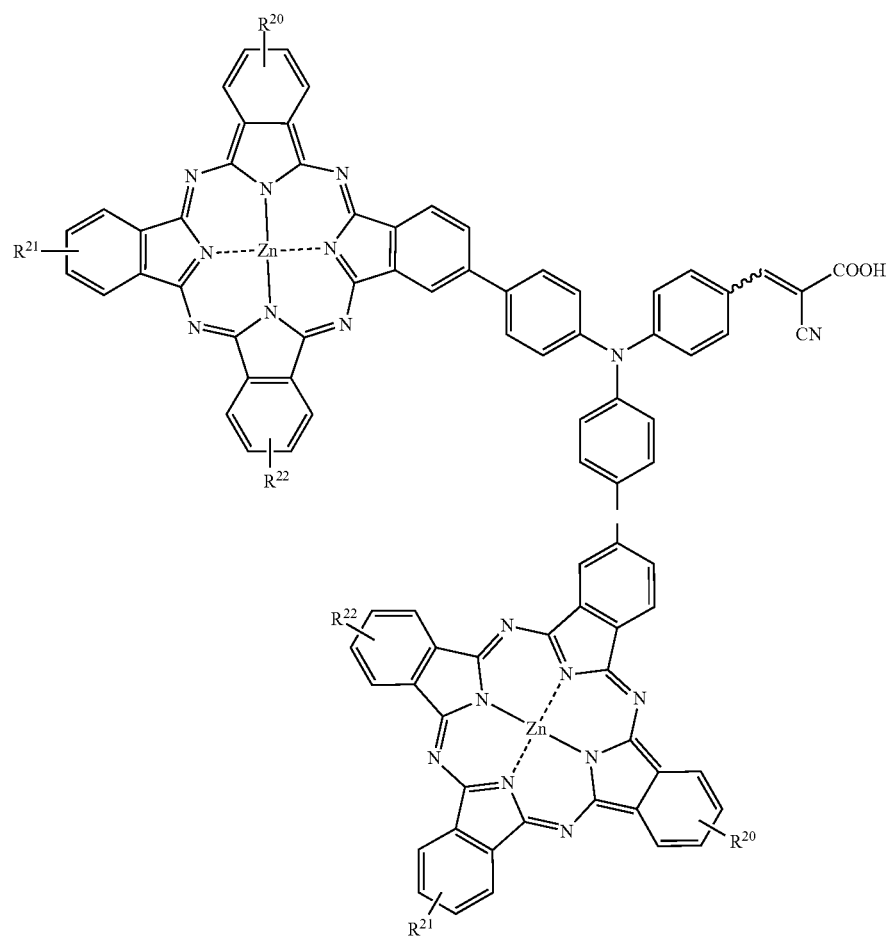

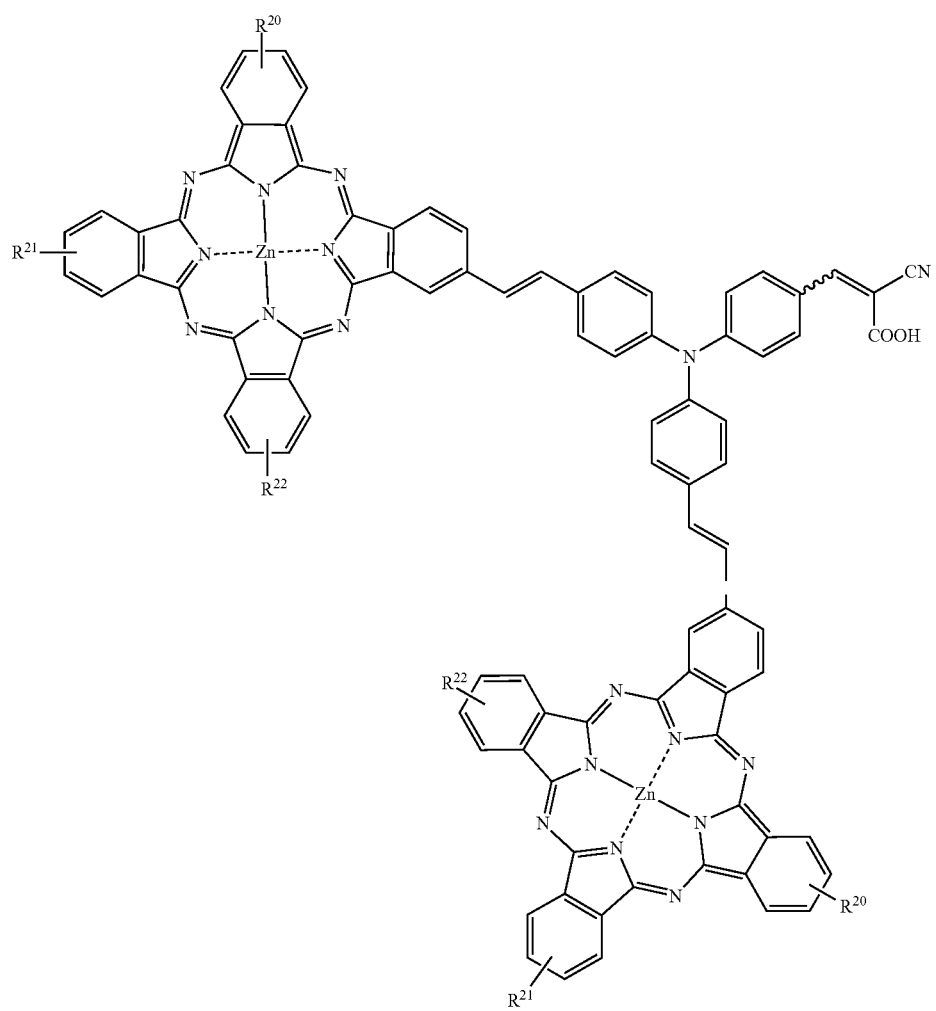
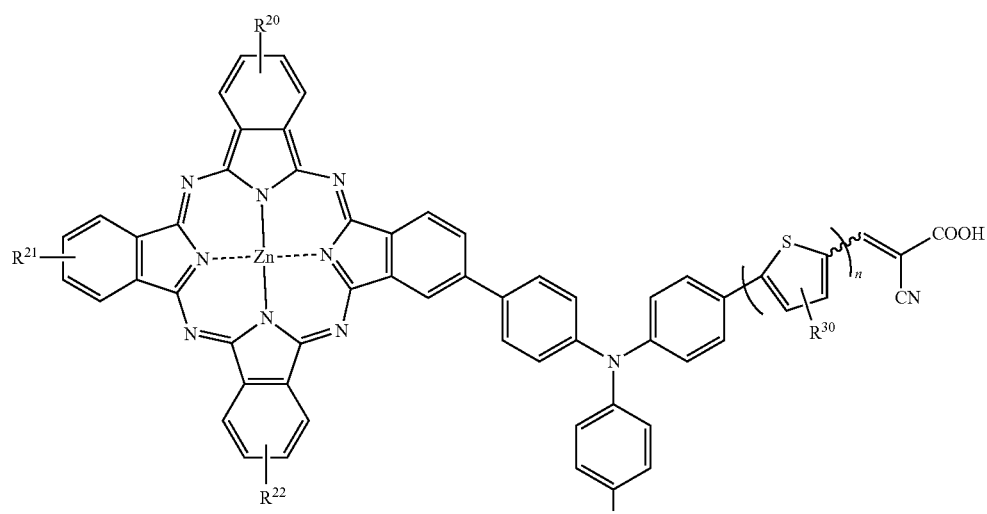

-continued
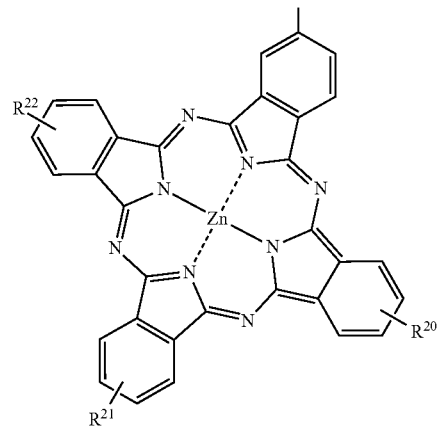
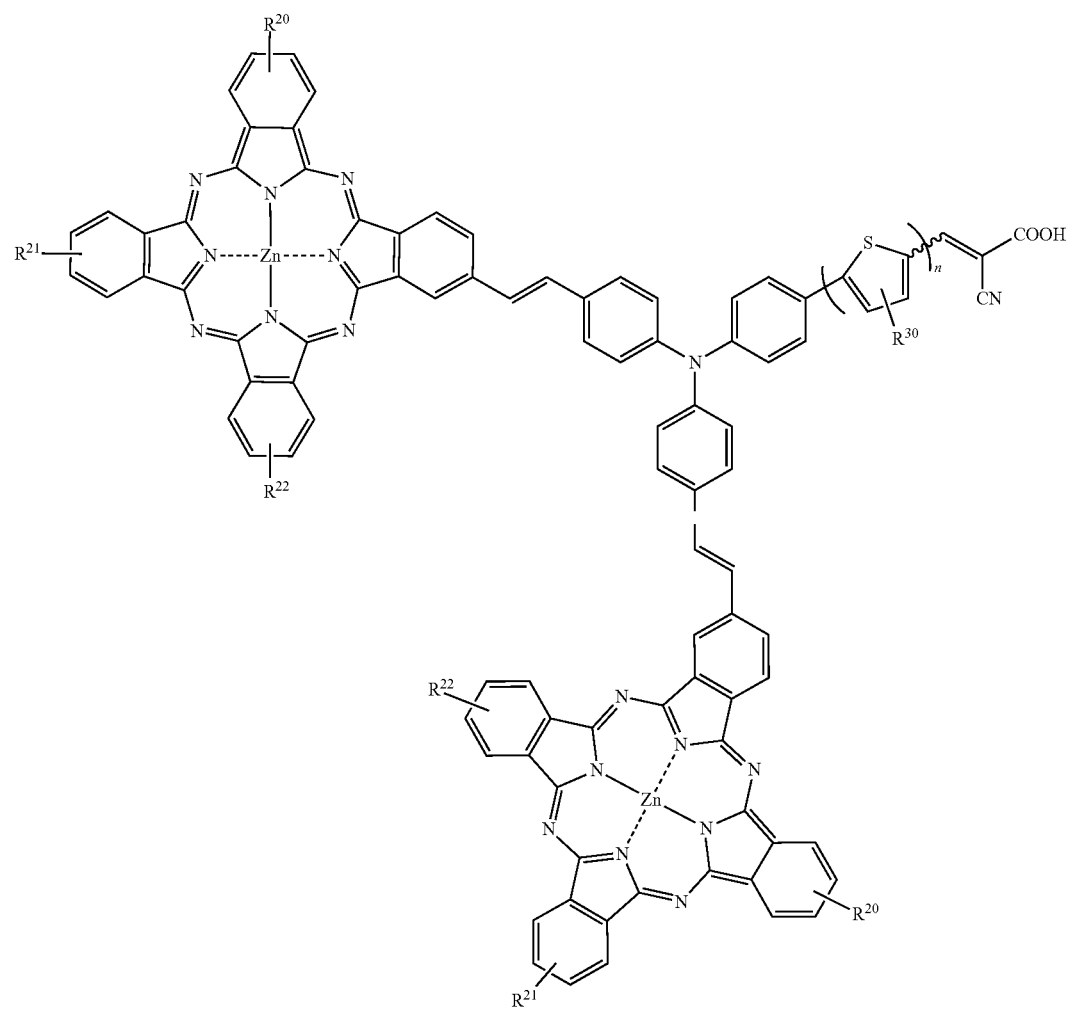

-continued
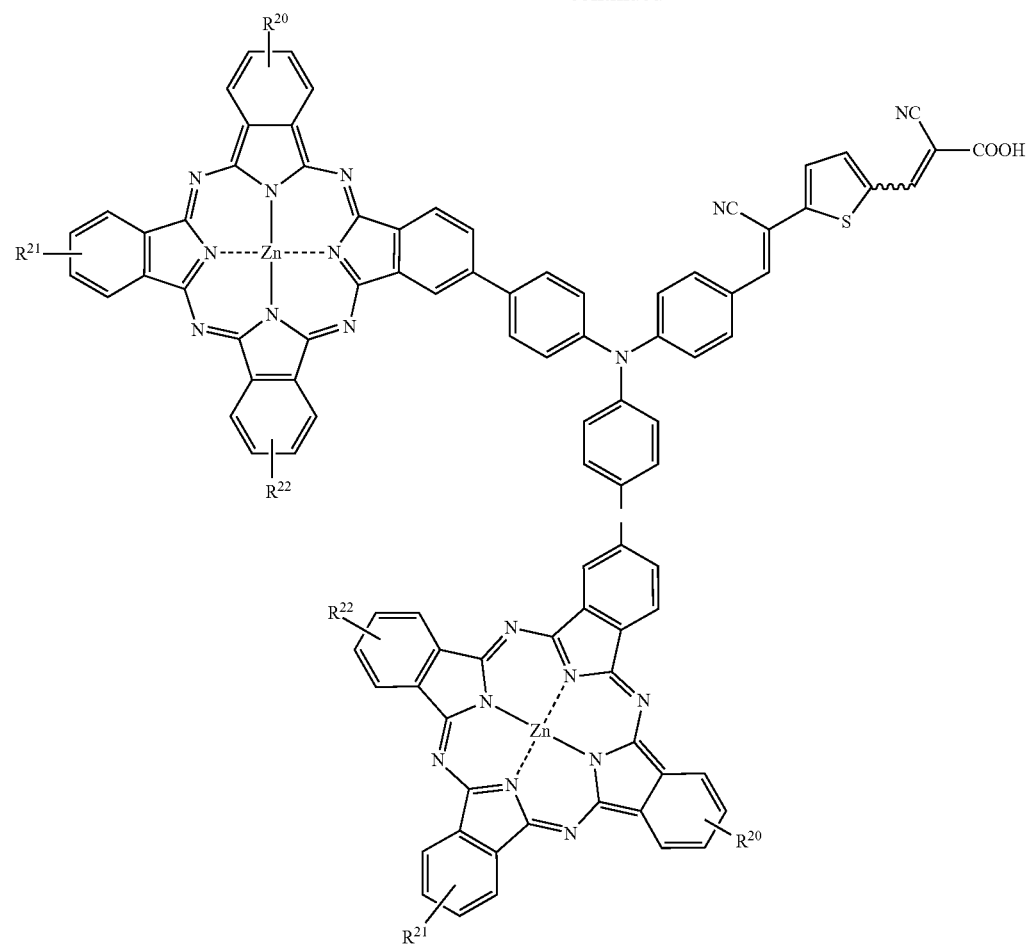
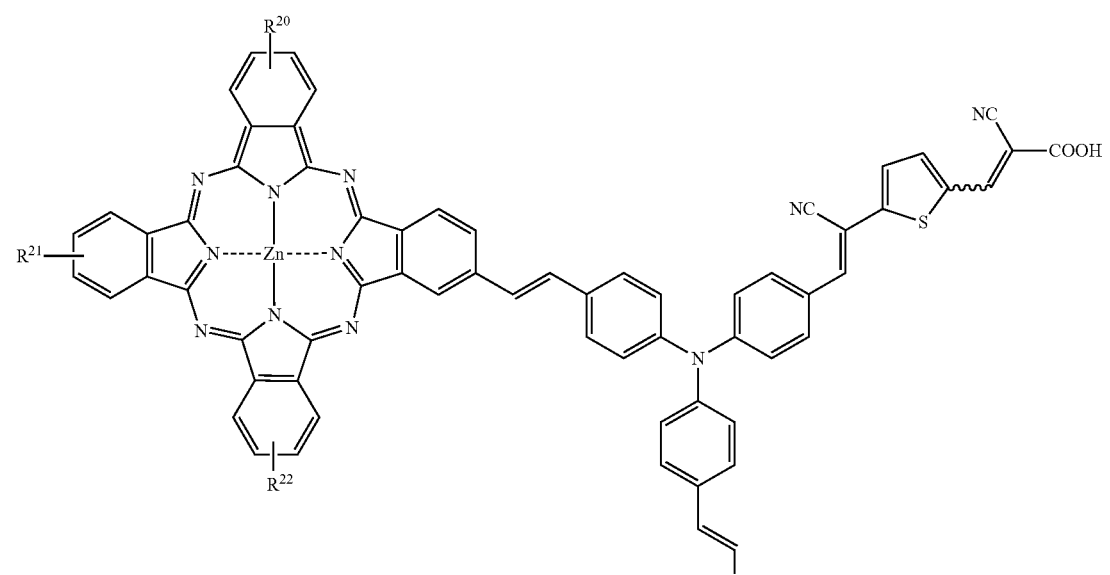

-continued
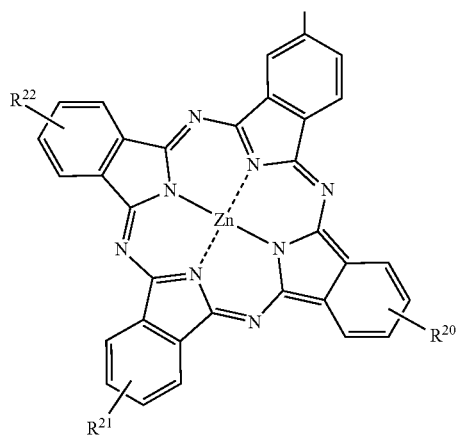
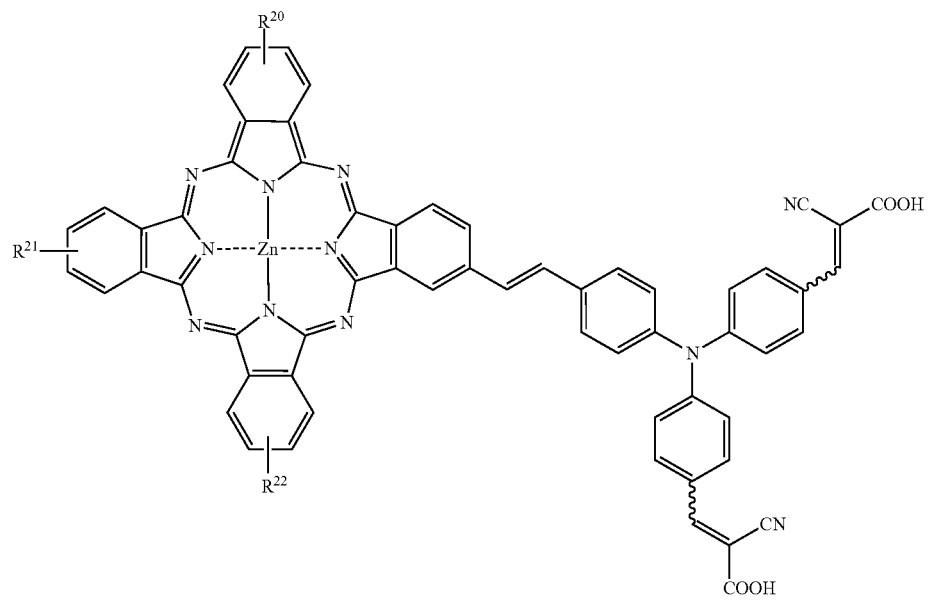
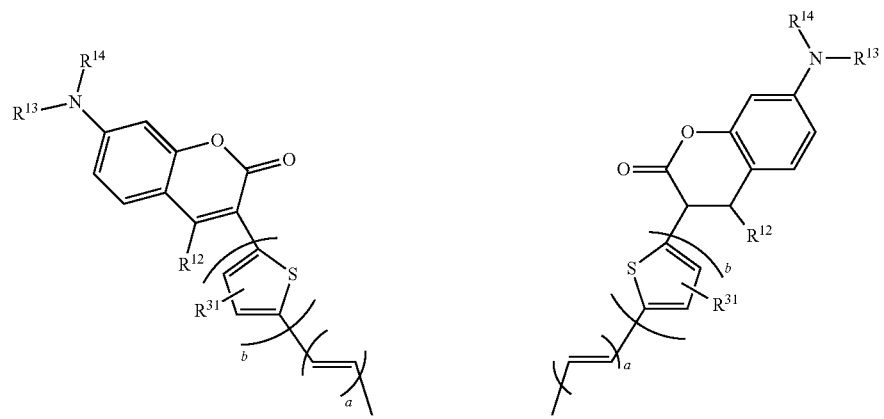

-continued
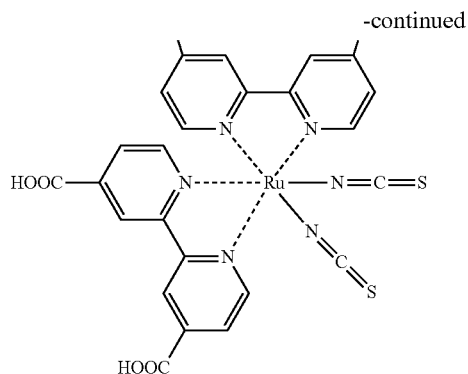
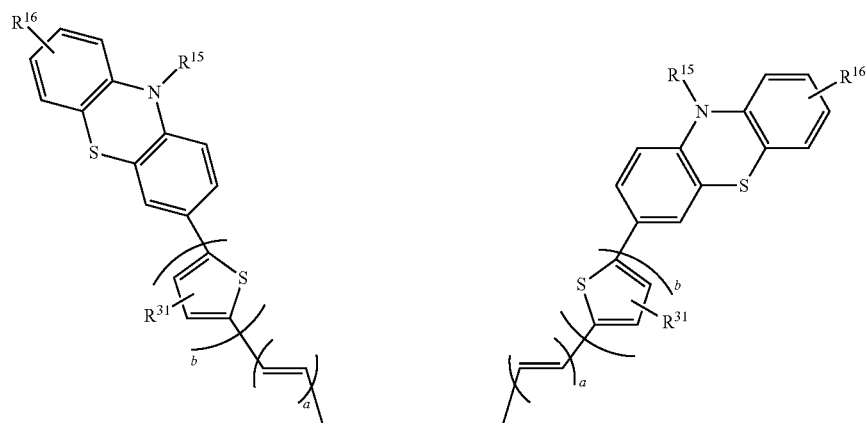
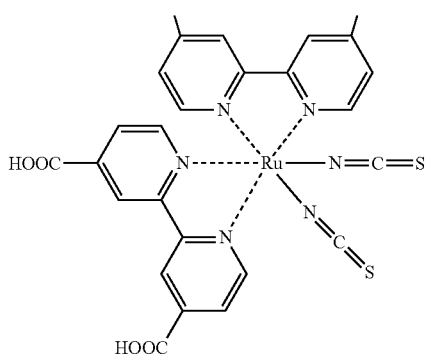
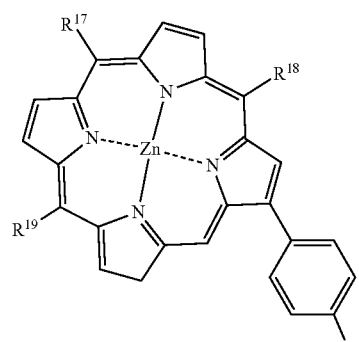
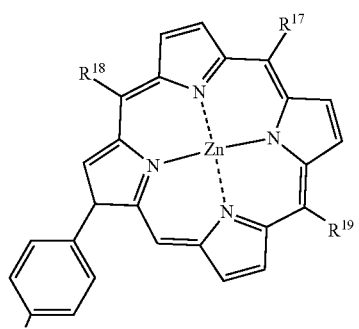

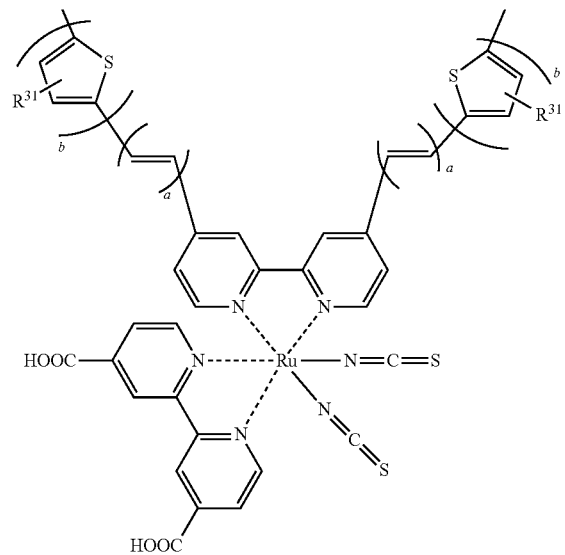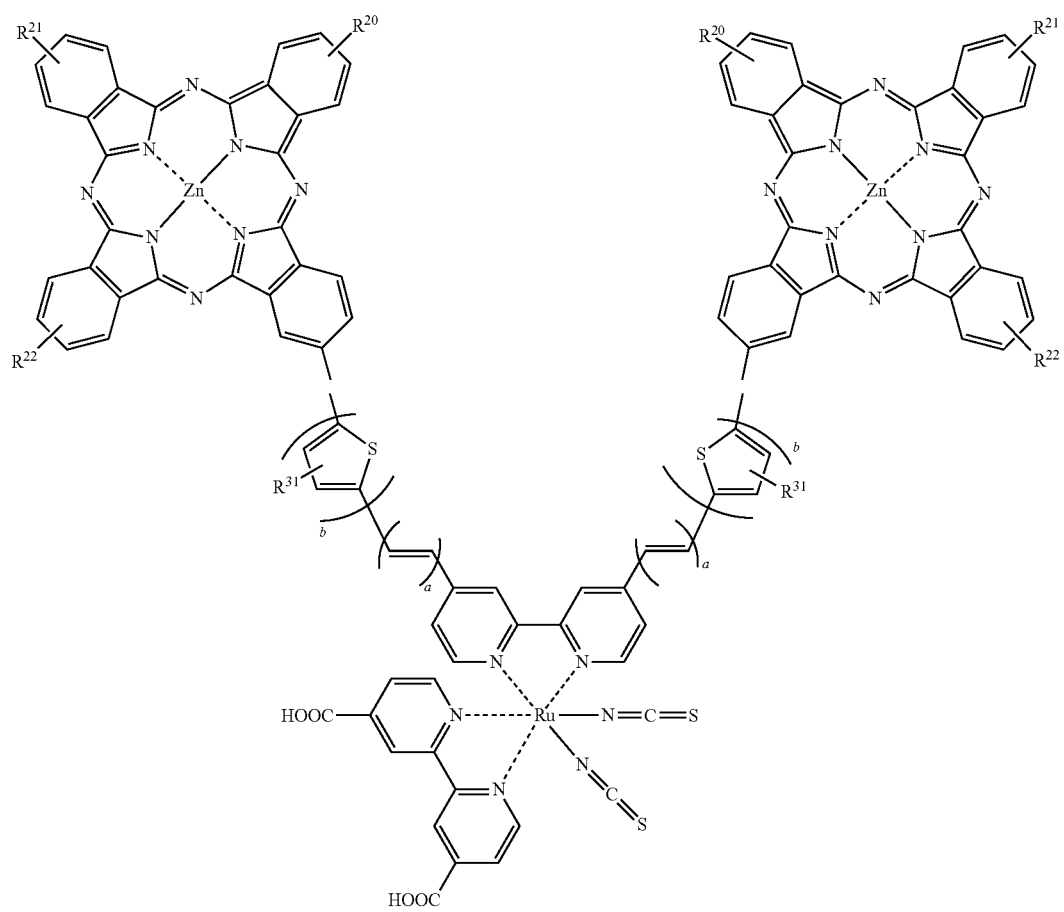

-continued
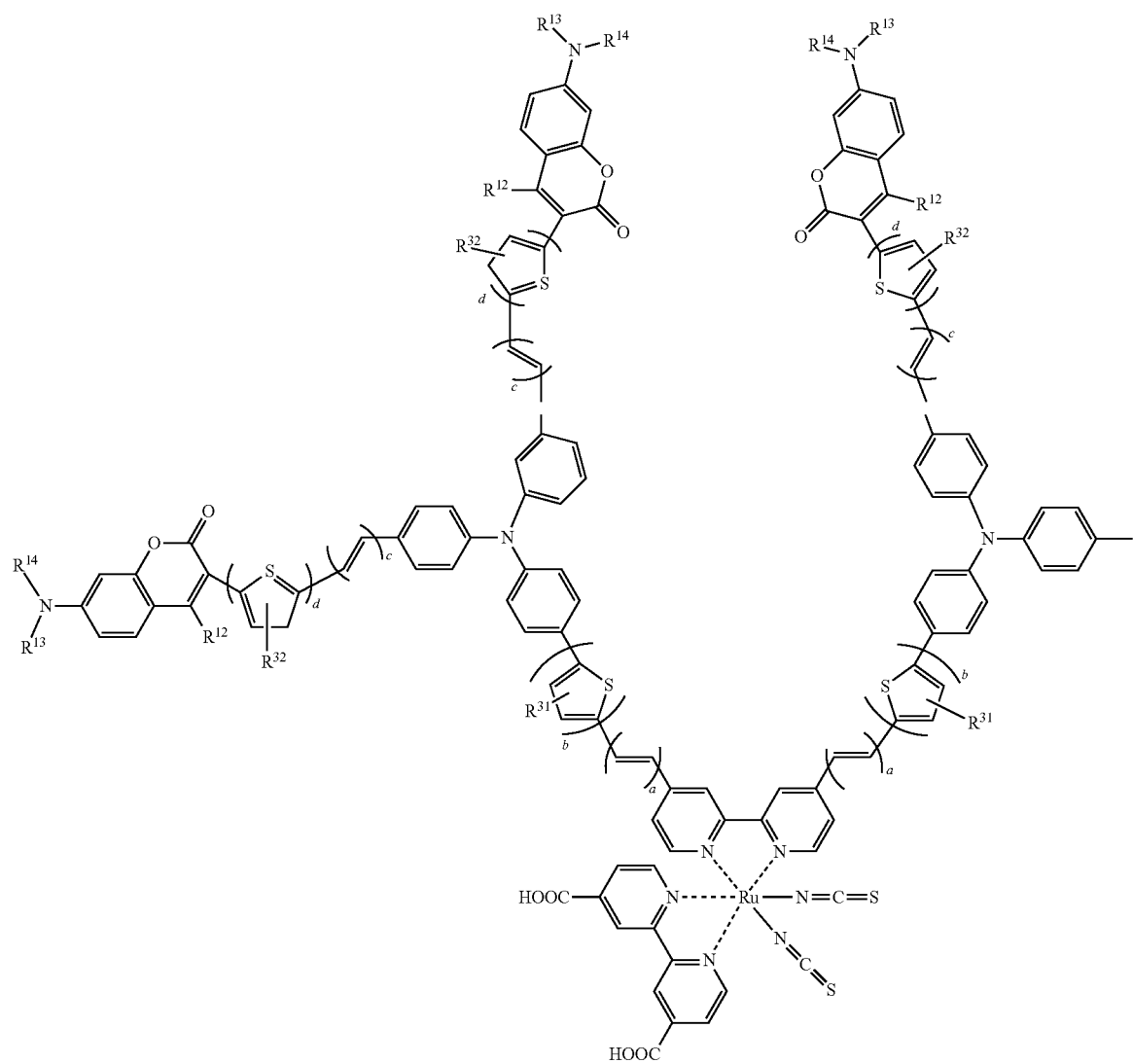
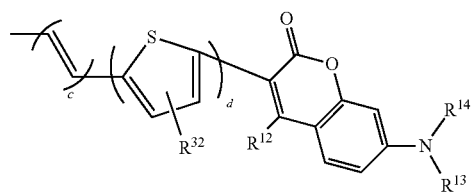

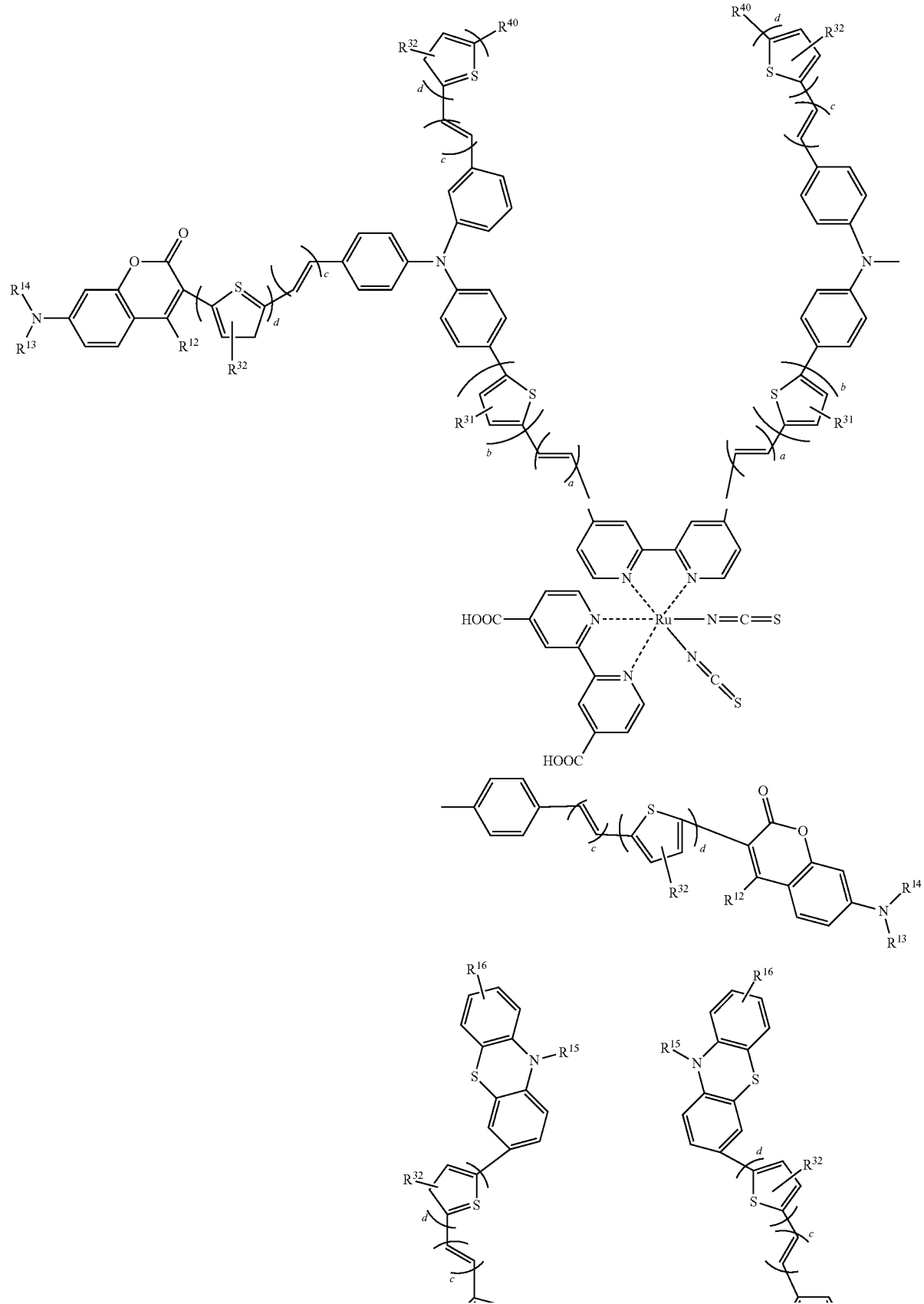

-continued
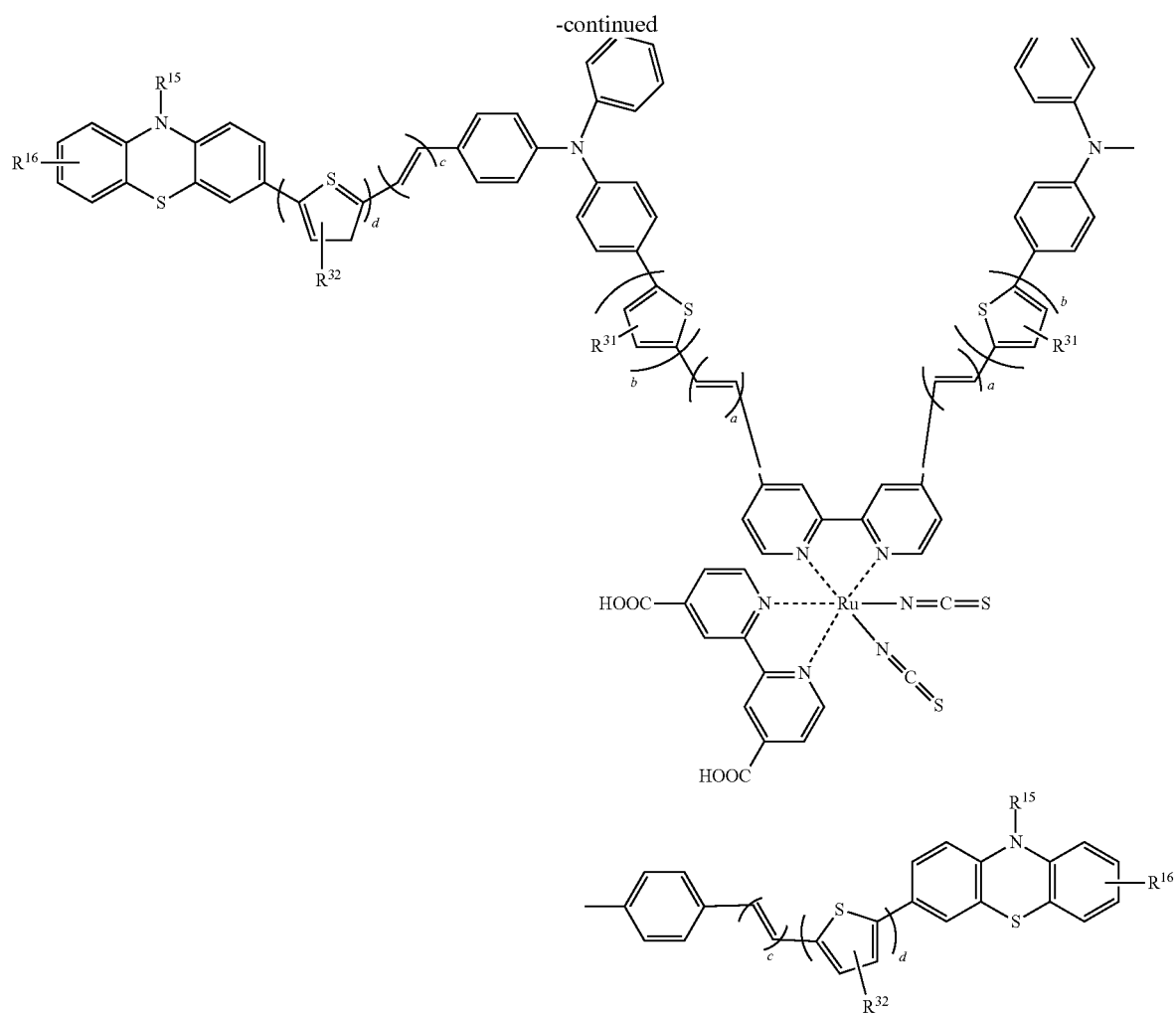
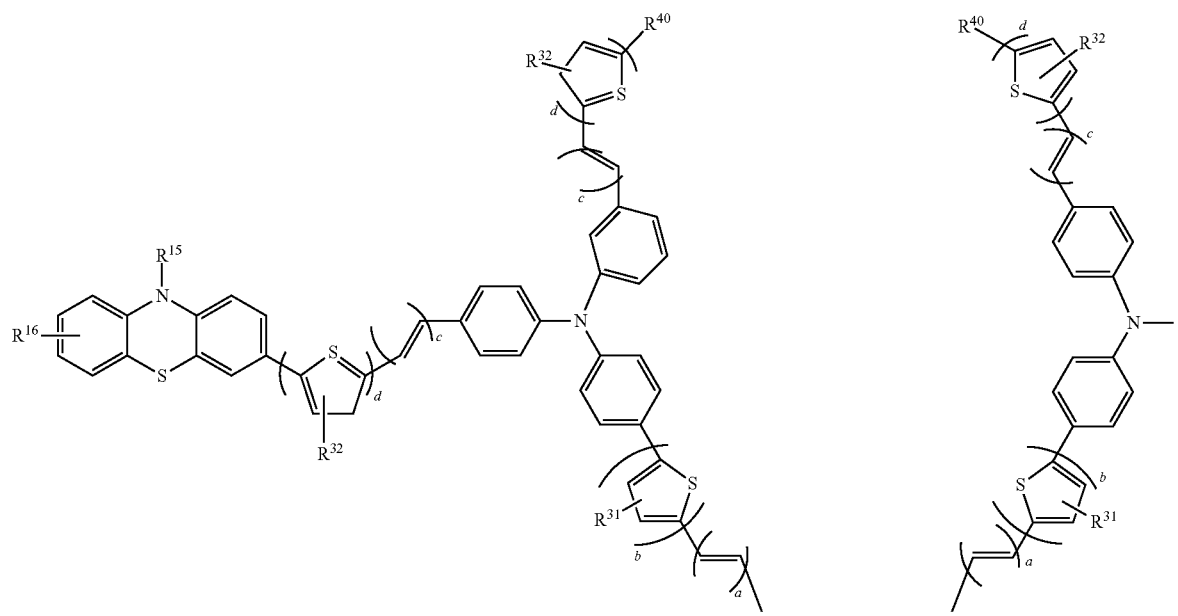

-continued
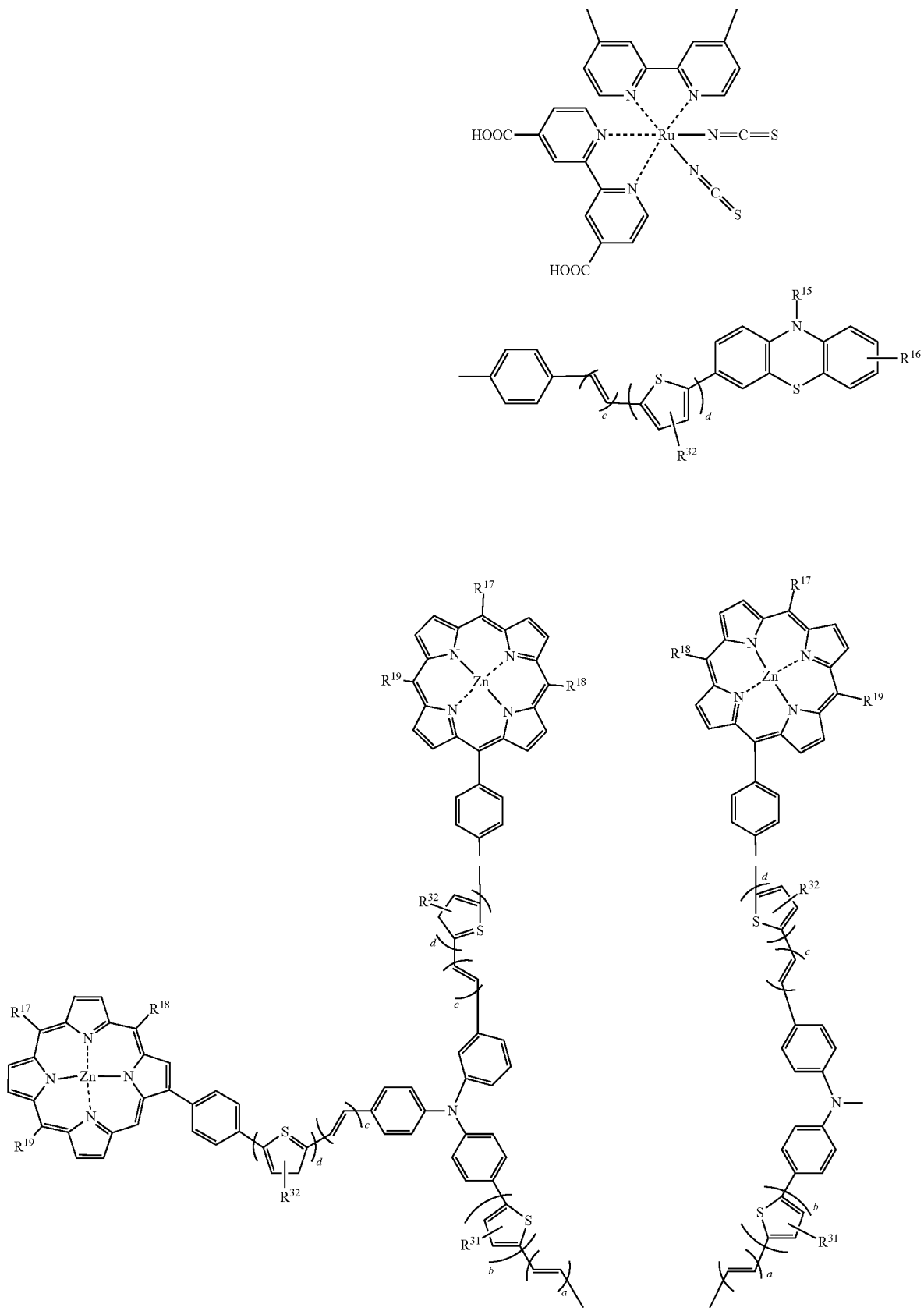

-continued
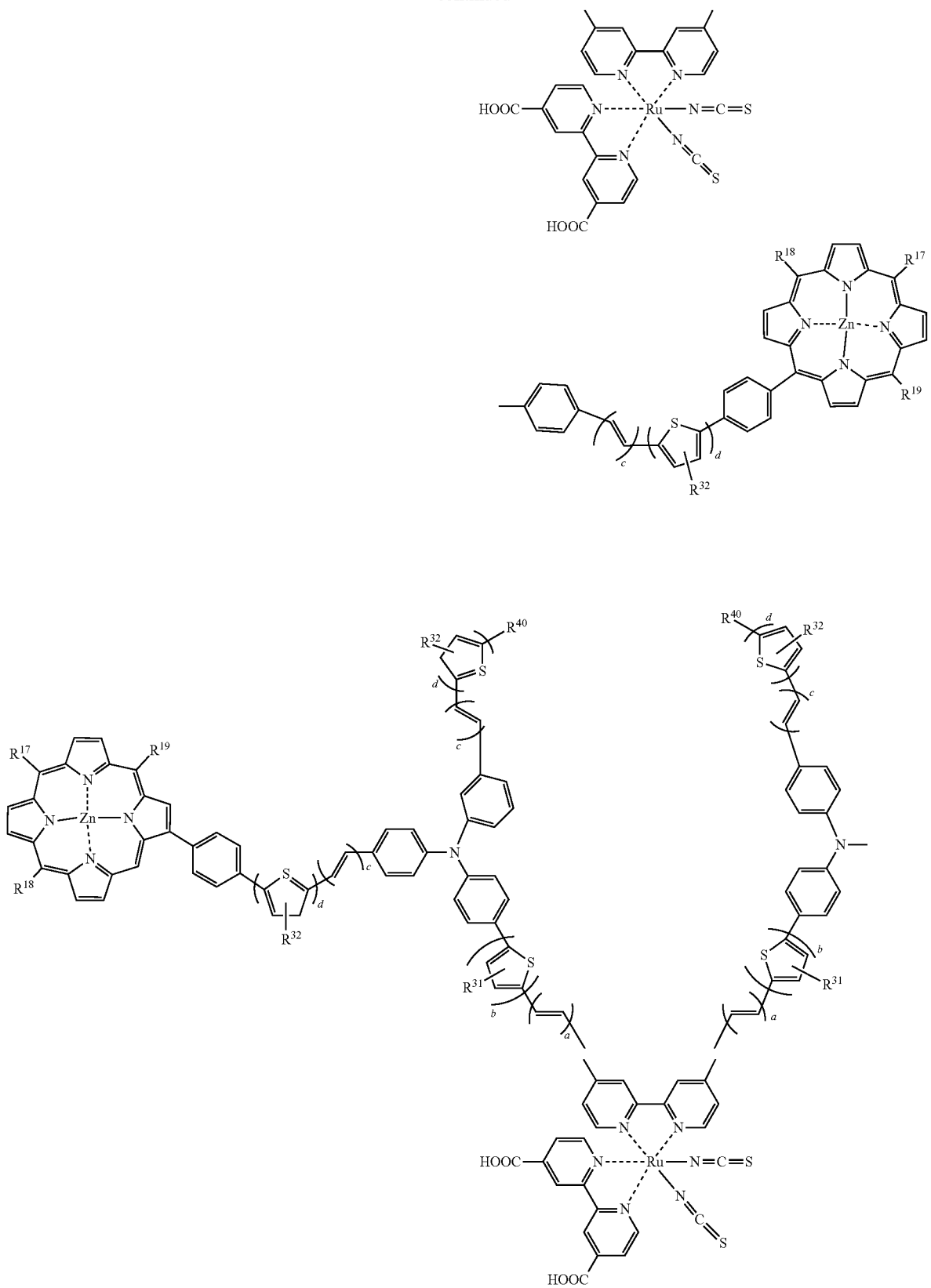

-continued
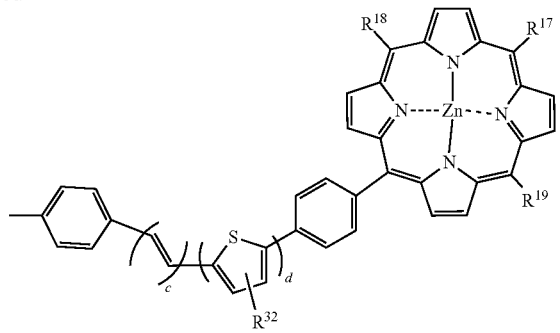
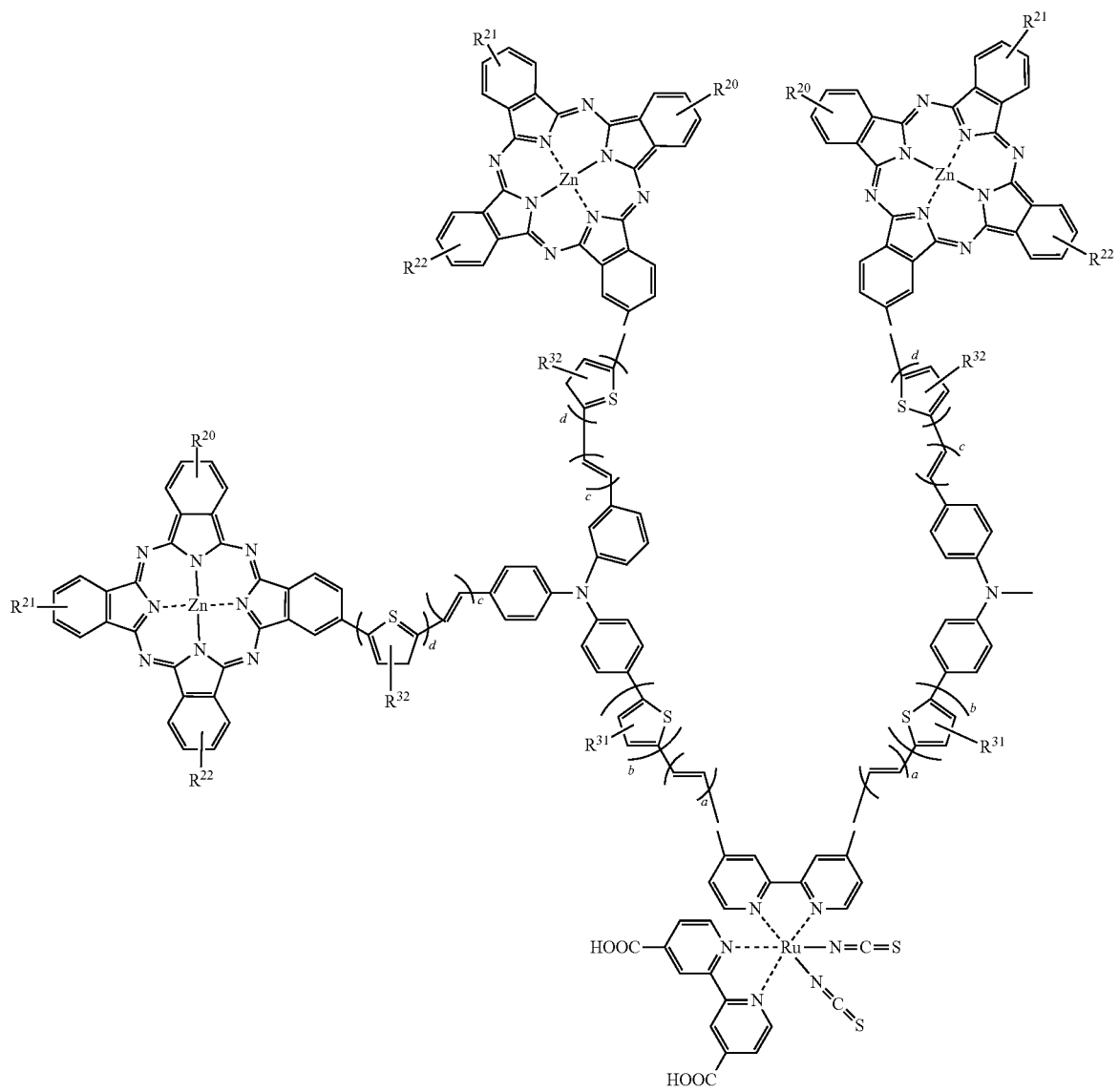

-continued
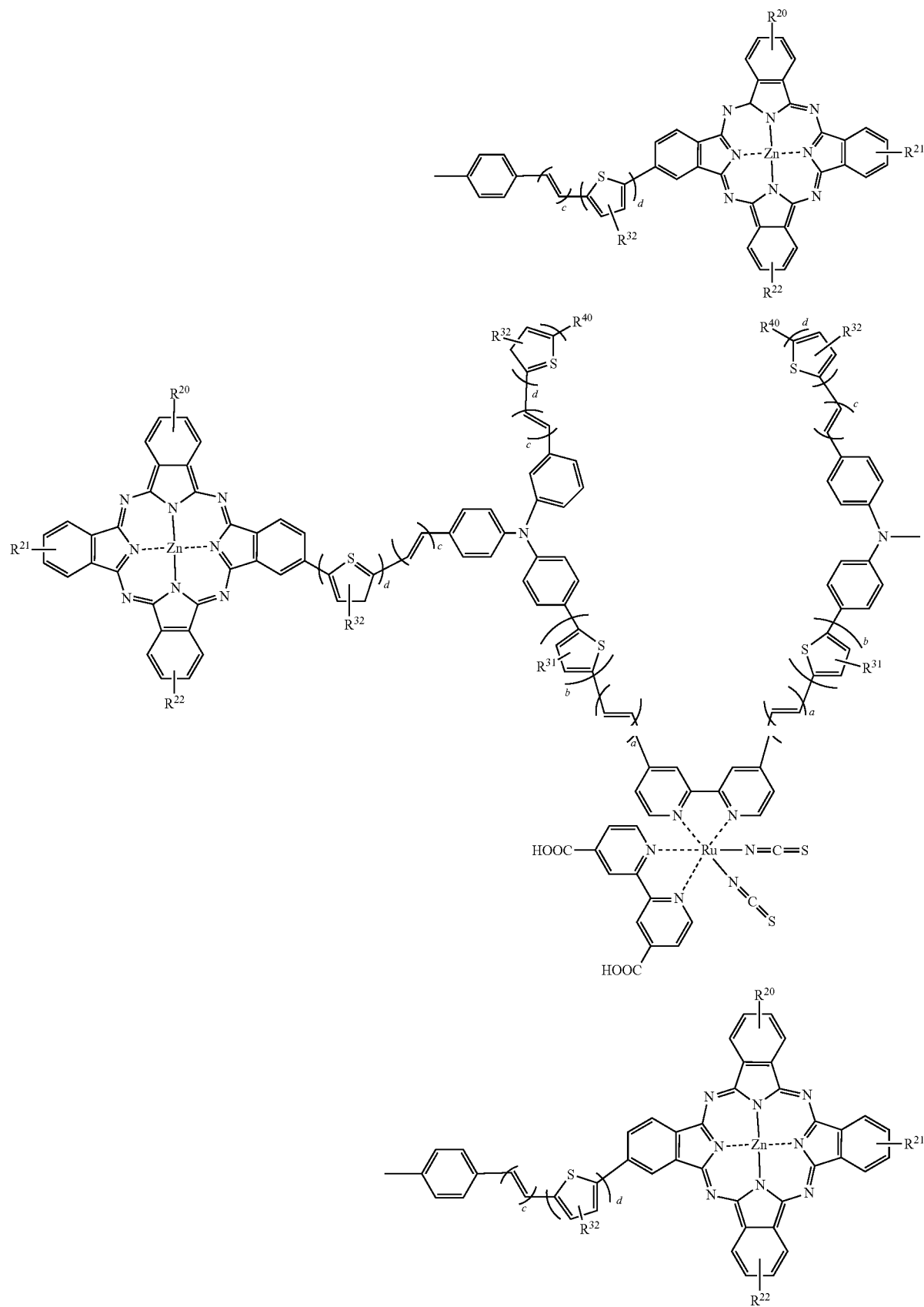

In another general aspect, there is provided a solar cell including at least one of the dye materials according to the present invention in a light-absorbing layer.

An embodiment of the solar cell including the dye material according to the present invention is shown in FIG. 1 in the form of a vertical sectional view. Referring to FIG. 1, a titanium alkoxide solution is coated on a fluorine-doped tin oxide (FTO) glass substrate, followed by drying. Titania sol is further coated thereon, followed by drying and heat treatment, to form a titania layer. The substrate having the titania layer is dipped into a dye-containing solution and then dried to allow the dye to be adsorbed onto the titania layer formed of titania particles. Meanwhile, a platinum electrode layer is formed on another FTO glass substrate. Then, the substrate having the dye layer and the substrate having the electrode layer are joined with each other to provide a solar cell having the structure as shown in FIG. 1.

DETAILED DESCRIPTION OF EMBODIMENTS

Figure 1:
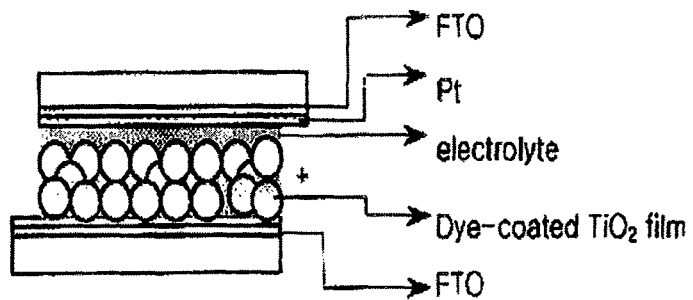
FIG. 1 is a sectional schematic view of the dye-sensitised solar cell in accordance with an embodiment of the present invention.

The examples will now be described. The following examples are for illustrative purposes only and not intended to limit the scope of this disclosure.

PREPARATION EXAMPLE 1

Preparation of Coumarin-Containing Dye (Compound 101)

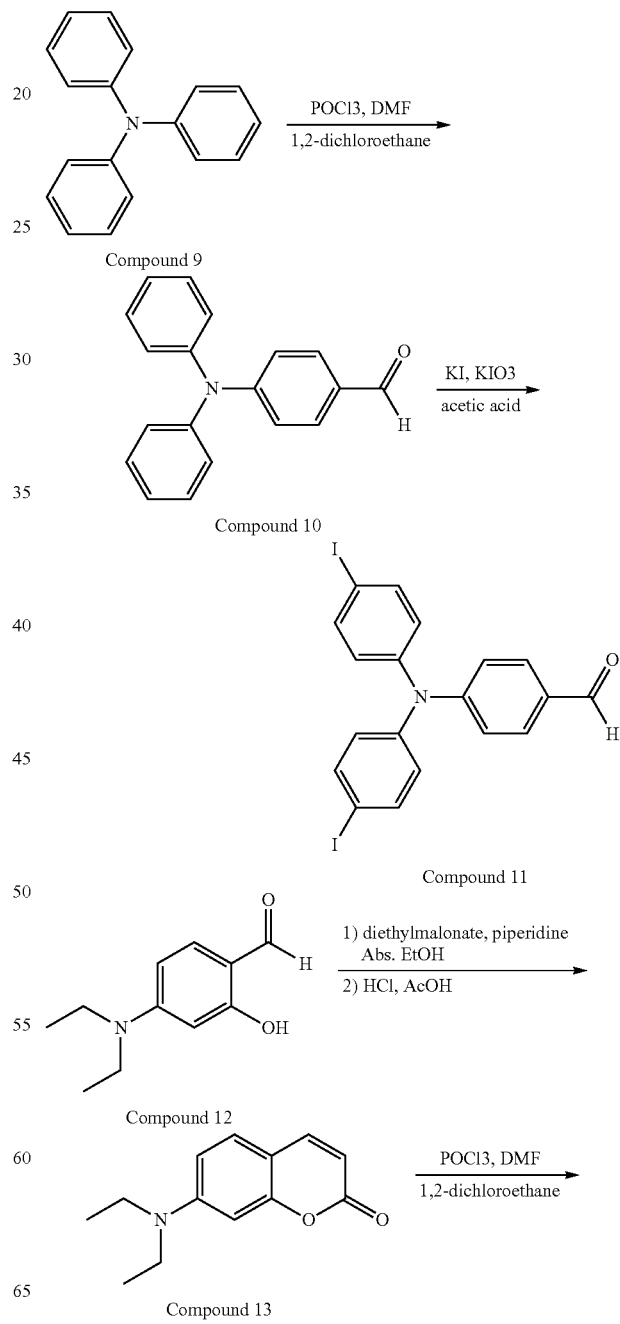

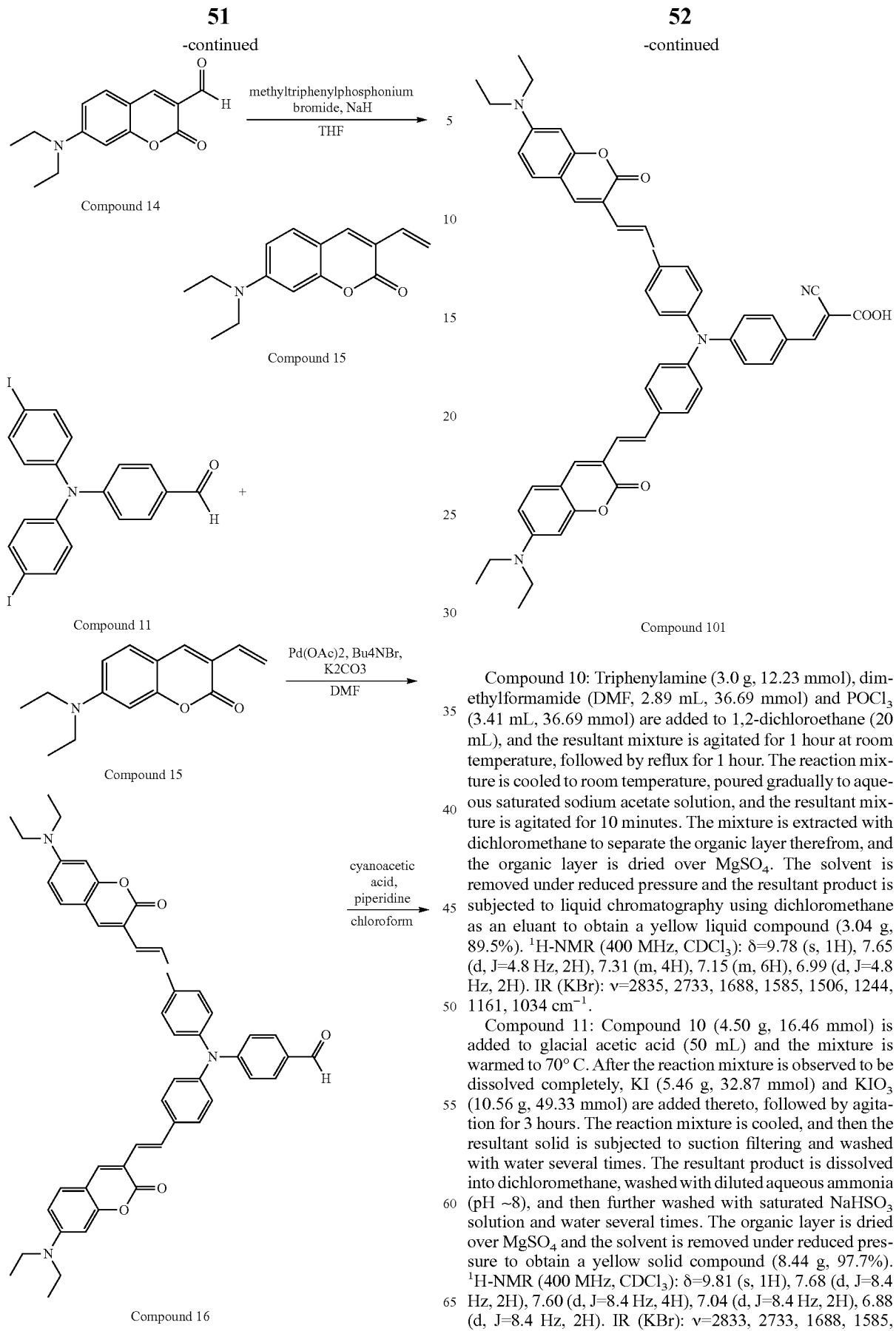

Compound 10: Triphenylamine (3.0 g, 12.23 mmol), dimethylformamide (DMF, 2.89 mL, 36.69 mmol) and POCl$_3$ (3.41 mL, 36.69 mmol) are added to 1,2-dichloroethane (20 mL), and the resultant mixture is agitated for 1 hour at room temperature, followed by reflux for 1 hour. The reaction mixture is cooled to room temperature, poured gradually to aqueous saturated sodium acetate solution, and the resultant mixture is agitated for 10 minutes. The mixture is extracted with dichloromethane to separate the organic layer therefrom, and the organic layer is dried over MgSO$_4$. The solvent is removed under reduced pressure and the resultant product is subjected to liquid chromatography using dichloromethane as an eluant to obtain a yellow liquid compound (3.04 g, 89.5%). $^1$H-NMR (400 MHz, CDCl$_3$): δ=9.78 (s, 1H), 7.65 (d, J=4.8 Hz, 2H), 7.31 (m, 4H), 7.15 (m, 6H), 6.99 (d, J=4.8 Hz, 2H). IR (KBr): ν=2835, 2733, 1688, 1585, 1506, 1244, 1161, 1034 cm$^{-1}$.

Compound 11: Compound 10 (4.50 g, 16.46 mmol) is added to glacial acetic acid (50 mL) and the mixture is warmed to 70° C. After the reaction mixture is observed to be dissolved completely, KI (5.46 g, 32.87 mmol) and KIO$_3$ (10.56 g, 49.33 mmol) are added thereto, followed by agitation for 3 hours. The reaction mixture is cooled, and then the resultant solid is subjected to suction filtering and washed with water several times. The resultant product is dissolved into dichloromethane, washed with diluted aqueous ammonia (pH ~8), and then further washed with saturated NaHSO$_3$ solution and water several times. The organic layer is dried over MgSO$_4$ and the solvent is removed under reduced pressure to obtain a yellow solid compound (8.44 g, 97.7%). $^1$H-NMR (400 MHz, CDCl$_3$): δ=9.81 (s, 1H), 7.68 (d, J=8.4 Hz, 2H), 7.60 (d, J=8.4 Hz, 4H), 7.04 (d, J=8.4 Hz, 2H), 6.88 (d, J=8.4 Hz, 2H). IR (KBr): ν=2833, 2733, 1688, 1585, 1506, 1244 cm$^{-1}$.

Compound 13: 4-(Diethylamino)salicylaldehyde (5.0 g, 25.87 mmol), diethylmalonate (5.9 mL, 51.75 mmol) and piperidine (3 mL) are added to absolute ethanol (10 mL), followed by refluxing for 2 hours. The reaction mixture is cooled and the solvent is removed completely under reduced pressure, and 35% HCl (10 mL) and glacial acetic acid (10 mL) are added thereto, followed by refluxing for 16 hours. The solution is cooled, aqueous NaOH solution is added gradually thereto to adjust the pH to ~5, and the resultant solid is subjected to suction filtering. The product is washed with water several times and dried in an oven to obtain a yellow solid compound (4.30 g, 76.5%). m.p. 85° C.; $^1$H-NMR (400 MHz, CDCl$_3$): δ=7.51 (d, J=8.8 Hz, 1H), 7.22 (d, J=8.8 Hz, 1H), 6.55 (d, J=16.4 Hz, 1H), 6.47 (s, 1H), 6.02 (d, J=10.0 Hz, 1H), 3.40 (q, 4H), 1.21 (t, 6H).

Compound 14: Compound 13 (3.0 g, 13.80 mmol), DMF (3.2 mL, 38.4 mmol) and POCl$_3$ (3.9 mL, 38.4 mmol) are added to 1,2-dichloroethane (20 mL). The mixture is agitated at room temperature for 1 hour and refluxed for 1 hour. The reaction mixture is cooled to room temperature and poured gradually to saturated aqueous sodium acetate solution, followed by agitation for 10 minutes. The mixture is extracted with dichloromethane to separate the organic layer therefrom, and the organic layer is dried over MgSO$_4$. The solvent is removed under reduced pressure and the resultant product is subjected to liquid chromatography using ethyl acetate/n-hexane (1:1) as an eluant to obtain a yellow solid compound (2.63 g, 77.6%). m.p. 182° C.; $^1$H-NMR (400 MHz, CDCl$_3$): δ=10.10 (s, 1H), 8.24 (s, 1H), 7.38 (d, J=8.8 Hz, 1H), 6.63 (d, J=8.8 Hz, 1H), 6.47 (s, 1H), 3.47 (q, 4H), 1.25 (t, 6H).

Compound 15: Methyltriphenylphosphonium bromide (1.94 g, 5.42 mmol) and NaH (0.16 g, 6.78 mmol) are added to tetrahydrofuran (THF, 5 mL), followed by agitation for 1 hour, and then Compound 14 (1.0 g, 4.52 mmol) is further added thereto, followed by agitation for 16 hours. Water (50 mL) is added to the reaction mixture, the resultant mixture is extracted with dichloromethane to separate the organic layer therefrom, and the organic layer is dried over MgSO$_4$. The solvent is removed under reduced pressure and the resultant product is subjected to liquid chromatography using dichloromethane as an eluant to obtain a yellow liquid compound (0.80 g, 80.8%). $^1$H-NMR (400 MHz, CDCl$_3$): δ=7.56 (s, 1H), 7.24 (d, J=8.8 Hz, 1H), 6.65 (dd, J=11.2 Hz, 11.2 Hz, 1H), 6.55 (d, J=8.8 Hz, 1H), 6.46 (s, 1H), 6.02 (d, J=9.6 Hz, 1H), 5.28 (d, J=9.0 Hz, 1H), 3.47 (q, 4H), 1.25 (t, 6H).

Compound 16: Compound 15 (0.15 g, 0.68 mmol), Compound 11 (0.15 g, 0.28 mmol), Pd(OAc)$_2$ (3 mg, 0.014 mmol), K$_2$CO$_3$ (0.14 g, 0.14 mmol) and Bu$_4$NBr (0.18 g, 0.57 mmol) are added to DMF (5 mL), and the mixture is warmed to 95° C., followed by refluxing for 16 hours. The reaction mixture is cooled, water (50 mL) is added thereto and the mixture is extracted with dichloromethane. The organic layer is separated and dried over MgSO$_4$. The solvent is removed under reduced pressure and the resultant product is subjected to liquid chromatography using ethyl acetate/n-hexane (1:1) as an eluant to obtain an orange solid compound (0.12 g, 60.0%). $^1$H-NMR (400 MHz, CDCl$_3$): δ=9.81 (s, 1H), 7.70 (d, J=8.8 Hz, 2H), 7.65 (s, 2H), 7.45 (m, 6H), 7.26 (d, J=8.8 Hz, 2H), 7.11 (d, J=8.8 Hz, 4H), 7.04 (m, 4H), 6.58 (dd, J=2.4 Hz, 2.4 Hz, 2H), 6.49 (d, J=2.4 Hz, 2H), 3.42 (q, 8H), 1.22 (t, 12H).

Compound 101: Compound 16 (0.30 g, 0.34 mmol), cyanoacetic acid (0.29 g, 3.37 mmol) and peperidine (0.1 mL, 1.01 mmol) are added to dry chloroform (30 mL), followed by refluxing for 6 hours. The reaction mixture is cooled, water (50 mL) is added thereto and the mixture is extracted with chloroform. The organic layer is separated and dried over MgSO$_4$. The solvent is removed under reduced pressure and the resultant product is subjected to liquid chromatography using methanol/dichloromethane (1:6) as an eluant to obtain an orange solid compound (0.24 g, 74.4%). $^1$H-NMR (400 MHz, DMSO, d$_6$): δ=8.04 (s, 2H), 7.83 (s, 1H), 7.80 (d, J=8.8 Hz, 2H), 7.52 (d, J=8.8 Hz, 4H), 7.46 (d, J=7.6 Hz, 2H), 7.46 (s, 2H), 7.08 (d, J=8.4 Hz, 4H), 7.03 (m, 4H), 6.70 (dd, J=2.4 Hz, 2.4 Hz, 2H), 6.54 (d, J=2.4 Hz, 2H), 3.47 (q, 8H), 1.25 (t, 12H).

Figure 2:
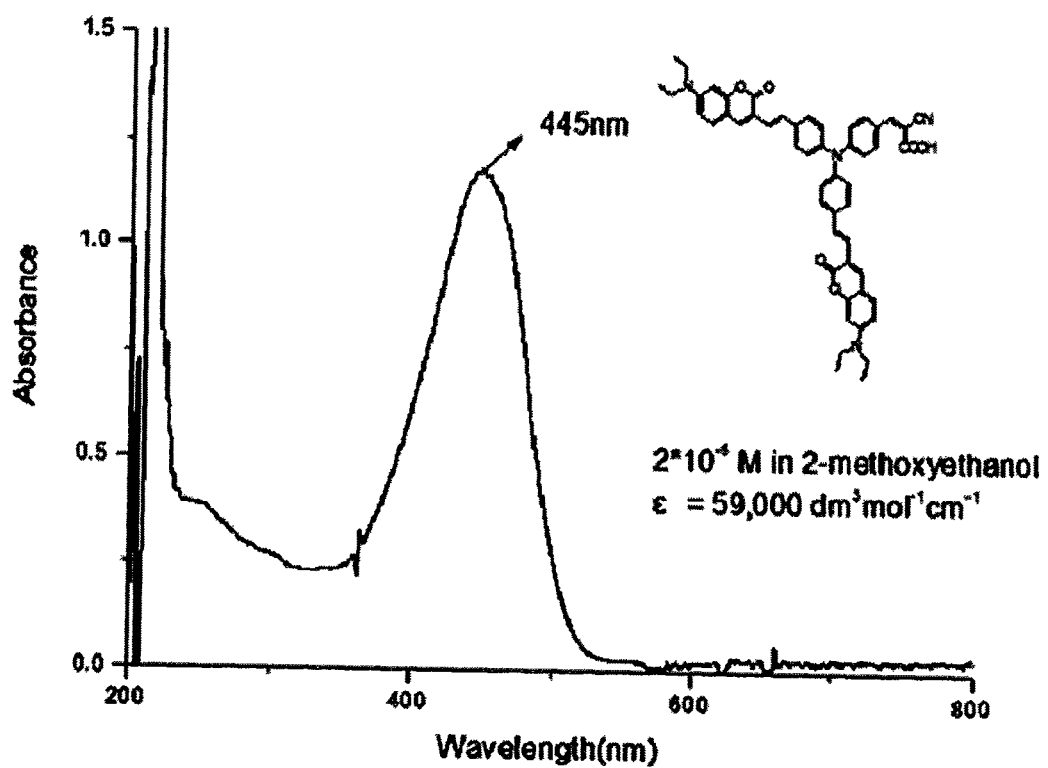
FIG. 2 is a graph showing the absorbance of the dye (Compound 101) obtained from Preparation Example 1.

Compound 101 is determined by UV-Vis absorption spectrometry at a concentration of 2×10$^{-5}$ M in 2-methoxyethanol as a solvent. The result is shown in FIG. 2 and Compound 101 has an absorbance of 59000 dm$^3$ mol$^{-1}$cm$^{-1}$.

PREPARATION EXAMPLE 2

Preparation of Coumarin-Containing Dye (Compound 102)

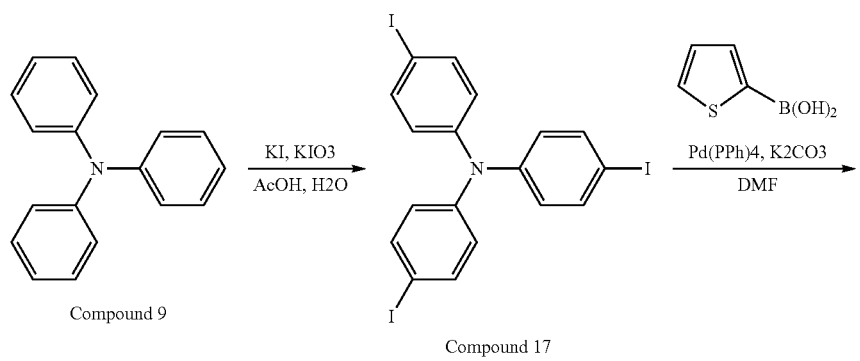

-continued
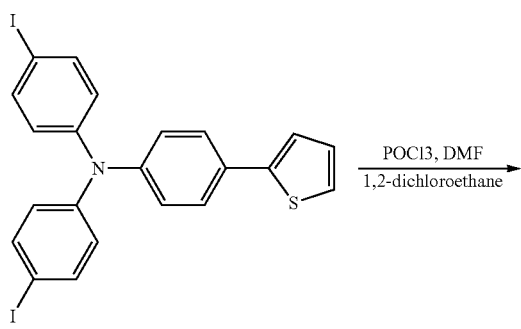
Compound 18
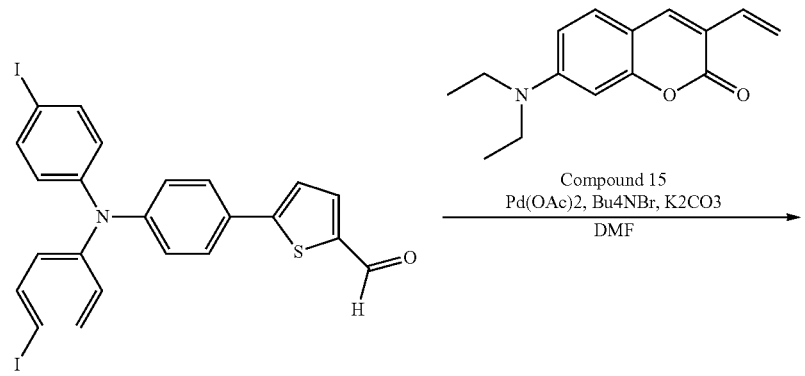
Compound 19
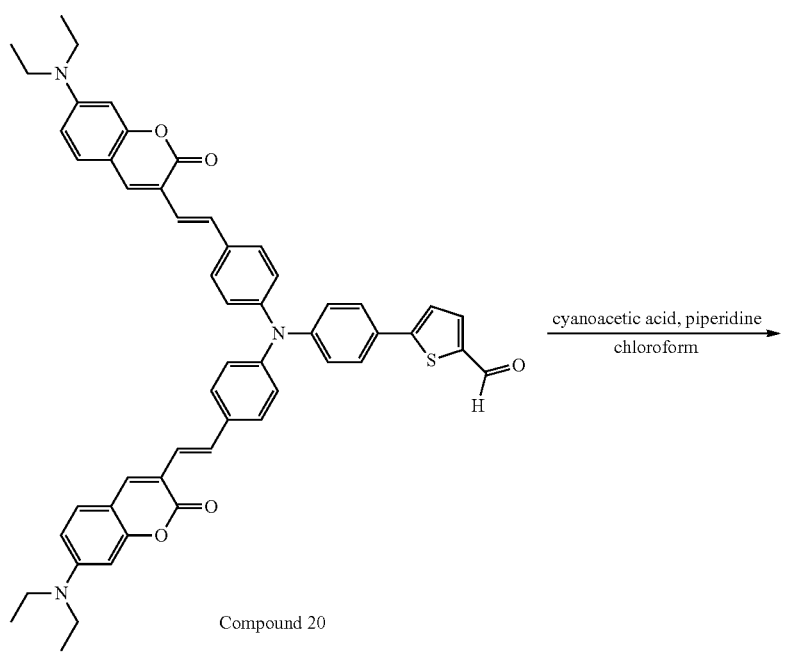
Compound 20

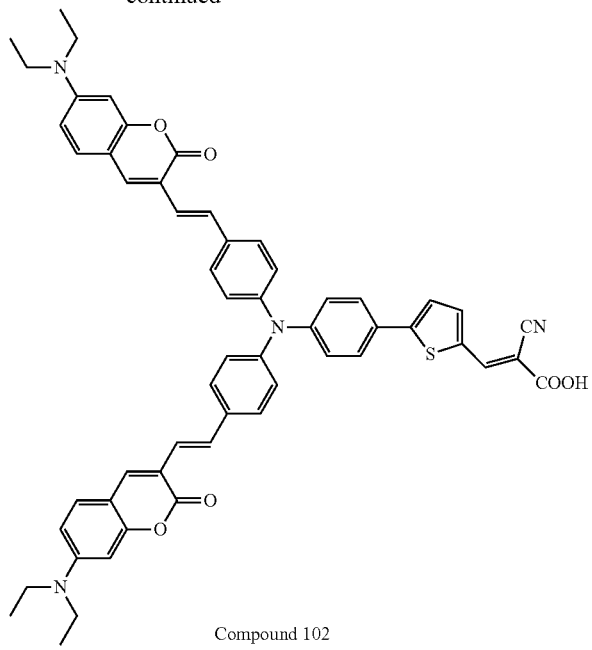

Compound 102

Compound 17: Triphenylamine (6.13 g, 25.0 mmol) and KI (8.3 g, 50.0 mmol) are added to glacial acetic acid (100 mL) and water (10 mL), followed by refluxing. After the reaction mixture is observed to be dissolved completely, $KIO_3$ (10.7 g, 50.0 mmol) is added thereto, followed by refluxing for 1 hour. The reaction mixture is cooled, water (50 mL) is added thereto, and then the resultant solid is subjected to suction filtering and washed with water several times. The resultant product is dissolved into dichloromethane, and the organic layer is washed with saturated sodium thiosulfate solution. The organic layer is dried over $MgSO_4$ and the solvent is removed under reduced pressure to obtain a yellow solid compound (14.5 g, 93.1%). $^1$H-NMR (400 MHz, $CDCl_3$): δ=7.50 (d, 6H), 6.80 (d, 6H).

Compound 18: Compound 17 (6.10 g, 9.79 mmol), 2-thiopheneboronic acid (0.42 g, 3.26 mmol), $Pd(PPh)_4$ (0.15 g, 0.13 mmol) and $K_2CO_3$ (1.18 g, 9.79 mmol) are added to DMF (5 mL) and the mixture is warmed to 60° C., followed by agitation for 2 hours. The reaction mixture is cooled, water (50 mL) is added thereto and the mixture is extracted with dichloromethane. The organic layer is separated and dried over $MgSO_4$. The solvent is removed under reduced pressure and the resultant product is subjected to liquid chromatography using dichloromethane/n-hexane (1:3) as an eluant to obtain a white solid compound (0.76 g, 40.2%). $^1$H-NMR (400 MHz, $CDCl_3$): δ=7.52 (d, 4H), 7.47 (d, 2H), 7.23 (m, 1H), 7.04 (m, 3H), 6.84 (d, 4H), 6.79 (d, 1H).

Compound 19: Compound 18 (0.48 g, 0.83 mmol), DMF (0.19 mL, 2.49 mmol) and $POCl_3$ (0.23 mL, 2.49 mmol) are added to 1,2-dichloroethane (20 mL). The mixture is agitated for 1 hour at room temperature and is refluxed for 16 hours. The reaction mixture is cooled to room temperature and poured gradually to saturated aqueous sodium acetate solution, followed by agitation for 10 minutes. The mixture is extracted with dichloromethane to separate the organic layer therefrom, and the organic layer is dried over $MgSO_4$. The solvent is removed under reduced pressure and the resultant product is subjected to liquid chromatography using dichloromethane/n-hexane (1:1) as an eluant to obtain a yellow solid compound (0.19 g, 38.0%). $^1$H-NMR (400 MHz, $CDCl_3$): δ=9.85 (s, 1H), 7.70 (d, 1H), 7.55 (d, 4H), 7.52 (d, 2H), 7.30 (d, 1H), 7.05 (d, 2H), 6.85 (d, 4H).

Compound 20: Compound 15 (0.41 g, 1.68 mmol), Compound 19 (0.28 g, 0.46 mmol), $Pd(OAc)_2$ (5 mg, 0.023 mmol), $K_2CO_3$ (0.22 g, 1.84 mmol) and $Bu_4NBr$ (0.30 g, 0.92 mmol) are added to DMF (5 mL), and the mixture is warmed to 95° C., followed by agitation for 6 hours. The reaction mixture is cooled, water (50 mL) is added thereto and the mixture is extracted with dichloromethane. The organic layer is separated and dried over $MgSO_4$. The solvent is removed under reduced pressure and the resultant product is subjected to liquid chromatography using dichloromethane as an eluant to obtain an orange solid compound (0.36 g, 100.0%). $^1$H-NMR (400 MHz, $CDCl_3$): δ=9.81 (s, 1H), 7.70 (d, 1H), 7.65 (s, 2H), 7.54 (d, 2H), 7.43 (d, 4H), 7.40 (s, 2H), 7.31 (d, 1H), 7.28 (d, 2H), 7.20 (s, 2H), 7.10 (d, 4H), 7.02 (d, 2H), 6.58 (dd, 2H), 6.51 (d, 2H), 3.42 (q, 8H), 1.22 (t, 12H).

Compound 102: Compound 20 (0.36 g, 0.43 mmol), cyanoacetic acid (0.37 g, 4.30 mmol) and peperidine (0.13 mL, 1.29 mmol) are added to dry chloroform (30 mL), followed by refluxing for 6 hours. The reaction mixture is cooled, water (50 mL) is added thereto and the mixture is extracted with chloroform. The organic layer is separated and dried over $MgSO_4$. The solvent is removed under reduced pressure and the resultant product is subjected to liquid chromatography using methanol/dichloromethane (1:10) as an eluant to obtain an orange solid compound (0.29 g, 76.3%). $^1$H-NMR (400 MHz, DMSO, $d_6$): δ=8.04 (d, 2H), 7.93 (s, 1H), 7.70 (d, 1H), 7.64 (d, 2H), 7.53 (d, 1H), 7.50 (d, 4H), 7.46 (d, 2H), 7.42 (s, 2H), 7.04 (m, 8H), 6.71 (d, 2H), 6.54 (d, 2H), 3.47 (q, 8H), 1.25 (t, 12H).

Figure 3:
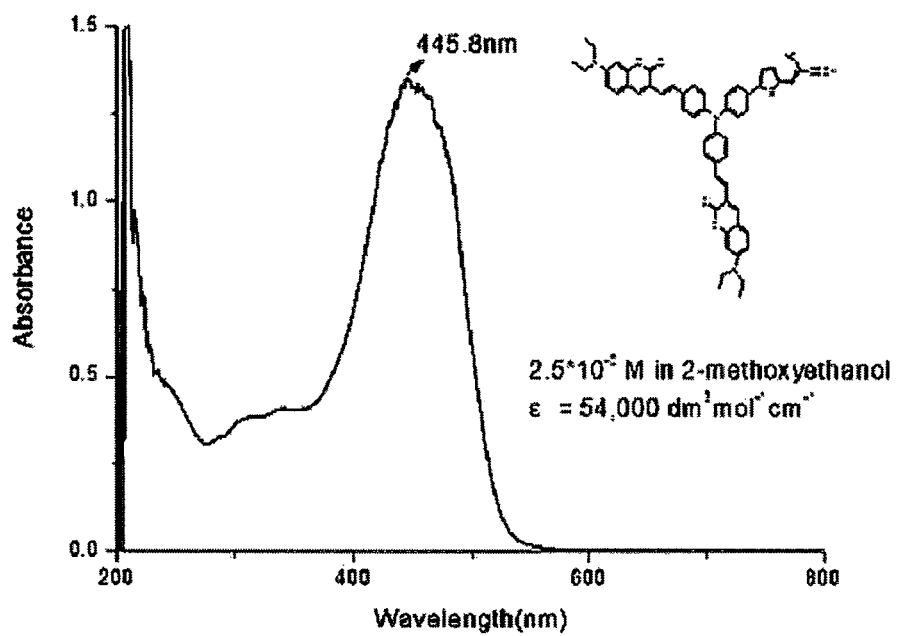
FIG. 3 is a graph showing the absorbance of the dye (Compound 102) obtained from Preparation Example 2.

Compound 102 is determined by UV-Vis absorption spectrometry at a concentration of $2.5\times10^{-5}$ M in 2-methoxyethanol as a solvent. The result is shown in FIG. 3 and Compound 102 has an absorbance of 54000 $dm^3$ $mol^{-1}$ $cm^{-1}$.

PREPARATION EXAMPLE 3
Preparation of Coumarin-Containing Dye
(Compound 103)
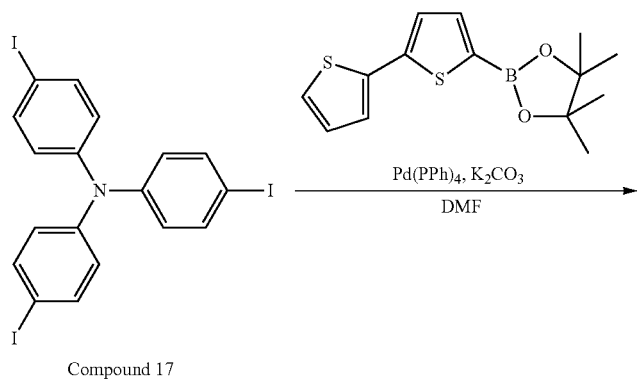
Compound 17
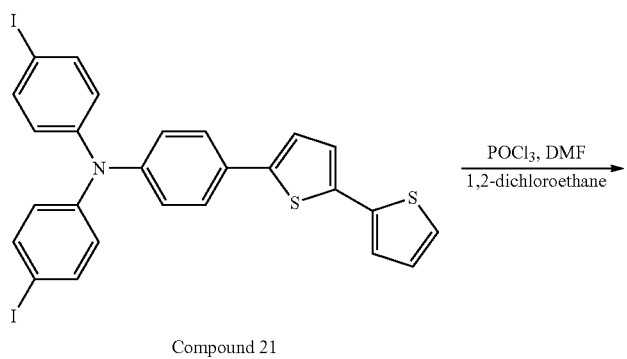
Compound 21
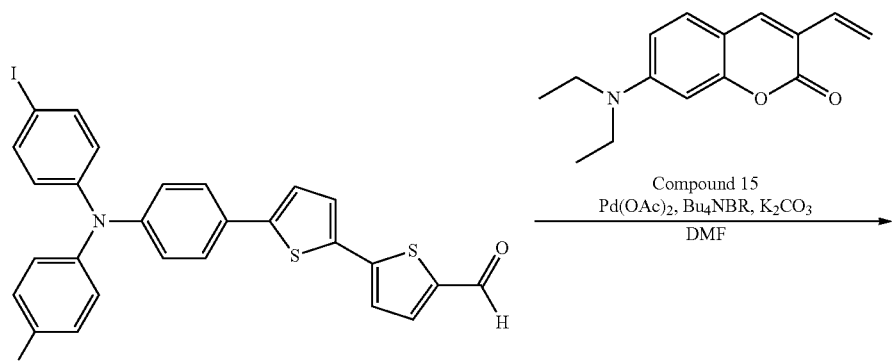
Compound 22

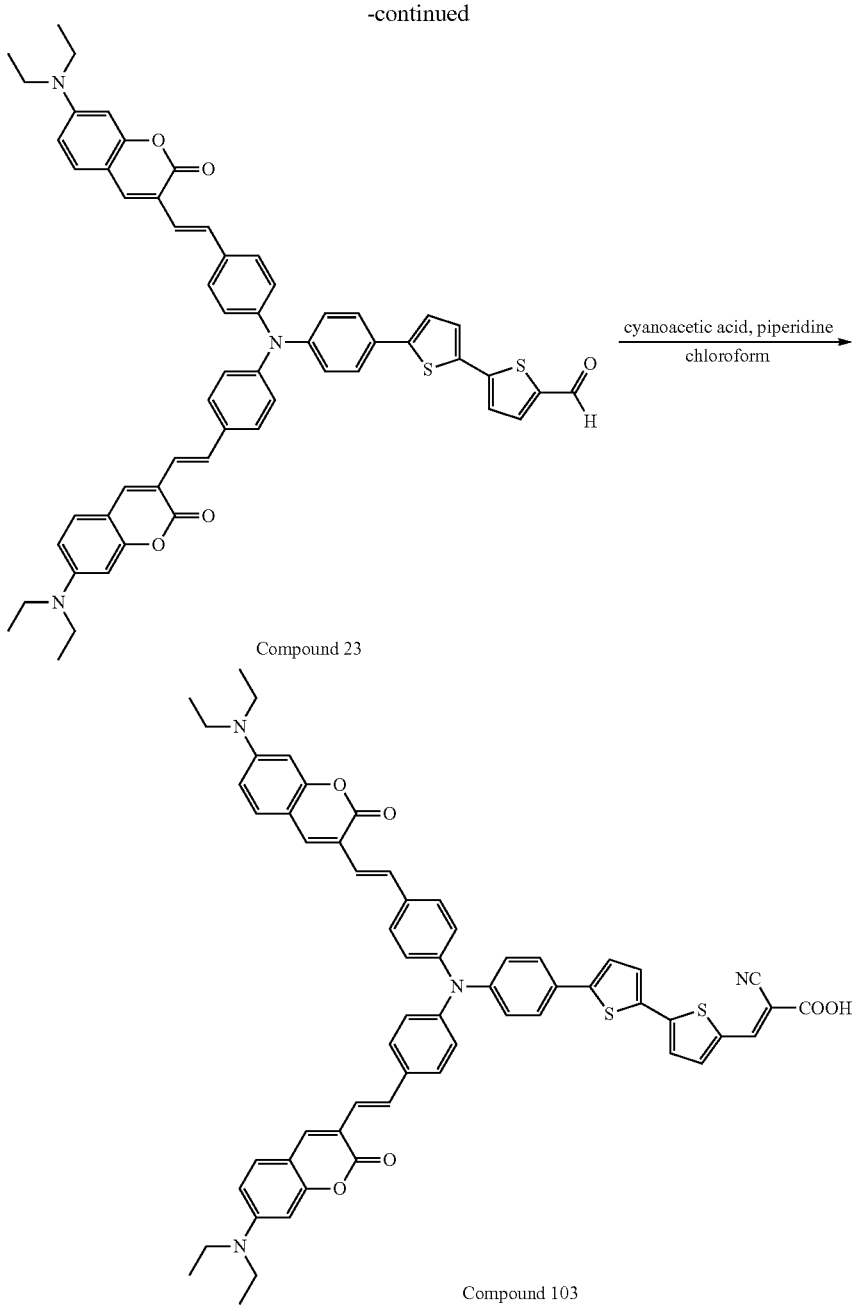

Compound 21: Compound 17 (3.20 g, 5.13 mmol), 2,2'-bithiophene-5-boronic acid pinacol ester (0.50 g, 1.71 mmol), Pd(PPh)₄ (79 mg, 0.068 mmol) and K₂CO₃ (0.62 g, 5.13 mmol) are added to DMF (5 mL) and the mixture is warmed to 60° C., followed by agitation for 2 hours. The reaction mixture is cooled, water (50 mL) is added thereto and the mixture is extracted with dichloromethane. The organic layer is separated and dried over MgSO₄. The solvent is removed under reduced pressure and the resultant product is subjected to liquid chromatography using dichloromethane/n-hexane (1:3) as an eluant to obtain a yellow solid compound (0.70 g, 61.9%). ¹H-NMR (400 MHz, CDCl₃): δ=7.56 (d, 4H), 7.49 (d, 2H), 7.23 (d, 1H), 7.21 (d, 1H), 7.15 (m, 2H), 7.05 (m, 3H), 6.87 (d, 4H).

Compound 22: Compound 21 (0.70 g, 1.06 mmol), DMF (0.25 mL, 3.18 mmol) and POCl₃ (0.30 mL, 3.18 mmol) are added to 1,2-dichloroethane (20 mL). The mixture is agitated for 1 hour at room temperature and is refluxed for 2 hours. The reaction mixture is cooled to room temperature and poured gradually to saturated aqueous sodium acetate solution, followed by agitation for 10 minutes. The mixture is extracted with dichloromethane to separate the organic layer therefrom, and the organic layer is dried over MgSO₄. The solvent is removed under reduced pressure and the resultant product is subjected to liquid chromatography using dichloromethane as an eluant to obtain an orange solid compound (0.24 g, 32.9%). ¹H-NMR (400 MHz, CDCl₃): δ=9.88 (s, 1H), 7.70 (d, 1H), 7.55 (d, 4H), 7.50 (d, 2H), 7.34 (d, 1H), 7.27 (d, 1H), 7.20 (d, 1H), 7.08 (d, 2H), 6.89 (d, 4H).

Compound 23: Compound 15 (0.20 g, 0.82 mmol), Compound 22 (0.24 g, 0.35 mmol), Pd(OAc)₂ (4 mg, 0.017 mmol), $K_2CO_3$ (0.17 g, 1.40 mmol) and $Bu_4NBr$ (0.22 g, 0.70 mmol) are added to DMF (5 mL), and the mixture is warmed to 95° C., followed by agitation for 16 hours. The reaction mixture is cooled, water (50 mL) is added thereto and the mixture is extracted with dichloromethane. The organic layer is separated and dried over $MgSO_4$. The solvent is removed under reduced pressure and the resultant product is subjected to liquid chromatography using dichloromethane/acetone (50:1) as an eluant to obtain a red solid compound (0.16 g, 53.3%). $^1$H-NMR (400 MHz, $CDCl_3$): δ=9.88 (s, 1H), 7.70 (m, 3H), 7.50 (m, 8H), 7.30 (m, 4H), 7.21 (d, 1H), 7.15 (m, 6H), 7.05 (d, 2H), 6.62 (dd, 2H), 6.53 (d, 2H), 3.42 (q, 8H), 1.22 (t, 12H).

Compound 103: Compound 23 (0.16 g, 0.18 mmol), cyanoacetic acid (0.16 g, 1.83 mmol) and peperidine (0.05 mL, 0.54 mmol) are added to dry chloroform (30 mL), followed by refluxing for 6 hours. The reaction mixture is cooled, water (50 mL) is added thereto and the mixture is extracted with chloroform. The organic layer is separated and dried over $MgSO_4$. The solvent is removed under reduced pressure and the resultant product is subjected to liquid chromatography using methanol/dichloromethane (1:5) as an eluant to obtain a red solid compound (0.14 g, 82.4%). $^1$H-NMR (400 MHz, DMSO, $d_6$): δ=8.04 (d, 4H), 7.93 (s, 1H), 7.60 (m, 4H), 7.44 (m, 10H), 7.02 (m, 6H), 6.68 (d, 2H), 6.51 (d, 2H), 3.47 (q, 8H), 1.25 (t, 12H).

Figure 4:
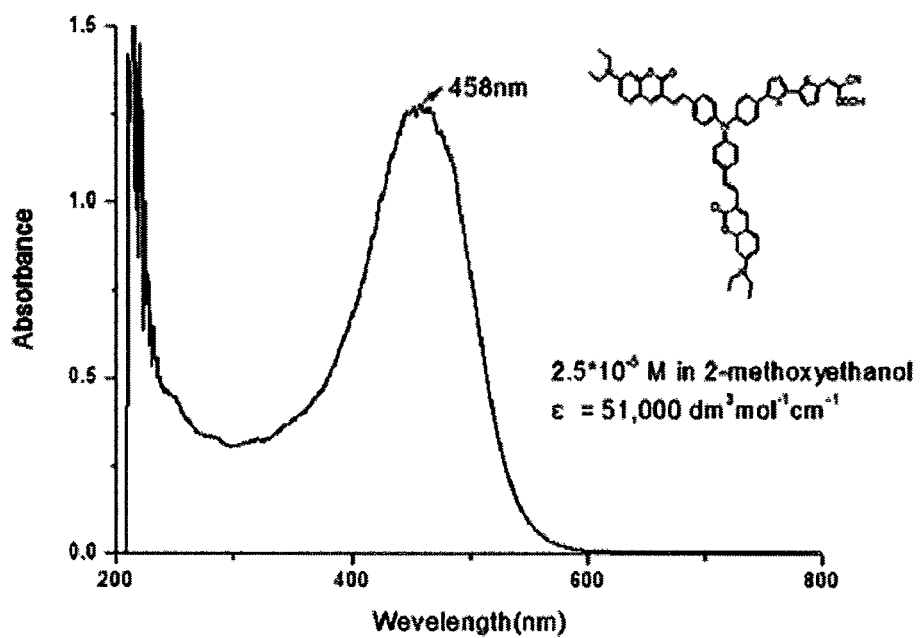
FIG. 4 is a graph showing the absorbance of the dye (Compound 103) obtained from Preparation Example 3.

Compound 103 is determined by UV-Vis absorption spectrometry at a concentration of $2.5 \times 10^{-5}$ M in 2-methoxyethanol as a solvent. The result is shown in FIG. 4 and Compound 103 has an absorbance of 51000 $dm^3\ mol^{-1}\ cm^{-1}$.

PREPARATION EXAMPLE 4

Preparation of Coumarin-Containing Dye (Compound 104)

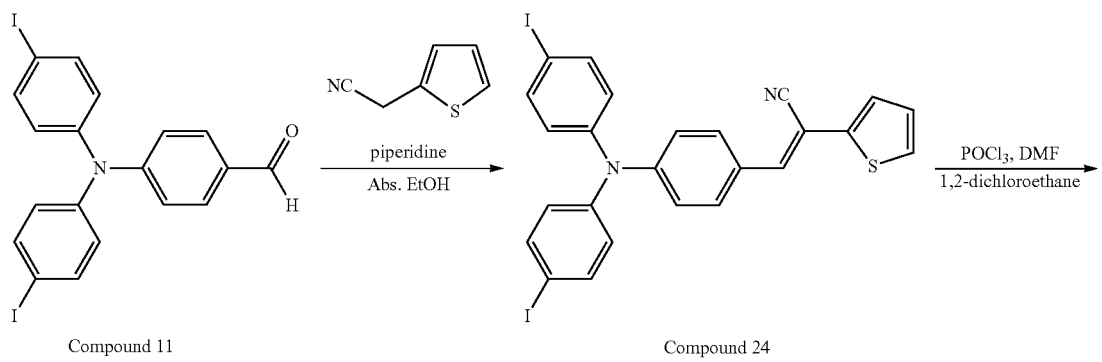

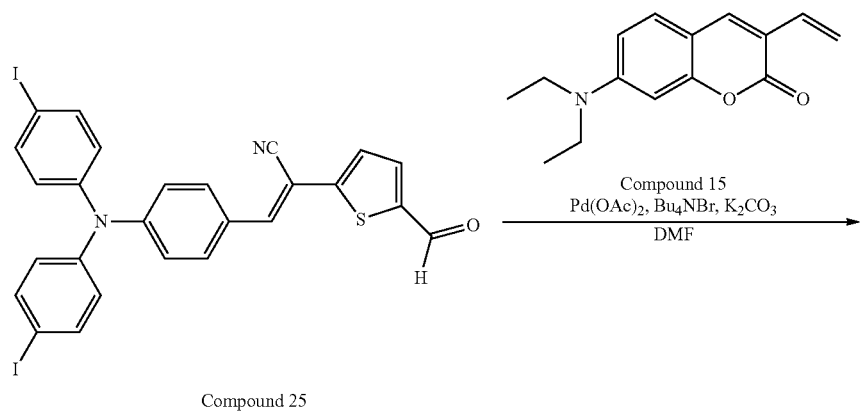

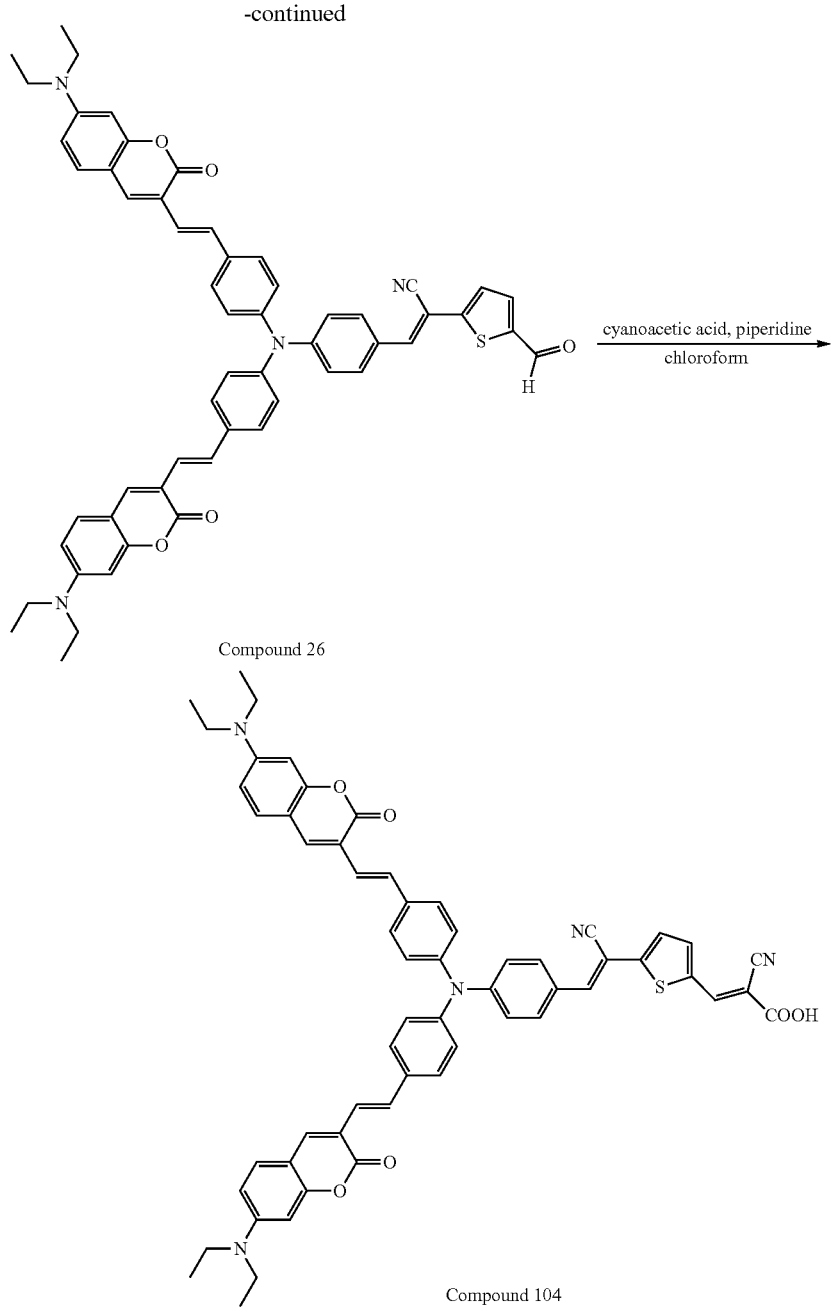

Compound 24: Compound 11 (1.20 g, 2.28 mmol), 2-thiophene acetonitrile (0.56 mL 6.84 mmol) and piperidine (0.68 mL 6.84 mmol) are added to absolute ethanol (5 mL), and the resultant mixture is refluxed for 8 hours. The reaction mixture is cooled, and then the solvent is removed under reduced pressure and the resultant product is subjected to liquid chromatography using dichloromethane/n-hexane (1:1) as an eluant to obtain a yellow solid compound (1.03 g, 71.5%). $^1$H-NMR (400 MHz, CDCl$_3$): δ=7.72 (d, J=8.4 Hz, 2H), 7.58 (d, J=8.4 Hz, 4H), 7.31 (s, 1H), 7.25 (m, 2H), 7.04 (m, 3H), 6.86 (d, J=8.4 Hz, 4H).

Compound 25: Compound 24 (1.0 g, 1.59 mmol), DMF (1.3 mL, 15.87 mmol) and POCl$_3$ (1.6 mL, 15.87 mmol) are added to 1,2-dichloroethane (20 mL) The mixture is agitated for 10 minutes at room temperature and is refluxed for 16 hours. The reaction mixture is cooled to room temperature and poured gradually to saturated aqueous sodium acetate solution, followed by agitation for 10 minutes. The mixture is extracted with dichloromethane to separate the organic layer therefrom, and the organic layer is dried over MgSO$_4$. The solvent is removed under reduced pressure and the resultant product is subjected to liquid chromatography using dichloromethane as an eluant to obtain a red solid compound (0.86 g, 81.1%). $^1$H-NMR (400 MHz, CDCl$_3$): δ=9.85 (s, 1H), 7.78 (d, J=8.4 Hz, 2H), 7.70 (d, J=4.0 Hz, 1H), 7.60 (d, J=8.4 Hz, 4H), 7.43 (s, 1H), 7.39 (d, J=4.0 Hz, 1H), 7.04 (d, J=8.4 Hz, 2H), 6.86 (d, J=8.4 Hz, 4H).

Compound 26: Compound 25 (0.48 g, 2.19 mmol), Compound 15 (0.48 g, 0.73 mmol), Pd(OAc)$_2$ (8 mg, 0.036 mmol), K$_2$CO$_3$ (0.35 g, 2.92 mmol) and Bu$_4$NBr (0.47 g, 1.46 mmol)

are added to DMF (5 mL), and the mixture is warmed to 95° C., followed by agitation for 16 hours. The reaction mixture is cooled, water (50 mL) is added thereto and the mixture is extracted with dichloromethane. The organic layer is separated and is dried over MgSO$_4$. The solvent is removed under reduced pressure and the resultant product is subjected to liquid chromatography using ethyl acetate/n-hexane (1:1) as an eluant to obtain a dark red solid compound (0.12 g, 52.5%). $^1$H-NMR (400 MHz, CDCl$_3$): δ=9.84 (s, 1H), 7.78 (d, J=8.8 Hz, 2H), 7.68 (d, J=4.0 Hz, 1H), 7.66 (s, 2H), 7.46 (m, 6H), 7.38 (d, J=4.0 Hz, 1H), 7.28 (d, J=8.8 Hz, 2H), 7.22 (s, 1H), 7.12 (d, J=8.4 Hz, 4H), 7.08 (d, J=8.8 Hz, 2H), 7.02 (d, J=16.0 Hz, 2H), 6.58 (dd, J=2.4 Hz, 2.4 Hz, 2H), 6.50 (d, J=2.4 Hz, 2H), 3.43 (q, 8H), 1.22 (t, 12H).

Compound 104: Compound 26 (0.18 g, 0.21 mmol), cyanoacetic acid (73 mg, 0.86 mmol) and peperidine (0.08 mL, 0.86 mmol) are added to dry chloroform (30 mL), followed by refluxing for 6 hours. The reaction mixture is cooled, water (50 mL) is added thereto and the mixture is extracted with chloroform. The organic layer is separated and dried over MgSO$_4$. The solvent is removed under reduced pressure and the resultant product is subjected to liquid chromatography using methanol/ethyl acetate (1:5) as an eluant to obtain a red solid compound (80 mg, 42.1%). $^1$H-NMR (400 MHz, DMSO, d$_6$): δ=8.04 (s, 2H), 7.87 (br, s, 2H), 7.80 (d, J=8.4 Hz, 2H), 7.52 (d, J=8.8 Hz, 4H), 7.47 (s, 1H), 7.44 (d, J=8.4 Hz, 4H), 7.08 (d, J=8.4 Hz, 4H), 7.06 (s, 1H), 7.02 (d, J=8.8 Hz, 4H), 6.70 (dd, J=2.4 Hz, 2.4 Hz, 2H), 6.54 (d, J=2.4 Hz, 2H), 3.47 (q, 8H), 1.25 (t, 12H).

Figure 5:
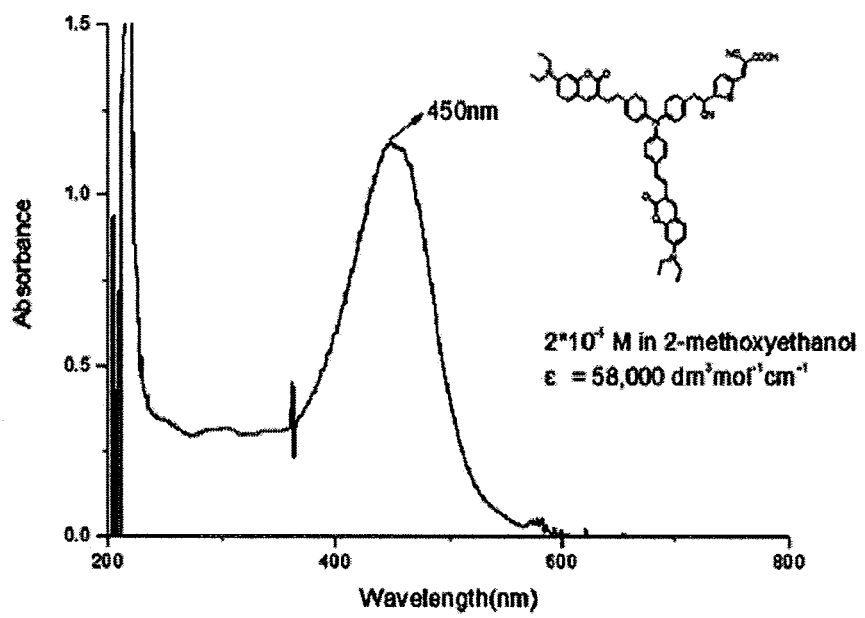
FIG. 5 is a graph showing the absorbance of the dye (Compound 104) obtained from Preparation Example 4.

Compound 104 is determined by UV-Vis absorption spectrometry at a concentration of 2×10$^{-5}$ M in 2-methoxyethanol as a solvent. The result is shown in FIG. 5 and Compound 104 has an absorbance of 58000 dm$^3$ mol$^{-1}$ cm$^{-1}$.

PREPARATION EXAMPLE 5

Preparation of Coumarin-Containing Dye (Compound 105)

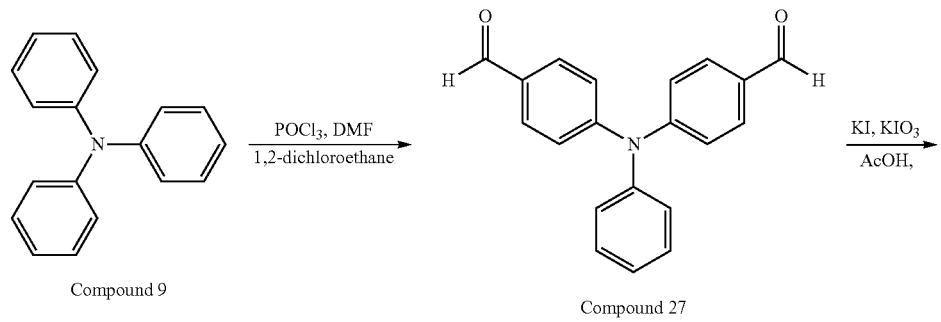

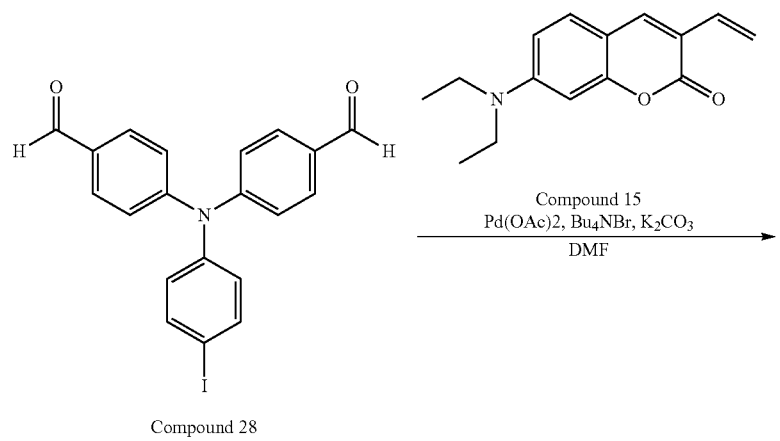

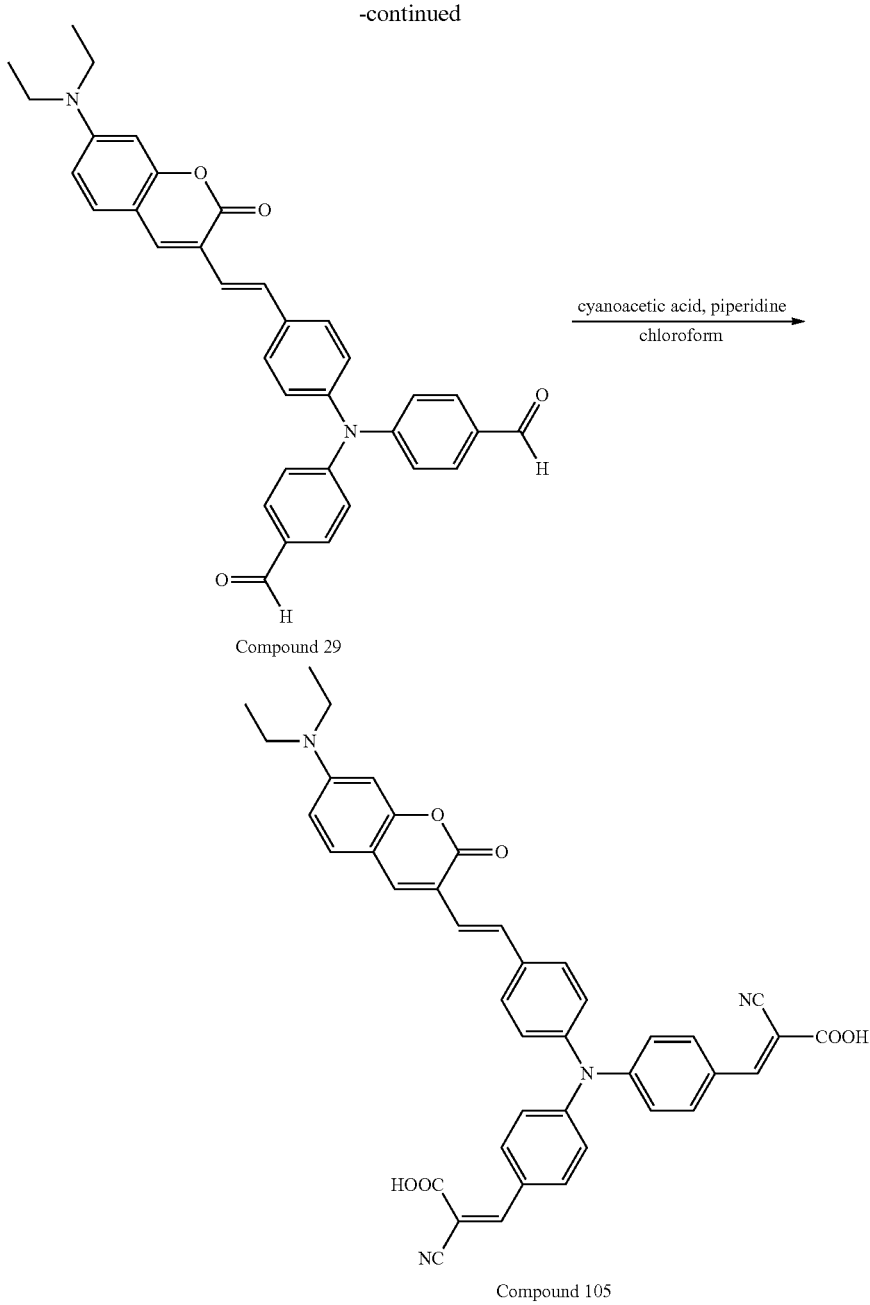

Compound 27: Triphenylamine (3.0 g, 12.23 mmol), DMF (9.5 mL, 122.3 mmol) and POCl$_3$ (11.4 mL, 122.3 mmol) are added to 1,2-dichloroethane (20 mL) The mixture is agitated for 1 hour at room temperature and is refluxed for 24 hours. The reaction mixture is cooled to room temperature and poured gradually to saturated aqueous sodium acetate solution, followed by agitation for 10 minutes. The mixture is extracted with dichloromethane to separate the organic layer therefrom, and the organic layer is dried over MgSO$_4$. The solvent is removed under reduced pressure and the resultant product is subjected to liquid chromatography using dichloromethane as an eluant to obtain a yellow solid compound (1.40 g, 38.0%). $^1$H-NMR (400 MHz, CDCl$_3$): δ=9.87 (s, 2H), 7.77 (d, J=8.4 Hz, 4H), 7.36 (m, 2H), 7.18 (m, 2H), 7.16 (m, 5H).

Compound 28: Compound 27 (1.0 g, 3.32 mmol) is added to glacial acetic acid (10 mL) and the mixture is warmed to 70° C. After the reaction mixture is observed to be dissolved completely, KI (0.55 g, 3.32 mmol) and KIO$_3$ (1.07 g, 4.98 mmol) are added thereto, followed by agitation for 16 hours. The reaction solution is cooled, and then the resultant solid is subjected to suction filtering and washed with water several times. The resultant product is dissolved into dichloromethane, washed with diluted ammonia solution (pH ~8), and then washed with saturated NaHSO$_3$ solution and water several times. The organic layer is dried over MgSO$_4$ and the solvent is removed under reduced pressure to obtain a pale yellow solid compound (1.33 g, 93.7%). $^1$H-NMR (400 MHz, CDCl$_3$): δ=9.88 (s, 2H), 7.78 (d, J=8.4 Hz, 4H), 7.66 (d, J=8.4 Hz, 2H), 7.15 (d, J=8.4 Hz, 4H), 6.90 (d, J=8.4 Hz, 2H).

Compound 29: Compound 28 (0.34 g, 1.55 mmol), Compound 15 (0.66 g, 1.55 mmol), Pd(OAc)$_2$ (17 mg, 0.077 mmol), K$_2$CO$_3$ (0.56 g, 4.65 mmol) and Bu$_4$NBr (0.75 g, 2.33 mmol) are added to DMF (5 mL), and the mixture is warmed to 95° C., followed by agitation for 4 hours. The reaction mixture is cooled, water (50 mL) is added thereto and the mixture is extracted with dichloromethane. The organic layer is separated and dried over MgSO$_4$. The solvent is removed under reduced pressure and the resultant product is subjected to liquid chromatography using ethyl acetate/n-hexane (1:1) as an eluant to obtain an orange solid compound (0.40 g, 50.0%). $^1$H-NMR (400 MHz, CDCl$_3$): δ=9.89 (s, 2H), 7.78 (m, 4H), 7.68 (s, 1H), 7.52 (d, J=8.8 Hz, 2H), 7.46 (m, 1H), 7.28 (d, J=9.2 Hz, 1H), 7.22 (m, 4H), 7.12 (m, 2H), 7.08 (d, J=16.0 Hz, 1H), 6.61 (dd, J=2.4 Hz, 2.4 Hz, 1H), 6.50 (d, J=2.4 Hz, 1H), 3.43 (q, 4H), 1.24 (t, 6H).

Compound 105: Compound 29 (0.30 g, 0.58 mmol), cyanoacetic acid (0.49 g, 5.78 mmol) and peperidine (0.17 mL, 1.73 mmol) are added to dry chloroform (30 mL), followed by refluxing for 16 hours. The reaction mixture is cooled, water (50 mL) is added thereto and the mixture is extracted with chloroform. The organic layer is separated and dried over MgSO$_4$. The solvent is removed under reduced pressure and the resultant product is subjected to liquid chromatography using methanol/dichloromethane (1:10) as an eluant to obtain an orange solid compound (0.16 g, 42.1%). $^1$H-NMR (400 MHz, DMSO, d$_6$): δ=8.02 (br, s, 1H), 7.92~7.80 (br, m, 6H), 7.56~7.40 (br, m, 5H), 7.20~7.00 (br, m, 6H), 6.68 (br, d, 1H), 6.52 (br, s, 1H), 3.47 (br, m, 4H), 1.25 (br, m, 6H).

Figure 6:
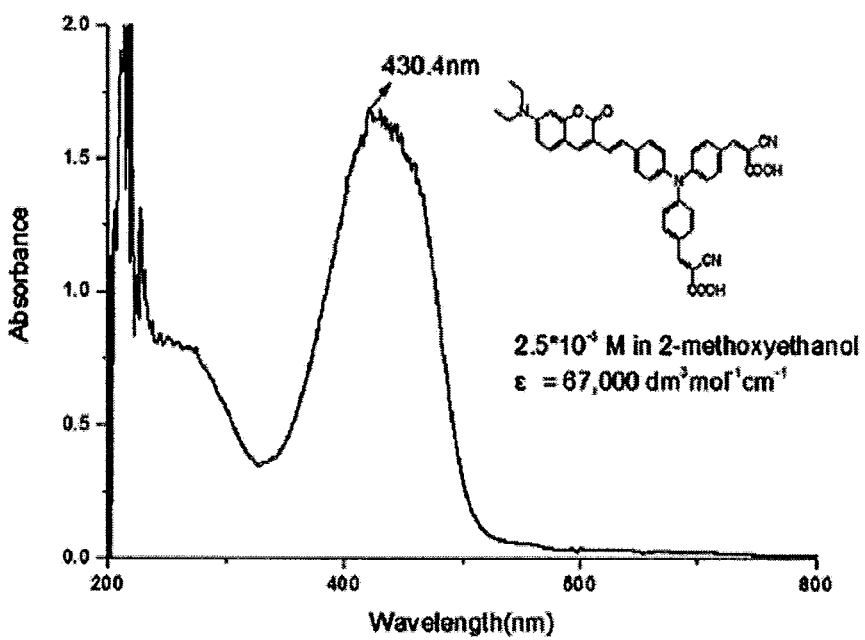
FIG. 6 is a graph showing the absorbance of the dye (Compound 105) obtained from Preparation Example 5.

Compound 105 is determined by UV-Vis absorption spectrometry at a concentration of 2.5×10$^{-5}$ M in 2-methoxyethanol as a solvent. The result is shown in FIG. 6 and Compound 105 has an absorbance of 67000 dm$^3$ mol$^{-1}$ cm$^{-1}$.

PREPARATION EXAMPLE 6

Preparation of Phenothiazine-Containing Dye (Compound 106)

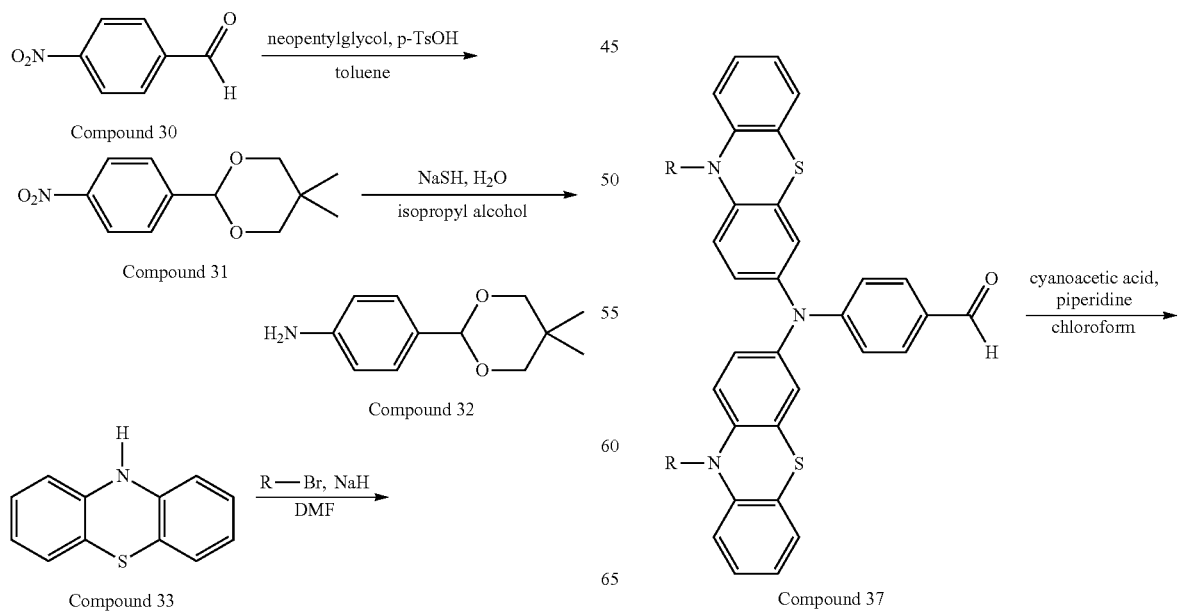

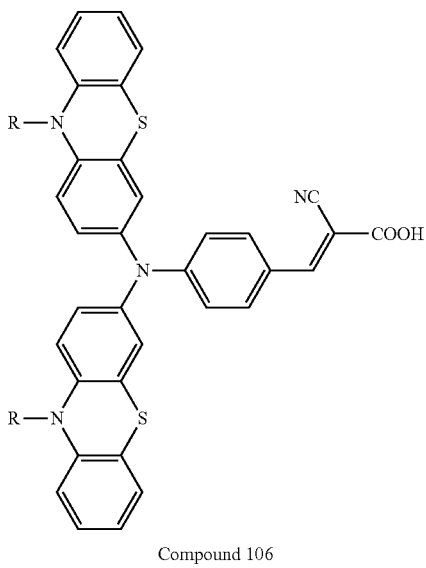

Compound 106

Compound 31: 4-Nitrobenzaldehyde (2.0 g, 13.23 mmol), neopentyl glycol (2.76 g, 26.46 mmol) and p-toluenesulfonic acid (50 mg) are added to toluene (50 mL). Then, a Dean-Stark trap is provided and the reaction mixture is refluxed for 16 hours. The reaction mixture is cooled, the solvent is removed under reduced pressure and the resultant product is subjected to liquid chromatography using dichloromethane as an eluant to obtain a yellow solid compound (2.90 g, 99.0%). $^1$H-NMR (400 MHz, CDCl$_3$): δ=8.20 (d, J=8.8 Hz, 2H), 7.66 (d, J=8.4 Hz, 2H), 5.45 (s, 1H), 3.78 (d, J=11.2 Hz, 2H), 3.66 (d, J=11.2 Hz, 2H), 1.28 (s, 3H), 0.82 (s, 3H).

Compound 32: Compound 31 (3.0 g, 13.56 mmol) is added to isopropyl alcohol (100 mL), a solution containing NaSH (6.03 g, 108.48 mmol) dissolved in water (5 mL) is added thereto, and the resultant mixture is refluxed for 16 hours. The reaction mixture is cooled, the solvent is removed under reduced pressure and the resultant product is washed with an excessive amount of water. The resultant solid is dissolved completely by adding ethyl acetate, and the resultant solution is poured to water (100 mL), followed by agitation for 10 minutes. The organic layer is separated and dried over MgSO$_4$. The solvent is removed under reduced pressure and the resultant product is subjected to liquid chromatography using ethyl acetate/n-hexane (1:3) as an eluant to obtain a yellow solid compound (2.13 g, 75.8%). $^1$H-NMR (400 MHz, CDCl$_3$): δ=7.24 (d, J=7.6 Hz, 2H), 7.60 (d, J=8.4 Hz, 2H), 5.26 (s, 1H), 3.70 (d, J=11.2 Hz, 2H), 3.66 (br, s, 2H), 3.58 (d, J=11.2 Hz, 2H), 1.28 (s, 3H), 0.76 (s, 3H).

Compound 34: Phenothiazine (Compound 33, 5.0 g, 25.09 mL) is added to DMF (20 mL), the temperature is decreased to 0° C. and 60% NaH (1.57 g, 37.64 mmol) is added thereto, followed by agitation for 10 minutes. Next, 1-bromohexane (4.23 mL, 30.11 mmol) is added to the reaction mixture, followed by agitation for 30 minutes. The reaction mixture is warmed to room temperature and agitated for 10 hours. Water (200 mL) is added to the reaction mixture and the mixture is extracted with dichloromethane. The organic layer is separated and dried over MgSO$_4$. The solvent is removed under reduced pressure and the resultant product is subjected to liquid chromatography using dichloromethane/n-hexane (1:3) as an eluant to obtain a colorless liquid compound (7.07 g, 99.4%). $^1$H-NMR (400 MHz, CDCl$_3$): δ=7.18 (m, 4H), 6.94 (m, 4H), 3.88 (t, 2H), 1.86 (m, 2H), 1.51 (m, 2H), 1.37 (m, 4H), 0.97 (t, 3H).

Compound 35: Compound 34 (4.18 g, 14.75 mmol) and NBS (2.63 g, 14.75 mmol) are added to DMF (20 mL) and the reaction mixture is agitated for 3 hours. Water (200 mL) is added to the reaction mixture and the mixture is extracted with dichloromethane. The organic layer is separated and dried over MgSO$_4$. The solvent is removed under reduced pressure and the resultant product is subjected to liquid chromatography using dichloromethane/n-hexane (1:5) as an eluant to obtain a brown liquid compound (4.05 g, 75.8%). $^1$H-NMR (400 MHz, CDCl$_3$): δ=7.18 (d, J=2.4 Hz, 1H), 7.12 (m, 1H), 7.08 (d, J=8.0 Hz, 1H), 6.89 (m, 1H), 6.82 (d, J=8.0 Hz, 1H), 6.64 (m, 2H), 3.77 (t, 2H), 1.75 (m, 2H), 1.37 (m, 2H), 1.28 (m, 4H), 0.86 (t, 3H).

Compound 36: Compound 32 (0.25 g, 1.21 mmol), Compound 35 (1.09 g, 3.0 mmol), Pd(OAc)$_2$ (11 mg, 0.05 mmol), P(tBu)$_3$ (0.03 mL) and NaOtBu (0.35 g, 1.63 mmol) are added to o-xylene (20 mL) and the resultant mixture is refluxed for 16 hours. The reaction mixture is cooled and filtered to remove the catalyst and byproducts. The solvent is removed under reduced pressure and the resultant product is subjected to liquid chromatography using dichloromethane/n-hexane (1:1) as an eluant to obtain a pale yellow liquid compound (0.39 g, 41.9%). $^1$H-NMR (400 MHz, CDCl$_3$): δ=7.24~7.14 (br, m, 2H), 7.08~6.94 (m, 5H), 6.92~6.56 (br, m, 11H), 5.24 (s, 1H), 3.72 (t, 4H), 3.66 (d, J=11.2 Hz, 2H), 3.54 (d, J=11.2 Hz, 2H), 1.70 (m, 4H), 1.33 (m, 4H), 1.21 (m, 11H), 0.79 (t, 6H), 0.74 (s, 3H).

Compound 37: Compound 36 (0.39 g, 0.51 mmol) and CF$_3$COOH (10 mL) are added to THF (150 mL) and water (50 mL), and the resultant mixture is agitated for 1 hour. The reaction mixture is neutralized with aqueous NaHCO$_3$ solution, and extracted with dichloromethane. The organic layer is separated and dried over MgSO$_4$. The solvent is removed under reduced pressure and the resultant product is subjected to liquid chromatography using dichloromethane as an eluant to obtain a yellow liquid compound (0.24 g, 68.6%). $^1$H-NMR (400 MHz, CDCl$_3$): δ=9.74 (s, 1H), 7.61 (d, J=8.8 Hz, 2H), 7.16 (m, 2H), 7.08 (d, J=8.4 Hz, 2H), 6.94~6.76 (m, 12H), 3.80 (t, 4H), 1.80 (m, 4H), 1.43 (m, 4H), 1.30 (m, 8H), 0.88 (t, 6H).

Compound 106: Compound 37 (0.24 g, 0.35 mmol), cyanoacetic acid (0.29 g, 3.50 mmol) and peperidine (0.1 mL, 1.05 mmol) are added to dry chloroform (30 mL), followed by refluxing for 16 hours. The reaction mixture is cooled, water (50 mL) is added thereto and the mixture is extracted with chloroform. The organic layer is separated and dried over MgSO$_4$. The solvent is removed under reduced pressure and the resultant product is subjected to liquid chromatography using methanol/chloroform (1:7) as an eluant to obtain an orange solid compound (0.23 g, 88.5%). $^1$H-NMR (400 MHz, DMSO, d$_6$): δ=8.11 (s, 1H), 7.90 (s, 1H), 7.71 (d, J=8.4 Hz, 2H), 7.15 (m, 2H), 7.04 (d, J=7.2 Hz, 2H), 6.96~6.84 (m, 9H), 6.81 (d, J=8.4 Hz, 2H), 3.81 (t, 4H), 1.73 (m, 4H), 1.41 (m, 4H), 1.28 (m, 8H), 0.85 (t, 6H).

Figure 7:
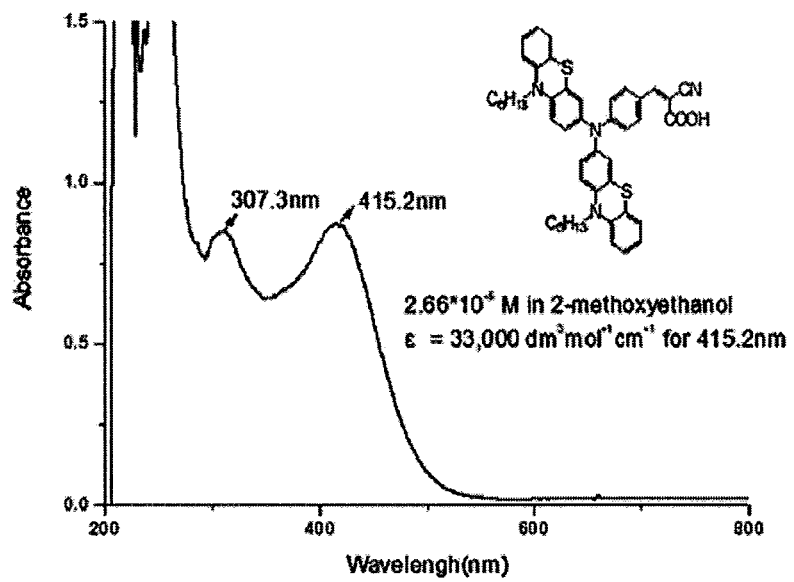
FIG. 7 is a graph showing the absorbance of the dye (Compound 106) obtained from Preparation Example 6.

Compound 106 is determined by UV-Vis absorption spectrometry at a concentration of $2.7 \times 10^{-5}$ M in 2-methoxyethanol as a solvent. The result is shown in FIG. 7 and Compound 106 has an absorbance of 33000 dm$^3$mol$^{-1}$cm$^{-1}$.

PREPARATION EXAMPLE 7

Preparation of Phenothiazine-Containing Dye (Compound 107)

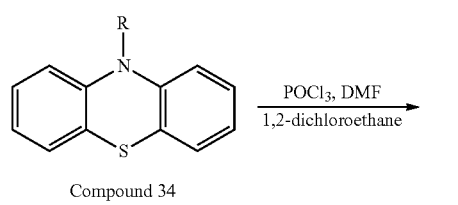

Compound 34

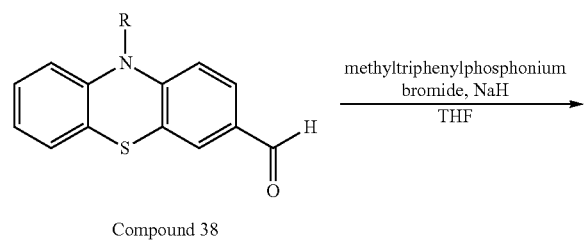

Compound 38

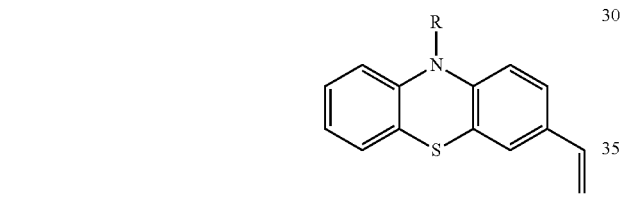

Compound 39

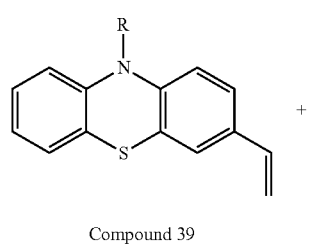

Compound 39

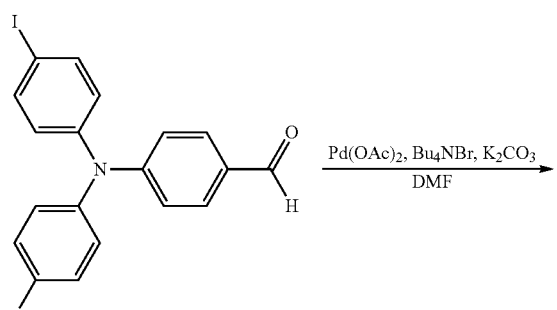

Compound 11

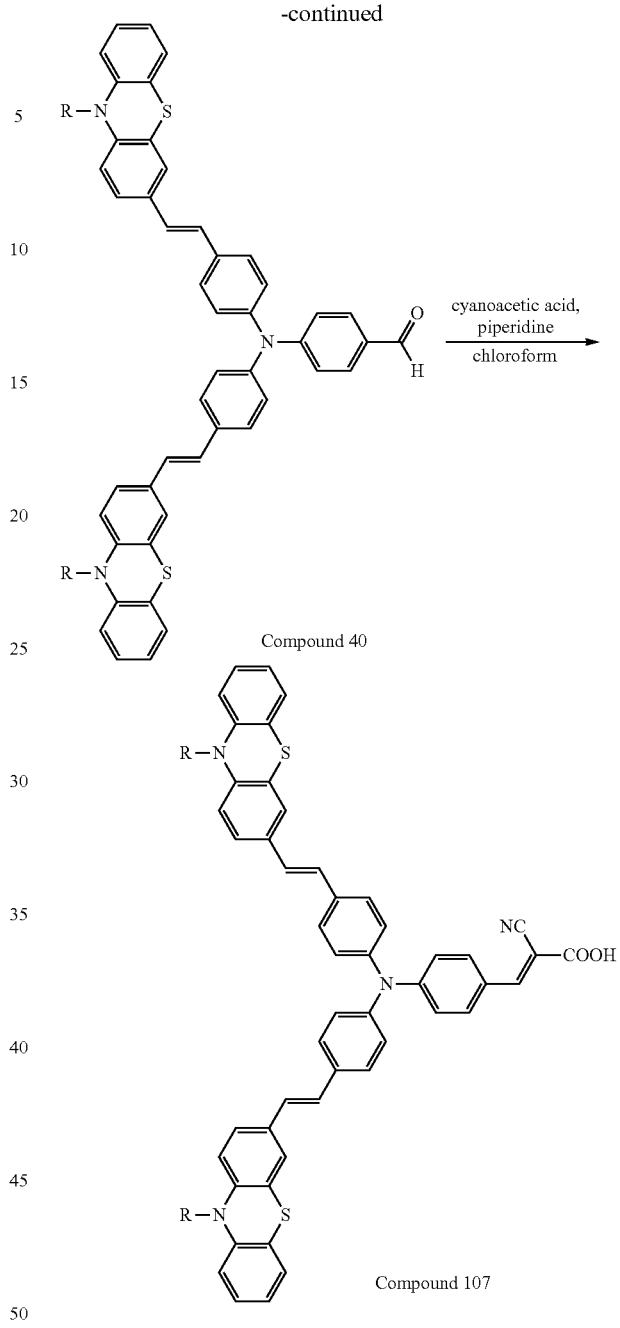

Compound 40

Compound 107

Compound 38: Compound 34 (7.07 g, 24.94 mmol), DMF (5.82 mL, 74.83 mmol) and POCl$_3$ (6.98 mL, 74.83 mmol) are added to 1,2-dichloroethane (30 mL). The mixture is agitated for 1 hour at room temperature and is refluxed for 2 hours. The reaction mixture is cooled to room temperature and poured gradually to saturated aqueous sodium acetate solution, followed by agitation for 10 minutes. The mixture is extracted with dichloromethane to separate the organic layer therefrom, and the organic layer is dried over MgSO$_4$. The solvent is removed under reduced pressure and the resultant product is subjected to liquid chromatography using dichloromethane/n-hexane (1:3) as an eluant to obtain a yellow liquid compound (5.72 g, 77.6%). $^1$H-NMR (400 MHz, CDCl$_3$): δ=9.77 (s, 1H), 7.61 (dd, J=2.4 Hz, 2.4 Hz, 1H), 7.56 (d, J=2.4 Hz, 1H), 7.16 (m, 1H), 7.08 (dd, J=2.4 Hz, 2.4 Hz, 1H), 6.93 (m, 1H), 6.89 (m, 2H), 3.87 (t, 2H), 1.79 (m, 2H), 1.42 (m, 2H), 1.32 (m, 4H), 0.87 (t, 3H).

Compound 39: Methyltriphenylphosphonium bromide (2.52 g, 7.08 mmol) and 95% NaH (0.21 g, 8.84 mmol) are added to THF (5 mL), followed by agitation for 1 hour. Compound 38 (1.74 g, 5.89 mmol) is added thereto and the mixture is agitated for 16 hours. Water (50 ml) is added to the reaction mixture and the mixture is extracted with dichloromethane to separate the organic layer. The organic layer is dried over MgSO$_4$ and the solvent is removed under reduced pressure. The resultant product is subjected to liquid chromatography using dichloromethane/n-hexane (1:3) as an eluant to obtain to obtain a pale yellow liquid compound (1.44 g, 78.5%). $^1$H-NMR (400 MHz, CDCl$_3$): δ=7.14 (d, J=2.4 Hz, 1H), 7.07 (m, 3H), 6.83 (m, 1H), 6.80 (d, J=8.4 Hz, 1H), 6.70 (d, J=8.0 Hz, 1H), 6.52 (dd, J=10.8 Hz, 10.8 Hz, 1H), 5.57 (d, J=17.6 Hz, 1H), 5.08 (d, J=10.8 Hz, 1H), 3.74 (t, 2H), 1.73 (m, 2H), 1.36 (m, 2H), 1.25 (m, 4H), 0.84 (t, 3H).

Compound 40: Compound 11 (0.19 g, 0.36 mmol) obtained from Preparation Example 1, Compound 39 (0.27 g, 0.87 mmol), Pd(OAc)$_2$ (4 mg, 0.018 mmol), K$_2$CO$_3$ (0.17 g, 1.44 mmol) and Bu$_4$NBr (0.23 g, 0.72 mmol) are added to DMF (5 mL), and the mixture is warmed to 95° C., followed by agitation for 6 hours. The reaction mixture is cooled, water (50 mL) is added thereto and the mixture is extracted with dichloromethane. The organic layer is separated and dried over MgSO$_4$. The solvent is removed under reduced pressure and the resultant product is subjected to liquid chromatography using dichloromethane/n-hexane (1:1) as an eluant to obtain a yellow solid compound (0.30 g, 93.8%). $^1$H-NMR (400 MHz, CDCl$_3$): δ=9.80 (s, 1H), 7.69 (d, J=8.8 Hz, 2H), 7.42 (d, J=8.4 Hz, 4H), 7.23 (m, 4H), 7.12 (m, 10H), 7.04 (m, 6H), 6.81 (dd, J=8.4 Hz, 8.4 Hz, 4H), 3.83 (t, 4H), 1.80 (m, 4H), 1.43 (m, 4H), 1.30 (m, 8H), 0.87 (t, 6H).

Compound 107: Compound 40 (0.30 g, 0.34 mmol), cyanoacetic acid (0.21 g, 3.37 mmol) and peperidine (0.1 mL, 1.01 mmol) are added to dry chloroform (30 mL), followed by refluxing for 4 hours. The reaction mixture is cooled, water (50 mL) is added thereto and the mixture is extracted with chloroform. The organic layer is separated and dried over MgSO$_4$. The solvent is removed under reduced pressure and the resultant product is subjected to liquid chromatography using methanol/chloroform (1:6) as an eluant to obtain an orange solid compound (0.24 g, 75.0%). $^1$H-NMR (400 MHz, DMSO, d6): δ=7.89 (s, 1H), 7.80 (d, J=8.8 Hz, 2H), 7.53 (d, J=8.8 Hz, 4H), 7.36 (m, 4H), 7.19~7.05 (m, 10H), 7.02~6.88 (m, 10H), 3.85 (t, 4H), 1.66 (m, 4H), 1.37 (m, 4H), 1.23 (m, 8H), 0.83 (t, 6H).

Figure 8:
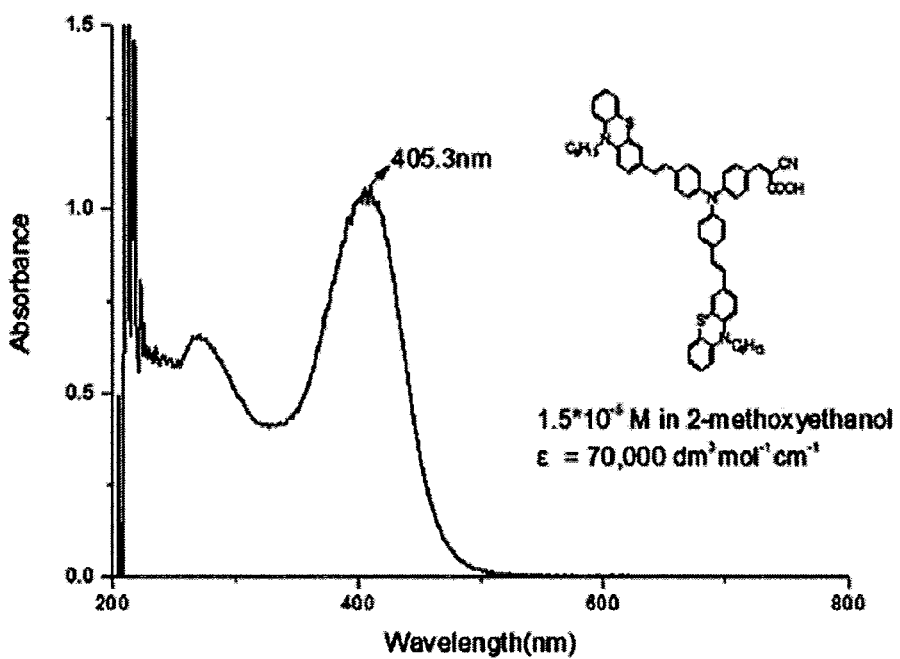
FIG. 8 is a graph showing the absorbance of the dye (Compound 107) obtained from Preparation Example 7.

Compound 107 is determined by UV-Vis absorption spectrometry and the absorption wavelength is shown in FIG. 8. The concentration is $1.5 \times 10^{-5}$ M in 2-methoxyethanol as a solvent. Compound 107 has an absorbance of at least 70,000 dm$^3$mol$^{-1}$cm$^{-1}$, which is significantly higher as compared to the existing dyes.

PREPARATION EXAMPLE 8

Preparation of Porphyrin-Containing Dye (Compound 108)

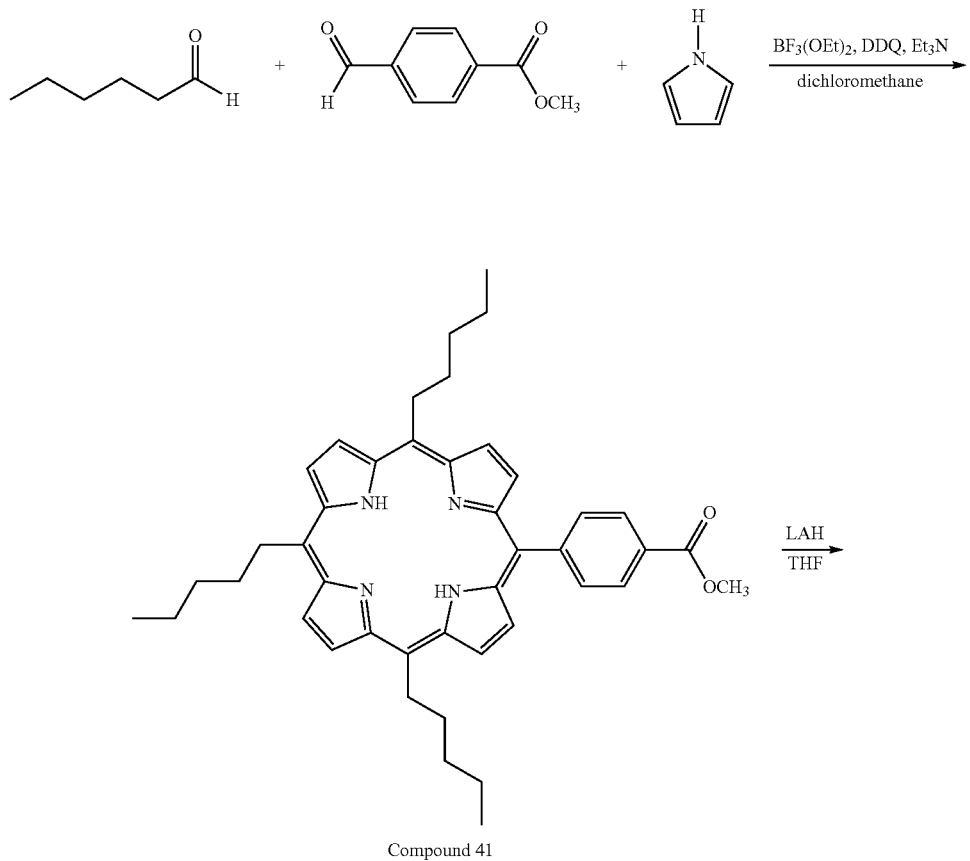

Compound 41

-continued
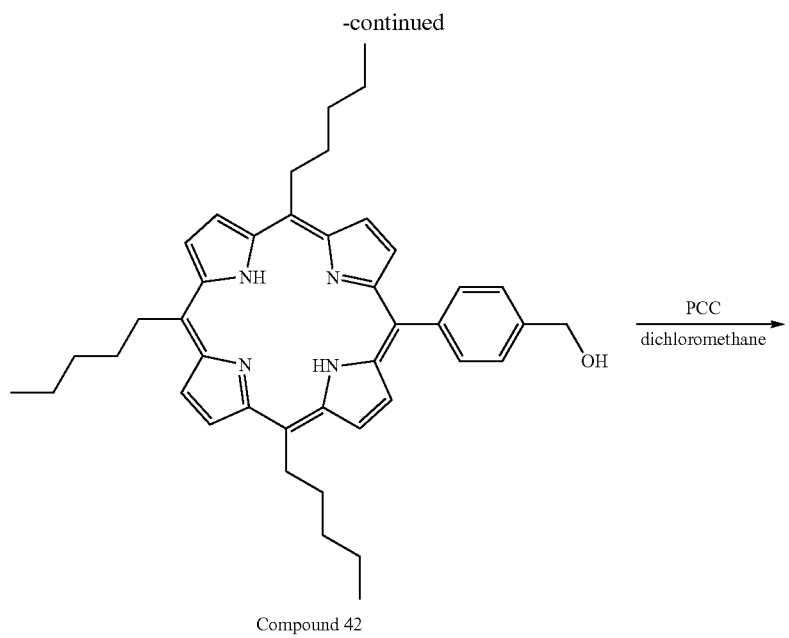
Compound 42
$\xrightarrow{\text{PCC}}_{\text{dichloromethane}}$
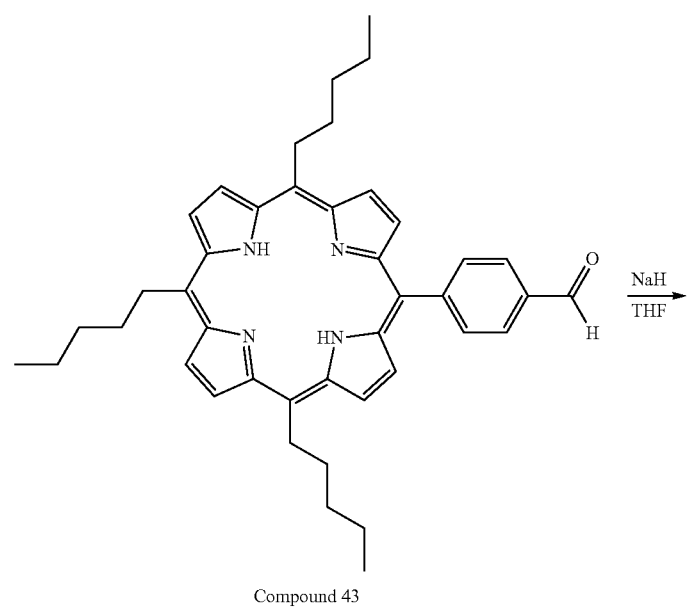
Compound 43
$\xrightarrow{\text{NaH}}_{\text{THF}}$ -continued
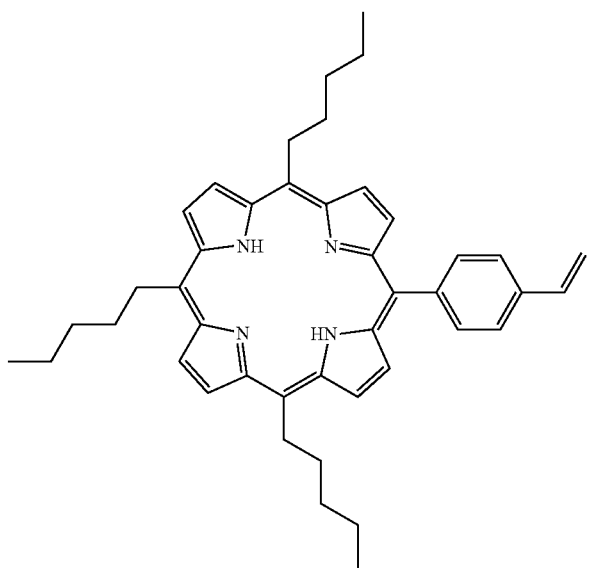
Compound 44
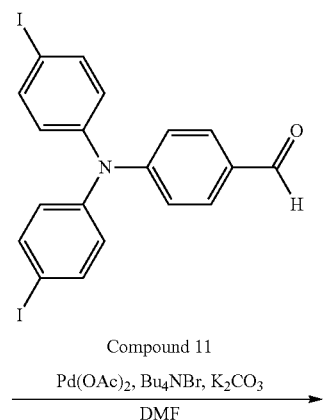
Compound 11
Pd(OAc)₂, Bu₄NBr, K₂CO₃
———————————————→
DMF
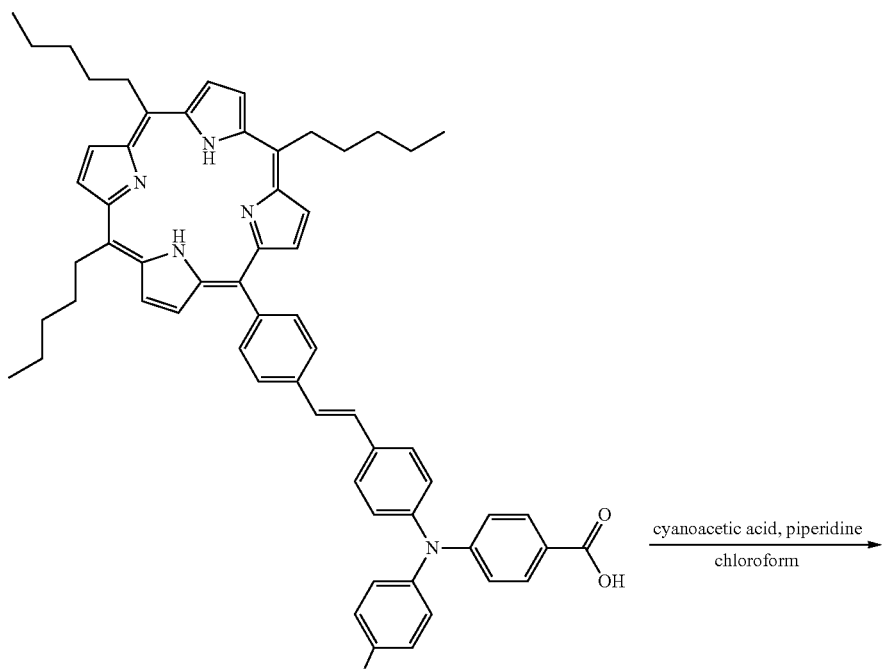
cyanoacetic acid, piperidine
————————————————→
chloroform

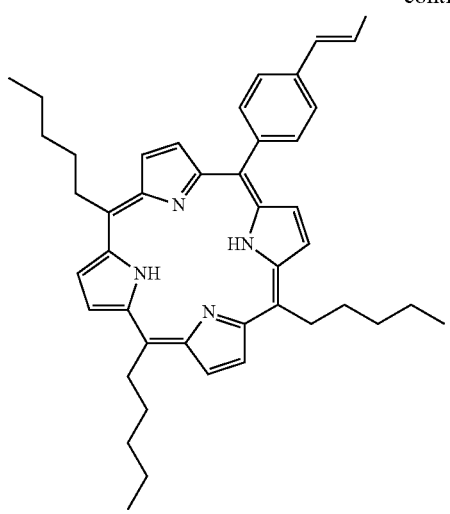
Compound 45
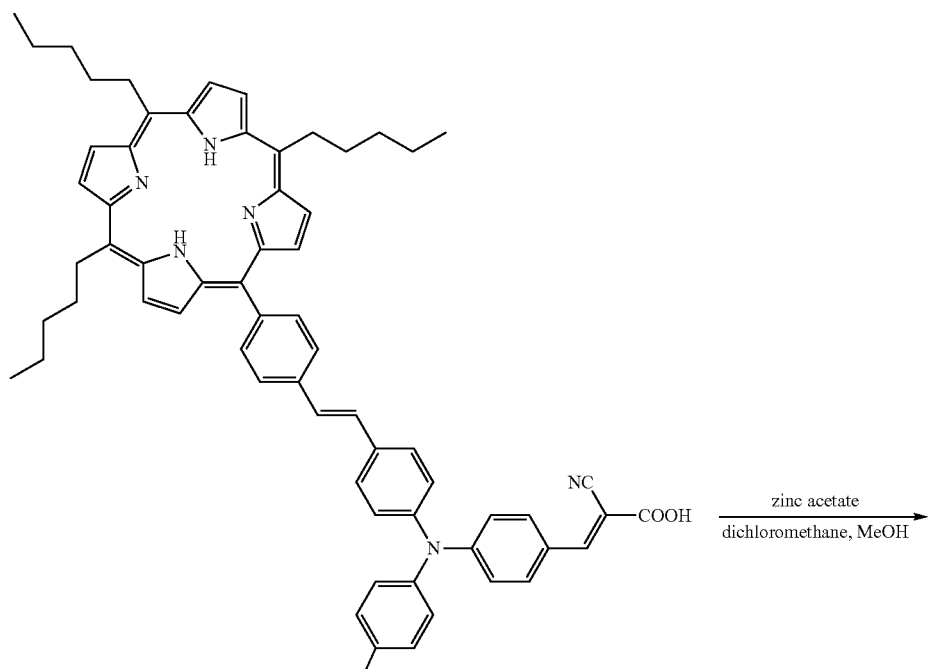

-continued
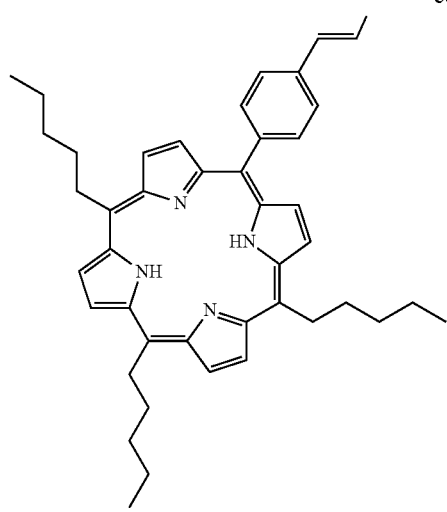
Compound 46
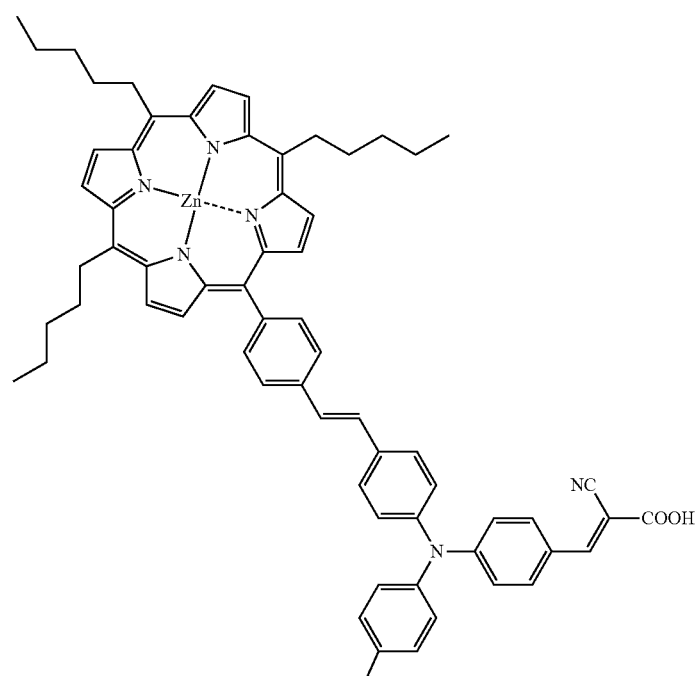

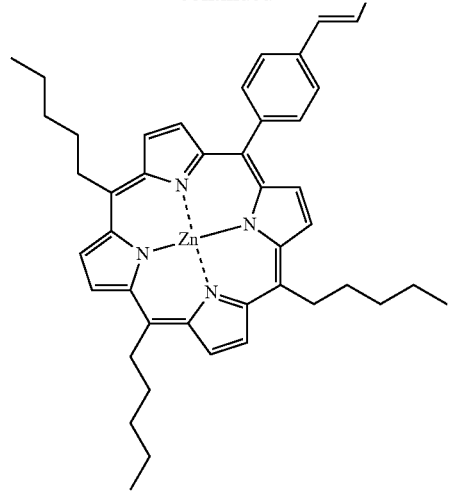

Compound 108

Compound 41: Under nitrogen atmosphere, hexanal (3.1 mL, 25 mmol), methyl-4-formyl benzoate (1.37 g, 8.35 mmol) and pyrrole (2.3 mL, 33.3 mmol) are dissolved into dichloromethane (3.3 L). Next, the resultant mixture is shielded from light. Then, boron trifluoride diethyl etherate ($BF_3 \cdot OEt_2$, 1.7 mL, 13.4 mmol) and 2-propanol (22 mL) are added thereto and the mixture is agitated for 90 minutes. Further, 2,3-dichloro-5,6-dicyani-1,4-benzoquinone (DDQ, 7.57 g, 33.3 mmol) are added and the mixture is agitated for 70 minutes. After adding triethyl amine (4.67 mL, 33.5 mmol), followed by agitation for 30 minutes, the reaction is completed. The solvent is removed via distillation under reduced pressure. The mixture is separated via liquid chromatography (silicagel, $CHCl_3$:hexane=3:1, $R_f$=0.17) to obtain a purple solid compound (0.438 g, 8%). TLC (dichloromethane) $R_f$=0.17, m.p.=222° C., $^1$H-NMR ($CDCl_3$, 400 MHz): δ(ppm)=−2.67(s, 2H), 0.98(m, 9H), 1.54(m, 6H), 1.77 (m, 6H), 2.52(m, 6H), 4.13(s, 3H), 4.95(m, 6H), 8.23(d, 2H), 8.40(d, 2H), 8.71(d, 2H), 9.36(d, 2H), 9.49(q, 4H).

Compound 42: Under nitrogen atmosphere, lithium aluminum hydride (34 mg, 0.916 mmol) is added to THF (20 mL), followed by agitation. After shielding light, Compound 41 (200 mg, 0.305 mmol) is added thereto, followed by agitation for 30 minutes. A small amount of water is added dropwise thereto and the reaction is completed. The mixture is extracted with dichloromethane. The resultant product is dried over anhydrous sodium sulfate and the solvent is removed via distillation under reduced pressure. The mixture is separated via liquid chromatography (silica gel, dichloromethane) to obtain a purple solid compound (182 mg, 95%). TLC (dichloromethane) $R_f$=0.12, m.p.=200° C., $^1$H-NMR ($CDCl_3$, 400 MHz): δ(ppm)=−2.67(s, 2H), 0.98(m, 9H), 1.54(m, 6H), 1.78(m, 6H), 2.52(m, 6H), 4.95(m, 6H), 5.04(d, 2H), 7.61(d, 2H), 8.13(d, 2H), 8.76(d, 2H), 9.34(d, 2H), 9.48(q, 4H).

Compound 43: Under nitrogen atmosphere, Compound 42 (500 mg, 0.79 mmol) is dissolved into dichloromethane (15 mL) after shielding light. The mixture is cooled to 0° C., pyridinium chlorochromate (PCC, 344 mg, 1.59 mmol) is added thereto. Next, the resultant mixture is agitated for 30 minutes at 0° C. and the reaction is completed. The mixture is extracted with dichloromethane and the solvent is removed via distillation under reduced pressure. The mixture is separated via liquid chromatography (silica gel, dichloromethane:hexane=1:1, $R_f$=0.76) to obtain Compound 43 (230 mg, 46%). TLC (dichloromethane:hexane=1:1) m.p.=148° C., $^1$H-NMR ($CDCl_3$, 400 MHz): δ(ppm)=−2.67(s, 2H), 0.98(m, 9H), 1.54(m, 6H), 1.78(m, 6H), 2.52(m, 6H), 4.95(m, 6H), 8.24(d, 2H), 8.33(d, 2H), 8.70(d, 2H), 9.37(d, 2H), 9.50(q, 4H), 10.36(s, 1H).

Compound 44: Under nitrogen atmosphere, sodium hydride (37 mg, 1.54 mmol) and methyl triphenyl phosphonium bromide (366 mg, 1.024 mmol) are added to purified THF (3 mL), followed by agitation for 10 minutes. After shielding light, Compound 43 (160 mg, 0.256 mmol) is added thereto and the mixture is agitated for 30 minutes. A small amount of water is added dropwise thereto and the reaction is completed. The solvent is removed via distillation under reduced pressure and the mixture is extracted with dichloromethane. The organic solvent is removed via further distillation under reduced pressure, and then the mixture is separated via liquid chromatography (silica gel, dichloromethane:hexane=1:3, $R_f$=0.18) to obtain Compound 44 (132 mg, 83%). TLC (dichloromethane:hexane=1:3) $R_f$=0.18, m.p.=99° C., $^1$H-NMR ($CDCl_3$, 400 MHz): δ(ppm)=−2.63(s, 2H), 0.99(m, 9H), 1.57(m, 6H), 1.80(m, 6H), 2.55(m, 6H), 4.96(m, 6H), 5.50(d, 2H), 6.08(d, 2H), 7.07(q, 1H), 7.78(d, 2H), 8.12(d, 2H), 8.81(d, 2H), 9.37(d, 2H), 9.50(q, 4H).

Compound 45: Under nitrogen atmosphere, Compound 11 obtained from Preparation Example 1 (120 mg, 0.19 mmol) and Compound 44 (40 mg, 0.077 mmol) are added to purified dimethylformamide (3 mL), after shielding light. The resultant mixture is agitated. Then, palladium (II) acetate (8 mg, 0.039 mmol), tetrabutylammonium bromide (TBAB, 62 mg, 0.19 mmol), anhydrous potassium carbonate ($K_2CO_3$, 56 mg, 0.462 mmol) are added thereto, and the resultant mixture is agitated at 95° C. for 15 hours. The mixture is extracted with dichloromethane. The resultant mixture is dried with anhydrous sodium sulfate and the reaction mixture is subjected to distillation under reduced pressure. The mixture is separated via liquid chromatography (silica gel, dichloromethane:hexane=1:1, $R_f$=0.26) to obtain Compound 45 (90 mg, 77%). TLC (dichloromethane:hexane=1:1) $R_f$=0.26, m.p.=>350° C., $^1$H-NMR ($CDCl_3$, 400 MHz): δ(ppm)=−2.60(s, 4H), 1.01 (m, 18H), 1.59(m, 12H), 1.80(m, 12H), 2.55(m, 12H), 4.95

(m, 12H), 7.23(d, 2H), 7.30(d, 4H), 7.44(s, 4H), 7.68(d, 4H), 7.80(d, 2H), 7.89(d, 4H), 8.17(d, 4H), 8.87(d, 4H), 9.38(d, 4H), 9.50(q, 8H), 9.90(s, 1H).

Compound 46: Under nitrogen atmosphere, Compound 45 (85 mg, 0.056 mmol) is dissolved into chloroform (3.5 mL) after shielding light. Next, cyanoacetic acid (47 mg, 0.56 mmol) and piperidine (0.026 mL, 0.28 mmol) are added thereto, followed by refluxing for 3 hours. The reaction mixture is extracted with chloroform and dried over anhydrous sodium sulfate. The solvent is removed via distillation under reduced pressure, and the mixture is separated via liquid chromatography (silica gel, dichloromethane:methanol=9:1, $R_f$=0.31) to obtain Compound 46 (73 mg, 82%). TLC (dichloromethane:methanol=9:1) $R_f$=0.31, m.p.=>350° C., $^1$H-NMR ((methyl sulfoxide)-$d_6$, 400 MHz): δ (ppm)=−2.60 (s, 4H), 1.01(m, 18H), 1.59(m, 12H), 1.80(m, 12H), 2.55(m, 12H), 4.95(m, 12H), 7.17(d, 2H), 7.30(d, 4H), 7.44(s, 4H), 7.68(d, 4H), 7.80(d, 2H), 7.89(d, 4H), 8.17(d, 4H), 8.87(d, 4H), 9.38(d, 4H), 9.50(q, 8H), 9.70(s, 1H).

Compound 108: Under nitrogen atmosphere, Compound 17 (70 mg, 0.046 mmol) is dissolved into dichloromethane/methanol (5:1, 10 mL) after shielding light. Next, zinc acetate (84 mg, 0.46 mmol) is added thereto and the mixture is agitated at room temperature for 1 hour. The mixture is extracted with dichloromethane and the solvent is removed via distillation under reduced pressure. The mixture is separated via liquid chromatography (silica gel, dichloromethane:methanol=9:1, $R_f$=0.31) to obtain Compound 108 (68 mg, 87%). TLC (dichloromethane:methanol=9:1) $R_f$=0.31, m.p.=>350° C., $^1$H-NMR ((methyl sulfoxide)-$d_6$, 400 MHz): δ(ppm)=−2.60(s, 4H), 1.01(m, 18H), 1.59(m, 12H), 1.80(m, 12H), 2.55(m, 12H), 4.95(m, 12H), 7.18(d, 2H), 7.30(d, 4H), 7.63(s, 4H), 7.82(d, 4H), 7.92(d, 2H), 8.05(d, 4H), 8.13(d, 4H), 8.77(d, 4H), 9.50(d, 4H), 9.60(q, 8H), 9.70(s, 1H).

Figure 9:
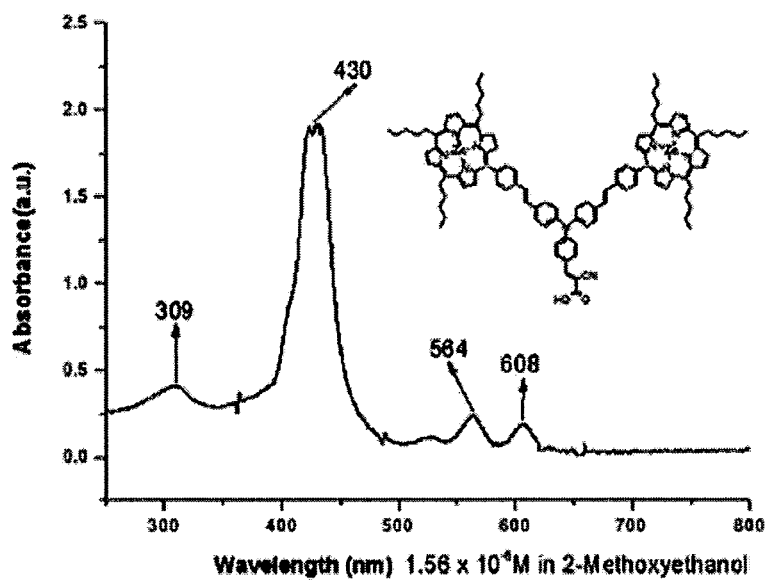
FIG. 9 is a graph showing the absorbance of the dye (Compound 108) obtained from Preparation Example 8.

Compound 108 is determined by UV-Vis absorption spectrometry at a concentration of $1.56 \times 10^{-5}$ M in 2-methoxyethanol as a solvent. The result is shown in FIG. 9. Compound 108 has an absorbance of 100,000 $dm^3 mol^{-1} cm^{-1}$ or higher at 430 nm. Such an absorbance is significantly higher as compared to the existing dyes.

PREPARATION EXAMPLE 9

Preparation of Coumarin-Containing Ruthenium Complex-Based Dye (Compound 109)

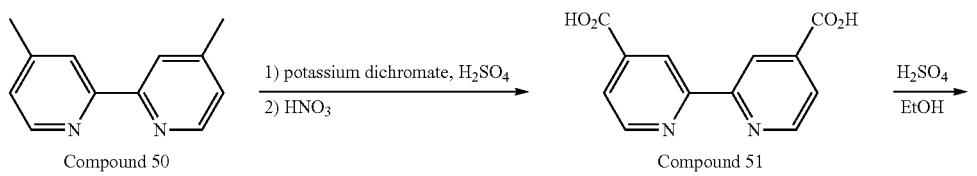

lp;3p

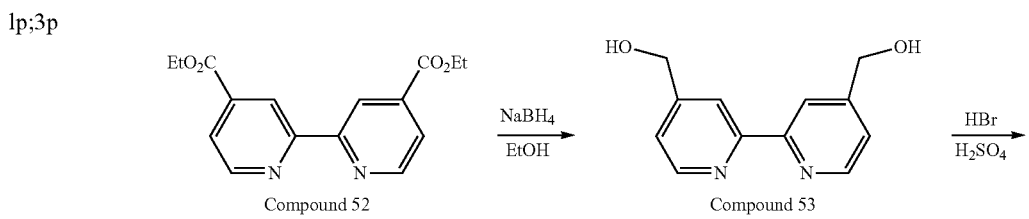

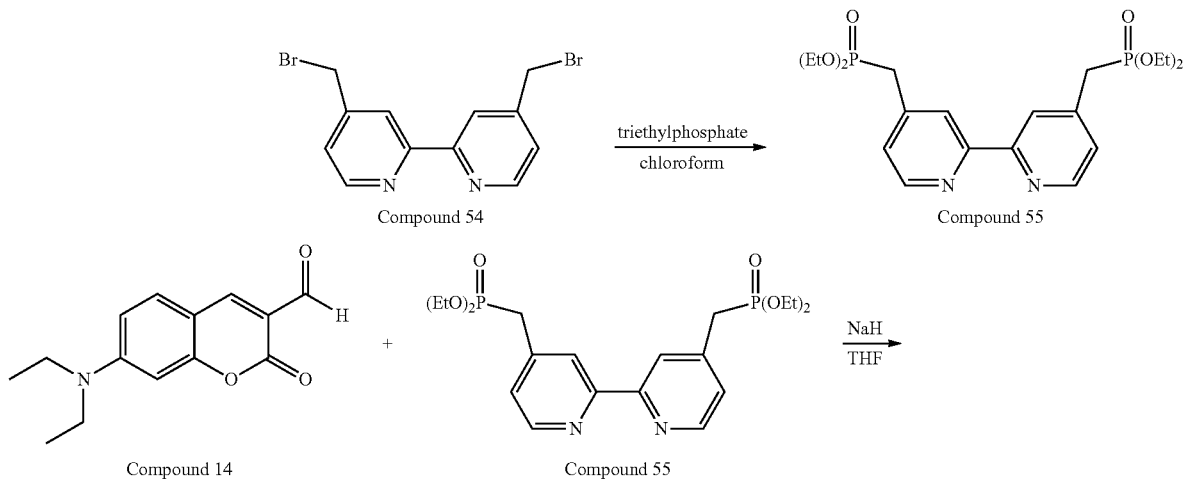

-continued

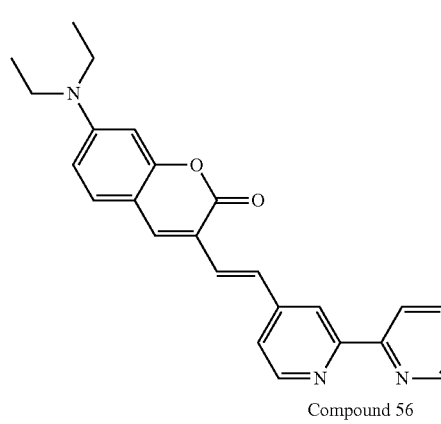
Compound 56

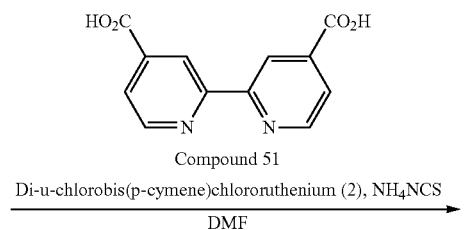
Compound 51
Di-u-chlorobis(p-cymene)chlororuthenium (2), NH₄NCS
———————————————————————→
DMF

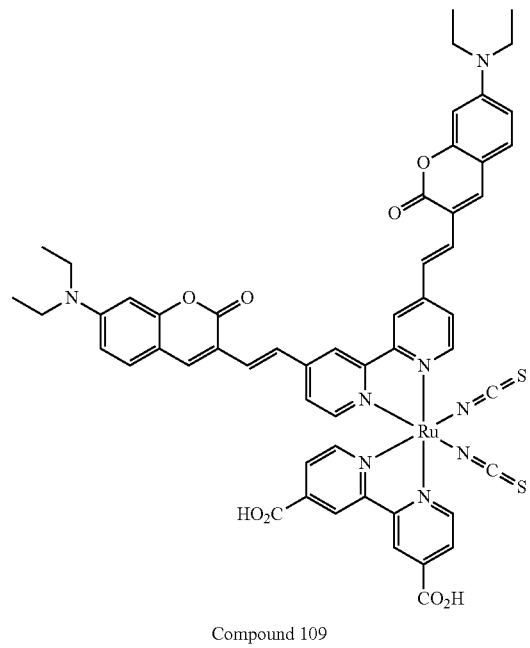
Compound 109

Compound 51: 4,4-Dimethyl-2,2'-bipyridine (Compound 50, 2.0 g, 10.0 mmol) is dissolved into concentrated sulfuric acid (50 mL) Next, potassium dichromate (9.6 g, 32.52 mmol) is added thereto, while maintaining the temperature not above 40° C. The reaction mixture is agitated for 30 minutes, and then the reaction is completed after observing that it turns into a dark green color. The reaction solution is added to ice water (800 mL) and the resultant solid is filtered and dried. The resultant pale yellow-colored solid is added to aqueous 50% $HNO_3$ solution, followed by refluxing for 4 hours. After the reaction mixture is poured into ice water (800 mL), the resultant solid is filtered and dried. Then, the dried solid is washed with methanol several times to obtain a white solid compound (2.4 g, 93.7%). m.p.>350° C. (dec.); $^1$H-NMR (400 MHz, $D_2SO_4$): δ=3.50 (d, 2H), 3.32 (s, 2H), 3.14 (d, 2H).

Compound 52: Compound 51 (1.0 g, 4.09 mmol) is added to absolute ethanol (80 mL), followed by agitation for 10 minutes. Next, concentrated sulfuric acid (1 mL) is added to the reaction mixture, followed by refluxing for 80 hours. The reaction mixture is cooled to room temperature and distilled water (80 mL) is added thereto. Then, the reaction mixture is neutralized with 1M aqueous sodium hydroxide solution. The resultant solid is filtered and dried to obtain a white solid compound (1.18 g, 95.0%). m.p. 161° C.; $^1$H-NMR (400 MHz, $CDCl_3$): δ=8.93 (s, 2H), 8.84 (d, J=8.8 Hz, 2H), 7.88 (d, J=8.8 Hz, 2H), 4.48 (q, 4H), 1.43 (t, 6H).

Compound 53: Compound 52 (1.1 g, 3.66 mmol) and sodium borohydride (2.77 g, 73.2 mmol) are added to absolute ethanol (70 mL) and the reaction mixture is refluxed for 3 hours. The reaction mixture is cooled to room temperature and ammonium chloride solution (3.8 g, 75.0 mmol) in distilled water (75 mL) is added thereto. The resultant white solid product is filtered and the solvent is removed under reduced pressure. Then, ethyl acetate is added thereto to dissolve the resultant solid completely. The organic layer is separated from the reaction mixture and dried over $MgSO_4$. The solvent is removed under reduced pressure to obtain a pale pink solid compound (0.69 g, 87.5%). m.p. 152° C.; $^1$H-NMR (400 MHz, acetone, $d_6$): δ=8.60 (d, J=8.8 Hz, 2H), 8.48 (s, 2H), 7.39 (d, J=8.8 Hz, 2H), 4.75 (s, 4H).

Compound 54: Compound 53 (0.69 g, 3.16 mmol) is dissolved into 48% HBr (15.5 mL) and concentrated sulfuric acid (5.1 mL), followed by refluxing for 6 hours. The reaction mixture is cooled and then distilled water (30 ml) is added thereto. Next, the reaction mixture is neutralized with 1M sodium hydroxide solution and the resultant pale pink solid product is filtered and dissolved into chloroform. The organic layer is separated and dried over MgSO$_4$. The solvent is removed under reduced pressure to obtain a pale pink solid compound (0.83 g, 76.0%). m.p. 172° C.; $^1$H-NMR (400 MHz, CDCl$_3$): δ=8.65 (d, J=8.8 Hz, 2H), 8.41 (s, 2H), 7.34 (d, J=8.8 Hz, 2H), 4.47 (s, 4H).

Compound 55: Compound 54 (0.83 g, 2.42 mmol) is dissolved completely into chloroform (6 mL), and triethyl phosphate (9 mL) is added to the reaction mixture, followed by refluxing for 3 hours. The reaction mixture is cooled and the solvent is removed under reduced pressure. The resultant product is subjected to liquid chromatography using ethyl acetate/methanol (10:1) as an eluant to obtain a white solid compound (1.08 g, 98.0%). m.p. 109° C.; $^1$H-NMR (400 MHz, CDCl$_3$): δ=8.57 (d, J=8.8 Hz, 2H), 8.30 (s, 2H), 7.31 (m, 2H), 4.03 (m, 8H), 3.22 (d, 4H), 1.26 (t, 12H).

Compound 56: Compound 55 (0.40 g, 0.88 mmol) and 95% NaH (64 mg, 2.62 mmol) are added to THF (10 mL) and the resultant mixture is agitated for 30 minutes. Next, Compound 14 (0.46 g, 2.10 mmol) obtained from Preparation Example 1 is added thereto, followed by agitation for 16 hours. Water (50 mL) is added to the reaction mixture and the mixture is extracted with chloroform to separate the organic layer, which, in turn, is dried over MgSO$_4$. The solvent is removed under reduced pressure and the resultant solid is washed with methanol to obtain an orange solid compound (0.25 g, 48.1%). $^1$H-NMR (400 MHz, CDCl$_3$): δ=8.93 (s, 2H), 8.66 (d, J=8.8 Hz, 2H), 7.87 (s, 2H), 7.67 (d, J=8.4 Hz, 4H), 7.50 (d, J=8.8 Hz, 2H), 7.35 (d, J=8.8 Hz, 2H), 6.02 (d, J=8.8 Hz, 2H), 6.50 (s, 2H), 3.38 (q, 8H), 1.20 (t, 12H).

Compound 109: Di-u-chlorobis(p-cymene)chlororuthenium (II) (91 mg, 0.149 mmol) and Compound 56 (176 mg, 0.298 mmol) are added to anhydrous DMF (5 mL), and the resultant mixture is agitated at 150° C. for 4 hours after shielding light. Next, Compound 14 (73 mg, 0.298 mmol) is added to the reaction mixture, followed by agitation for 4 hours. Then, NH$_4$NCS (170 mg, 2.245 mmol) is further added thereto, and the resultant mixture is agitated for 4 hours. The reaction mixture is cooled to room temperature and the solvent is removed under reduced pressure. The resultant product is acidified with aqueous nitric acid solution with pH ~3 and the resultant solid is filtered. The solid is washed with an excessive amount of water and dichloromethane several times, and then tetrabutylammonium hydroxide (1M in methanol, 0.1 mL) and a small amount of methanol are added thereto to dissolve the solid completely. The resultant product is subjected to liquid chromatography (Sephadex LH 20 gel) using methanol as an eluant, and the separation of the first band is repeated twice or three times. The solvent is removed under reduced pressure, and the resultant sold is washed with aqueous nitric acid solution (pH ~3) and distilled water to obtain a black solid compound (0.20 g, 61.0%). $^1$H-NMR (400 MHz, DMSO, d$_6$): δ=9.38 (s, 1H), 9.06~8.60 (m, 6H), 8.25~7.10 (m, 13H), 6.7~56.50 (m, 4H), 3.38 (q, 8H), 1.20 (t, 12H).

Figure 10:
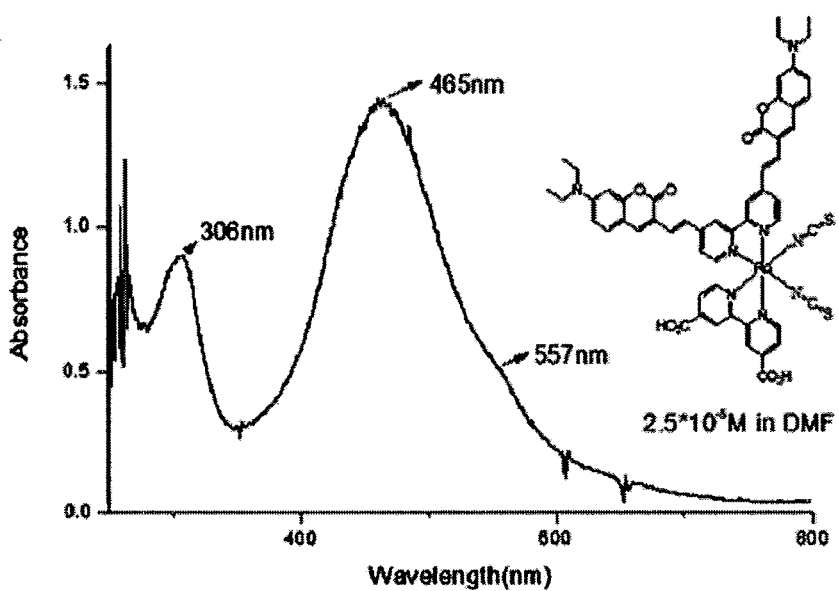
FIG. 10 is a graph showing the absorbance of the dye (Compound 109) obtained from Preparation Example 9.

To determine the absorbance of Compound 109 in the UV-Vis range, absorption spectrometry is carried out in DMF as a solvent at a concentration of $2.5 \times 10^{-5}$ M. The result is shown in FIG. 10. Compound 109 has a band edge at about 740 nm, and shows the absorption wavelength of coumarin structure at 465 nm and metal to ligand charge transfer (MLCT) band at 557 nm. The molar absorption coefficients (ϵ, M$^{-1}$ cm$^{-1}$) are calculated to 54,000 (465 nm) and 23,000 (557 nm), respectively. As shown in Table 1, when compared to the existing ruthenium complex salt-based dye, N719, Compound 109 has a significantly higher absorbance than N719, while the MLCT band shifts to the longer wavelength by about 43 nm. Such a high absorbance allows more effective light absorption when applied to solar cells. Therefore, it is possible to improve the photoelectric current conversion efficiency of a solar cell.

TABLE 1

| $\lambda_{max}(\epsilon)$ | 1 | 2 |
|---|---|---|
| N719 | 378(11,500) | 514(11,700) |
| Chemical Formula 3 | 465(54,000) | 557(23,000) |

PREPARATION EXAMPLE 10

Preparation of Phenothiazine-Containing Ruthenium Complex-Based Dye (Compound 110)

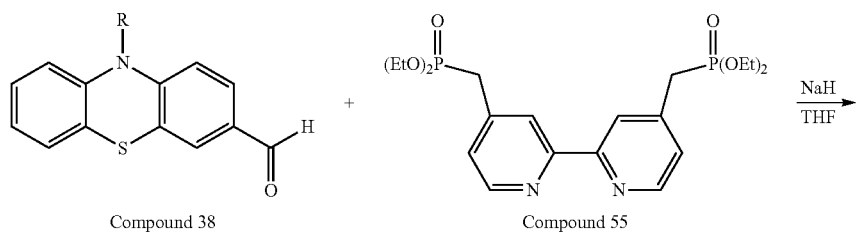

Compound 38    Compound 55

-continued

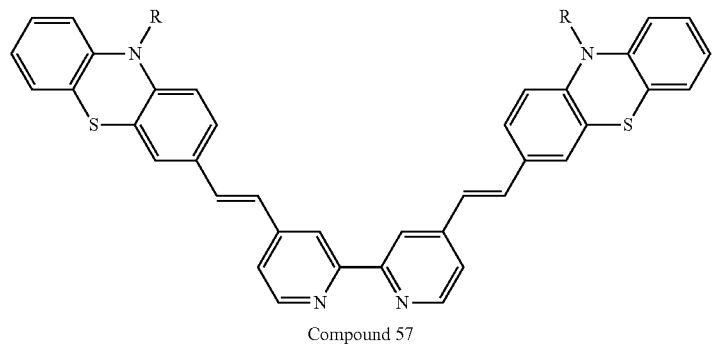

Compound 57

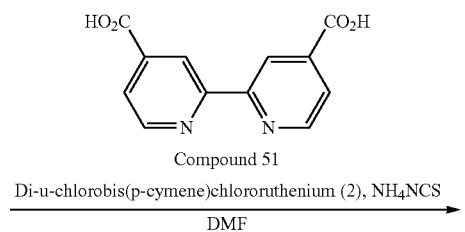

Compound 51

Di-u-chlorobis(p-cymene)chlororuthenium (2), NH4NCS
————————————————————→
DMF

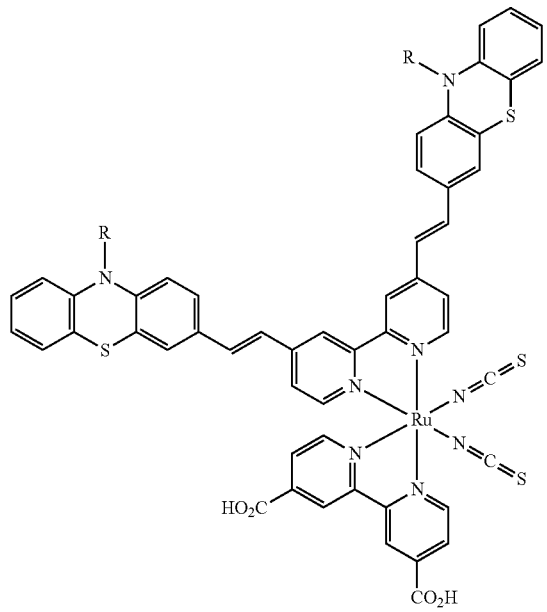

Compound 110

Compound 57: Compound 55 (0.20 g, 0.44 mmol) obtained from Preparation example 9 and 95% NaH (32 mg, 1.31 mmol) are added to THF (5 mL), followed by agitation for 1 hour. Compound 38 (0.33 g, 1.05 mmol) obtained from Preparation Example 7 is added thereto, followed by agitation for 16 hours. Then, water (50 mL) is added to the reaction mixture. The reaction mixture is extracted with chloroform to separate the organic layer and the organic layer is dried over MgSO$_4$. The solvent is removed under reduced pressure and the resultant solid is washed with methanol to obtain an orange solid compound (0.24 g, 70.6%). $^1$H-NMR (400 MHz, CDCl$_3$): δ=8.64 (d, J=8.8 Hz, 2H), 8.49 (s, 2H), 7.33 (m, 8H), 7.14 (m, 4H), 6.9~96.83 (m, 8H), 3.85 (t, 4H), 1.82 (m, 4H), 1.44 (m, 4H), 1.32 (m, 8H), 0.88 (t, 6H).

Compound 110: Di-u-chlorobis(p-cymene)chlororuthenium (II) (60 mg, 0.099 mmol) and Compound 57 (152 mg, 0.197 mmol) are added to anhydrous DMF (3 mL), and the resultant mixture is agitated at 150° C. for 4 hours after shielding light. Next, Compound 14 (49 mg, 0.197 mmol) is added to the reaction mixture, followed by agitation for 4 hours. Then, NH$_4$NCS (112 mg, 1.478 mmol) is further added thereto, and the resultant mixture is agitated for 4 hours. The reaction mixture is cooled to room temperature and the solvent is removed under reduced pressure. The resultant product is acidified with aqueous nitric acid solution with pH ~3 and the resultant solid is filtered. The solid is washed with an excessive amount of water and dichloromethane several times, and then tetrabutylammonium hydroxide (1M in methanol, 0.1 mL) and a small amount of methanol are added thereto to dissolve the solid completely. The resultant product is subjected to liquid chromatography (Sephadex LH 20 gel) using methanol as an eluant, and the separation of the first band is repeated twice or three times. The solvent is removed under reduced pressure, and the resultant sold is washed with aqueous nitric acid solution (pH ~3) and distilled water to obtain a dark red solid compound (0.20 g, 82.3%). $^1$H-NMR (400 MHz, DMSO, d$_6$): δ=9.34 (s, 1H), 9.06~8.60 (m, 5H), 8.50 (br, s, 1H), 8.12 (br, s, 1H), 8.06 (br, s, 1H), 7.87~7.40 (m, 10H), 7.30~6.90 (m, 10H), 3.88 (m, 4H), 3.16 (m, 4H), 1.56 (m, 4H), 1.30 (m, 8H), 0.93 (t, 6H).

To determine the absorbance of Compound 110 in the UV-Vis range, absorption spectrometry is carried out in DMF as a solvent at a concentration of $1.25 \times 10^{-5}$ M. The result is shown in FIG. 11.

Figure 11:
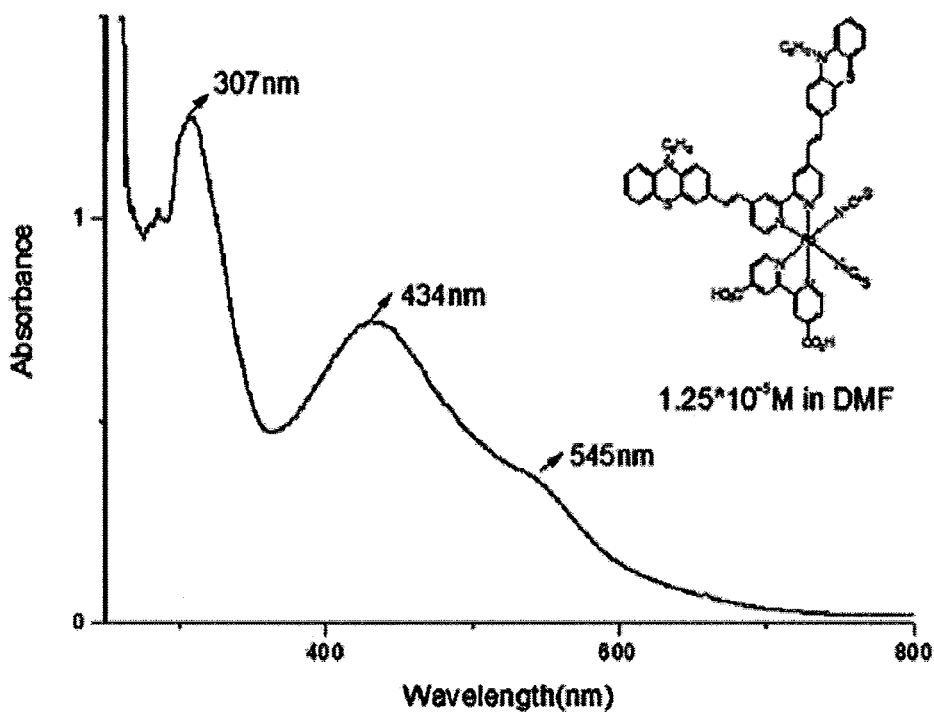
FIG. 11 is a graph showing the absorbance of the dye (Compound 110) obtained from Preparation Example 10.
Figure 12:
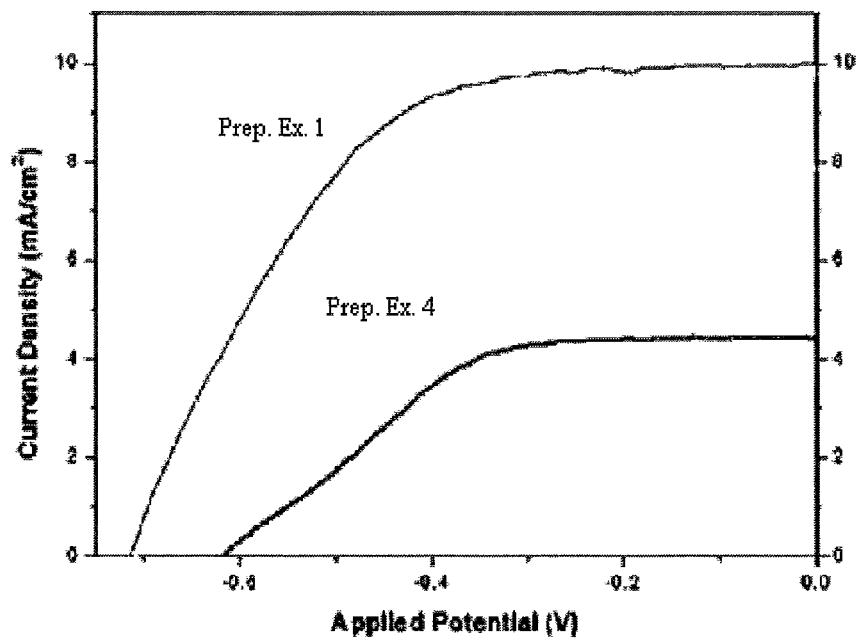
FIG. 12 is a current-voltage curve of a solar cell using Compounds 101 and 104.
Figure 13:
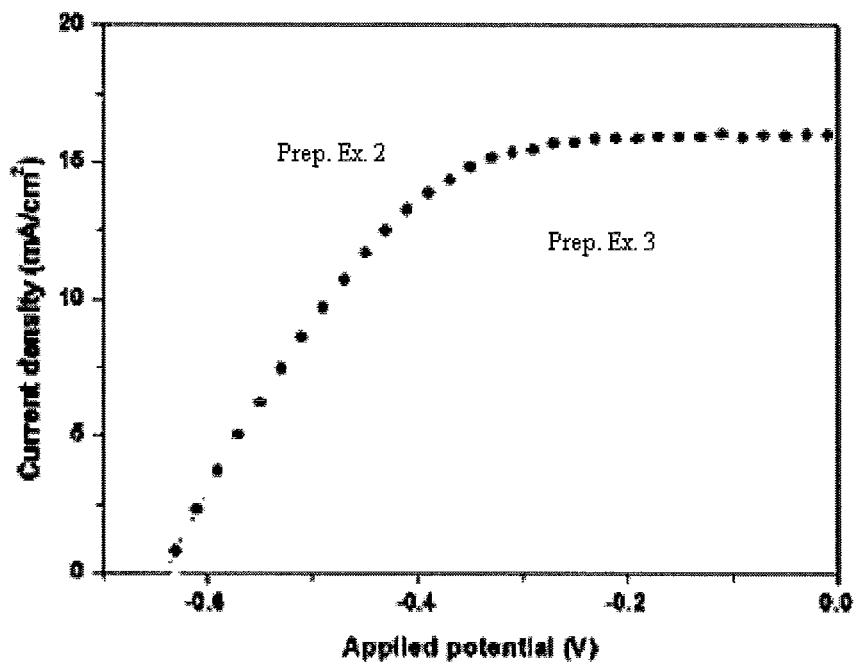
FIG. 13 is a current-voltage curve of a solar cell using Compounds 102 and 103.
Figure 14:
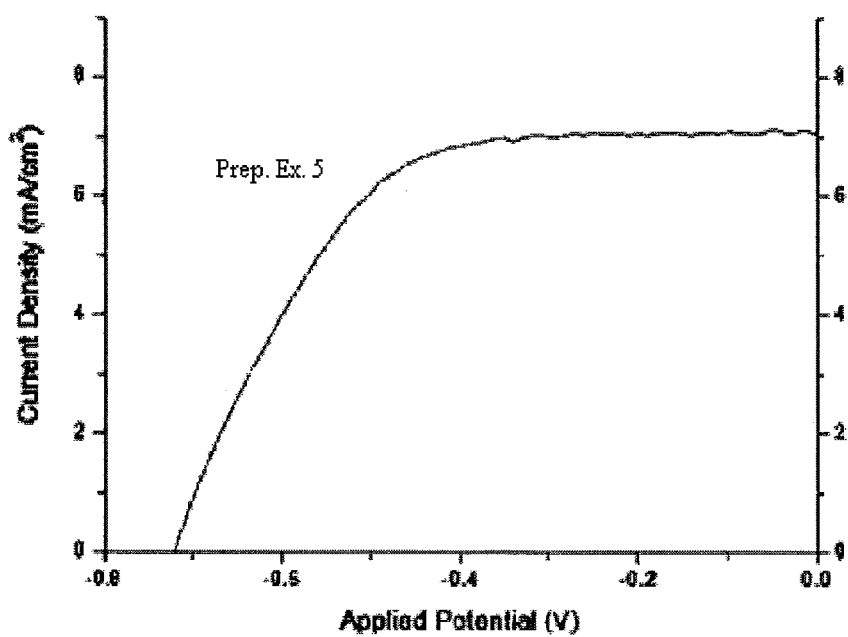
FIG. 14 is a current-voltage curve of a solar cell using Compound 105.
Figure 15:
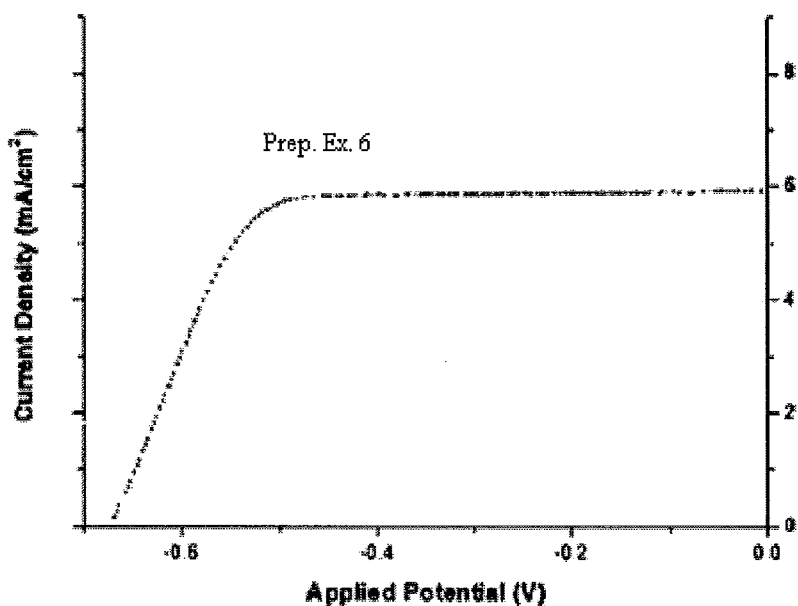
FIG. 15 is a current-voltage curve of a solar cell using Compound 106.
Figure 16:
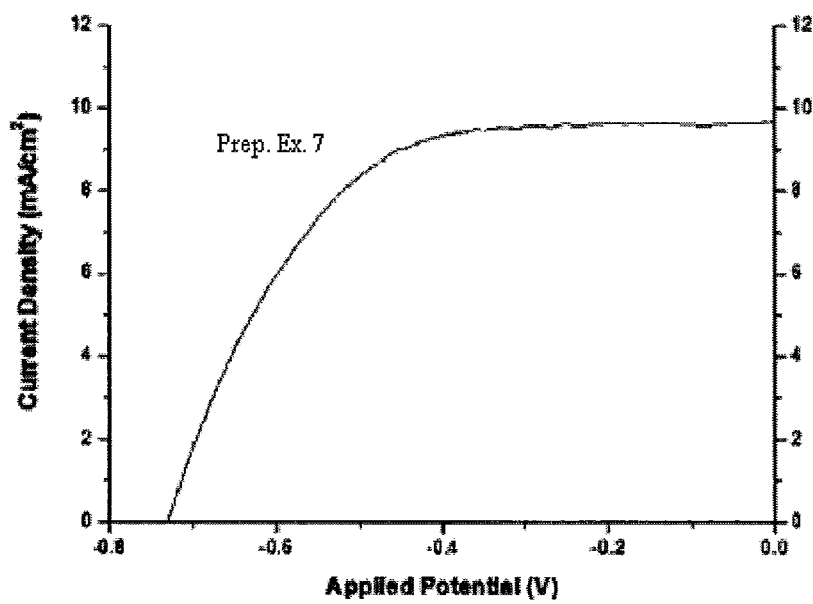
FIG. 16 is a current-voltage curve of a solar cell using Compound 107.
Figure 17:
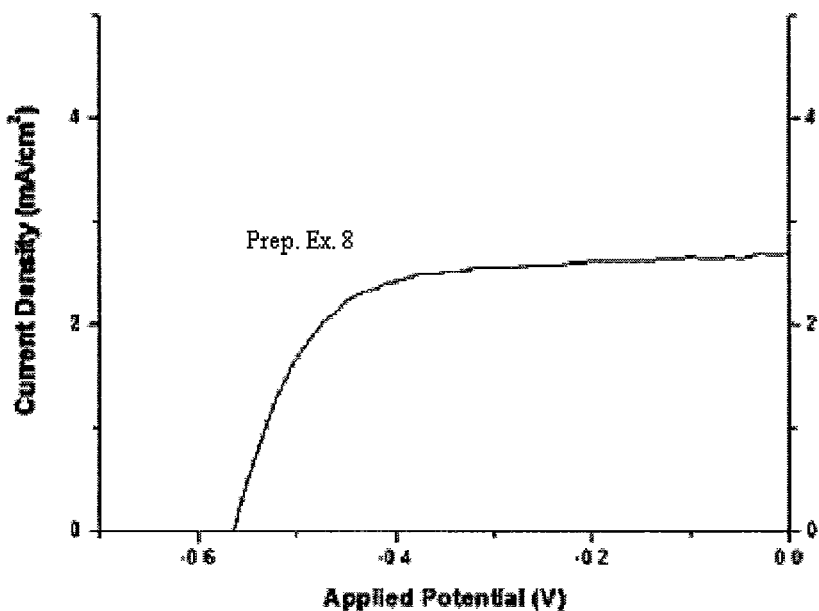
FIG. 17 is a current-voltage curve of a solar cell using Compound 108.
Figure 18:
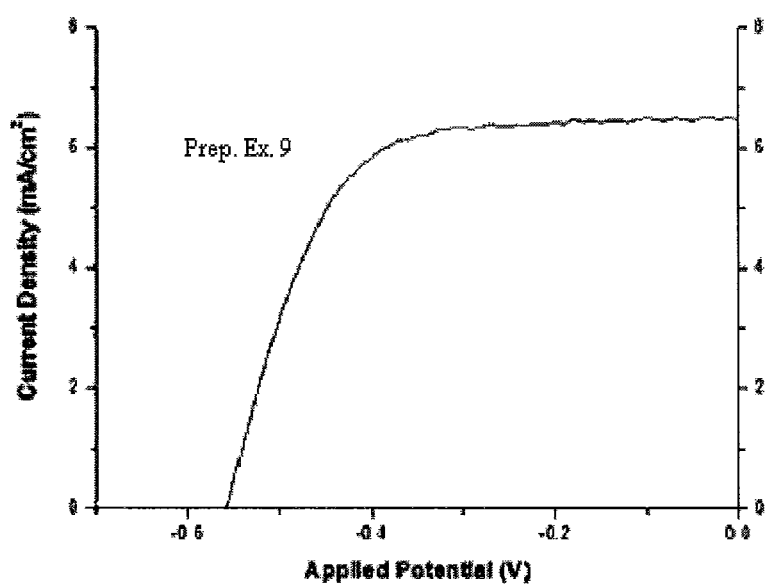
FIG. 18 is a current-voltage curve of a solar cell using Compound 109.
Figure 19:
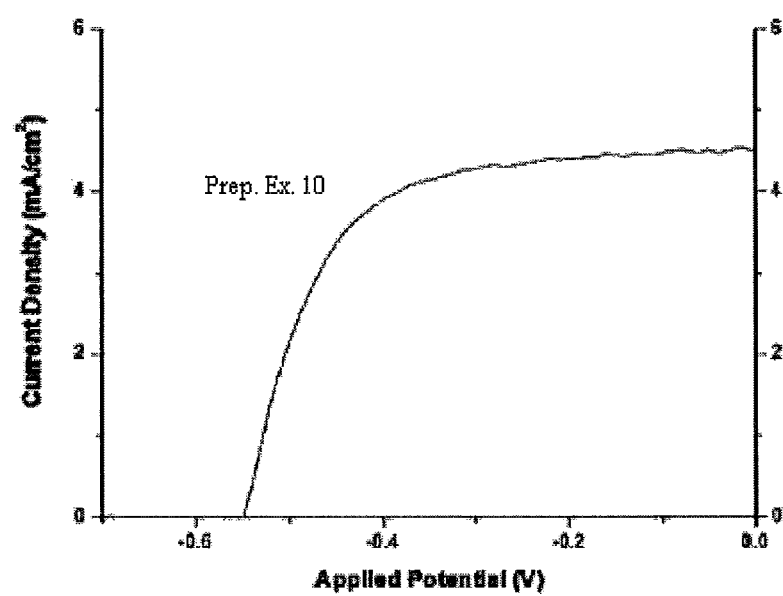
FIG. 19 is a current-voltage curve of a solar cell using Compound 110.

Referring to FIG. 11, Compound 110 has a band edge at about 740 nm, and shows the maximum absorption wavelength at 307 nm, an absorption wavelength of phenothiazine structure at 434 nm and MLCT band at 545 nm. The molar absorption coefficients (ε, $M^{-1}cm^{-1}$) are calculated to 100,000 (307 nm), 59,000 (434 nm) and 28,000 (545 nm), respectively. As shown in Table 2, when compared to the existing ruthenium complex salt-based dye, N719, Compound 110 has a significantly higher absorbance than N719, while the MLCT band shifts to the longer wavelength by about 30 nm. Such a high absorbance allows more effective light absorption when applied to solar cells. Therefore, it is possible to improve the photoelectric current conversion efficiency of a solar cell.

TABLE 2

| $\lambda_{max}(\epsilon)$ | 1 | 2 | 3 |
|---|---|---|---|
| N719 | 309(46,400) | 378(11,500) | 514(11,700) |
| Chemical Formula 3 | 307(100,000) | 434(59,000) | 545(28,000) |

The dyes for dye-sensitised solar cells according to Preparation Examples 1 to 10 have a high absorbance, which is at least five times the absorbance of the existing dye (N719). Therefore, the dyes are capable of improving photoelectric current conversion efficiency when applied to dye-sensitised solar cells.

EXAMPLE 1

Manufacture of Dye-Sensitised Solar Cell

Manufacture of Solar Cell Device and Characterization Thereof.

(1) Manufacture of Working Electrode

Fluorine-doped tin oxide (FTO) coated conduction glass (Pilkington, TEC7) is cut into a size of 1.5 cm×1.5 cm and subjected to sonication in soap water for 5 minutes. Then, the soap water is removed completely, and the glass is further subjected to sonication in ethanol three times, each for 5 minutes. Next, the glass is rinsed completely with anhydrous ethanol and dried in an oven. The thus prepared FTO glass is coated with 0.2M titanium (IV) butoxide solution via a spin coating process in order to improve the contact with $TiO_2$, and the solvent is dried completely in an oven.

Then, Dyesol's titania ($TiO_2$) is coated on the FTO glass via a doctor blade process. The coated film is dried in an oven at 100° C. for 10 minutes and heat treated at 450° C. for 30 minutes to obtain a $TiO_2$ film with a thickness of 10 micrometers. The heat treated $TiO_2$ film is dipped into 0.5 mM solution of the dye in anhydrous ethanol for 24 hours to allow adsorption of the dye. (When the dye is not dissolved into anhydrous ethanol, any solvent capable of dissolving the dye is used). After the adsorption, the non-adsorbed dye is washed completely with anhydrous ethanol, followed by drying. The film, onto which the dye is adsorbed, is scraped off except an area of 4 mm×4 mm.

(2) Manufacture of Counter Electrode

Two holes for the injection of an electrolyte are perforated through FTO glass with a size of 1.5 cm×1.5 cm by using a diamond drill (Bosch Dremel multipro 395). Then, the FTO glass is washed in the same manner as described above, followed by drying. Next, the FTO glass is coated with hydrogen hexachloroplatinate ($H_2PtCl_6$)/2-propanol solution and heat treated at 450° C. for 30 minutes.

(3) Manufacture of Sandwich Cell

First, Surlyn (Solaronix, SX1170-25 Hot Melt) cut into the shape of a rectangular strip is interposed between the working electrode and the counter electrode, and the two electrodes are laminated with each other by using a hot press. Then, an electrolyte is injected through the two small holes in the counter electrode, and the laminate is sealed with a Surlyn strip and a cover glass to provide a sandwich cell. The electrolyte is prepared from 0.1M LiI, 0.05M $I_2$, 0.6M 1-hexyl-2,3-dimethylimidazolium iodide and 0.5M 4-t-butylpyridine in 3-methoxypropionitrile as a solvent.

(4) Measurement of Photocurrent-Voltage

To the sandwich cell obtained as described above, light is irradiated with a Xe lamp (Oriel, 300W Xe arc lamp) equipped with AM 1.5 solar simulating filter. A photocurrent-voltage curve is obtained by using M236 source measure unit (SMU, Keithley). The voltage ranges from −0.8V to 0.2V and the light intensity is set to 100 $mW/cm^2$.

Characterization of Solar Cell Device Depending on Type of Dye

Solar cells are manufactured by using the different dyes according to Preparation Examples 1 to 10 in the same manner as described above and then characterized. Table 3 shows the particular type of the used dye, as well as the open-circuit voltage ($V_{oc}$), short-circuit current ($J_{sc}$), fill factor (FF) and photoelectric current conversion efficiency (%) measured from the resultant solar cell device. It is to be noted that the efficiencies described herein are not limited to the particular values exemplified hereinafter but vary with the device structure, size of titanium oxide, concentration and type of co-adsorbent, concentration and type of electrolyte, or the like.

TABLE 3

| Dye | $J_{sc}$ (mA/cm²) | Voc (V) | FF | Photoelectronic current conversion efficiency(%) |
|---|---|---|---|---|
| Prep. Ex. 1 | 9.99 | 0.71 | 0.56 | 3.95 |
| Prep. Ex. 2 | 15.99 | 0.64 | 0.53 | 5.43 |
| Prep. Ex. 3 | 14.30 | 0.63 | 0.55 | 4.92 |
| Prep. Ex. 4 | 4.42 | 0.62 | 0.52 | 1.42 |
| Prep. Ex. 5 | 7.07 | 0.72 | 0.60 | 3.05 |
| Prep. Ex. 6 | 5.98 | 0.67 | 0.67 | 2.68 |
| Prep. Ex. 7 | 9.66 | 0.73 | 0.59 | 4.18 |
| Prep. Ex. 8 | 2.64 | 0.56 | 0.68 | 1.00 |
| Prep. Ex. 9 | 6.48 | 0.56 | 0.65 | 2.35 |
| Prep. Ex. 10 | 4.51 | 0.55 | 0.63 | 1.57 |

INDUSTRIAL APPLICABILITY

The dye according to the present invention has a high light absorbance, and a dye-sensitised solar cell including the dye has excellent photoelectric current conversion efficiency.

What is claimed is:

1. A dye for a dye-sensitised solar cell, selected from compounds represented by Chemical Formula 3:

[Chemical Formula 3]

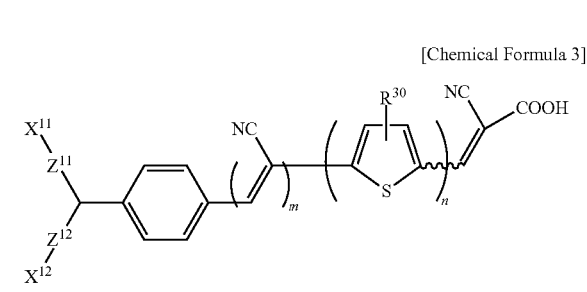

wherein
$X^{11}$ is selected from the following structures:

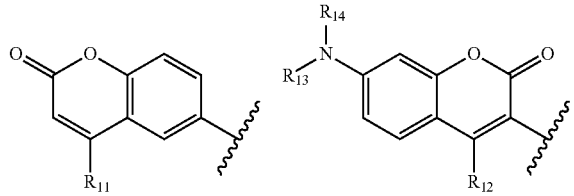
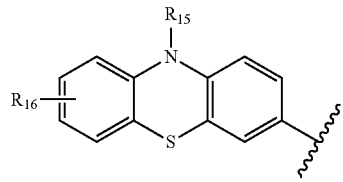
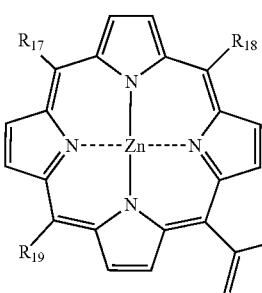

$X^{12}$ is selected from the following structures:

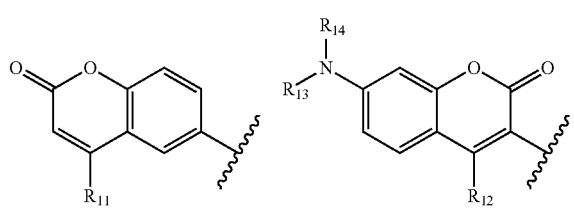

-continued

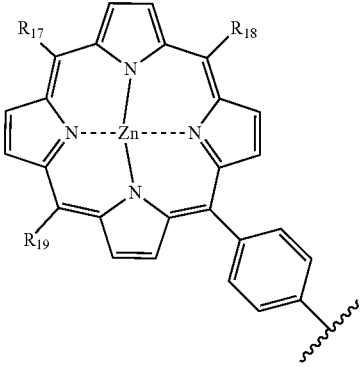
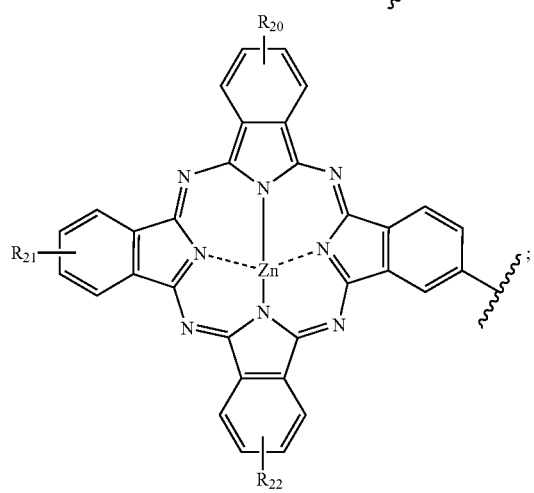

$Z^{11}$ and $Z^{12}$ independently represent

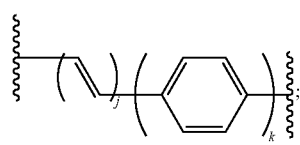

m is an integer from 0 to 2, and n is an integer from 0 to 4;
j is an integer from 0 to 2, and k is an integer from 0 to 4;
$R^{11}$ through $R^{22}$ and $R^{30}$ independently represent hydrogen, or are independently selected from (C1-C20)alkyl, (C1-C20)alkoxy, halogen atoms, amino, nitro and cyano (CN).

2. The dye for dye-sensitised solar cells according to claim 1, wherein the compound represented by Chemical Formula 3 is selected from the group consisting of compounds having the following structures:

101
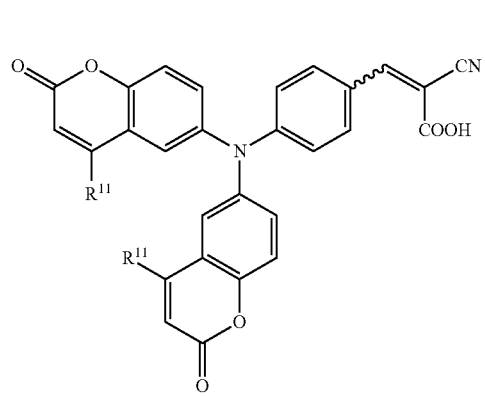
102
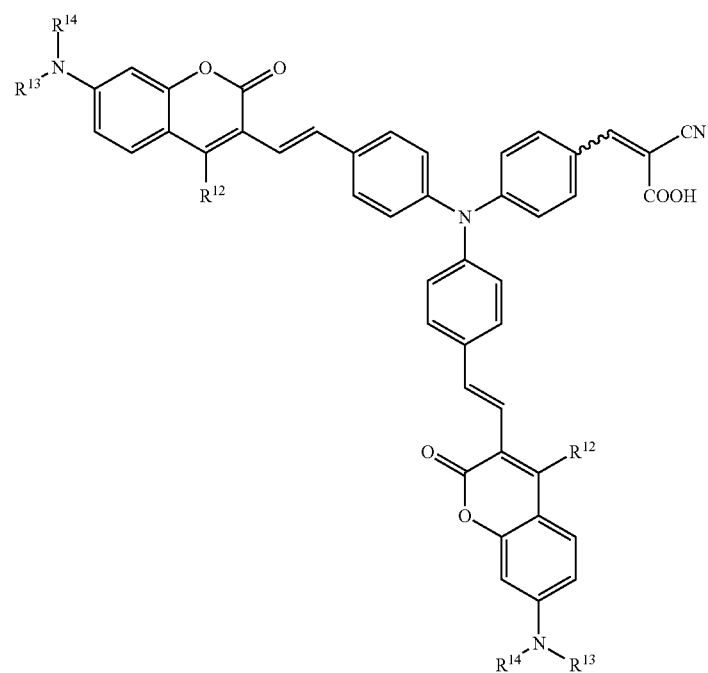
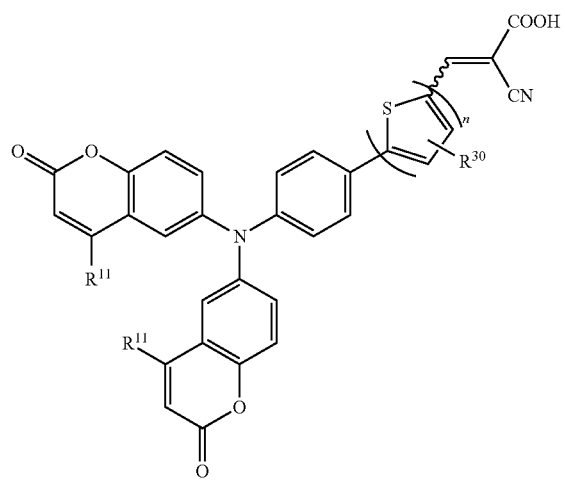

-continued
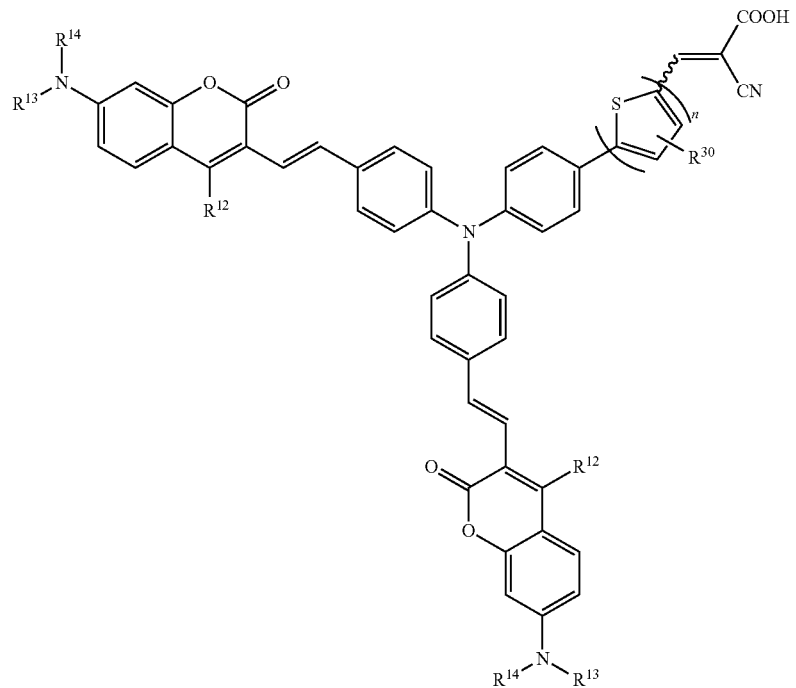
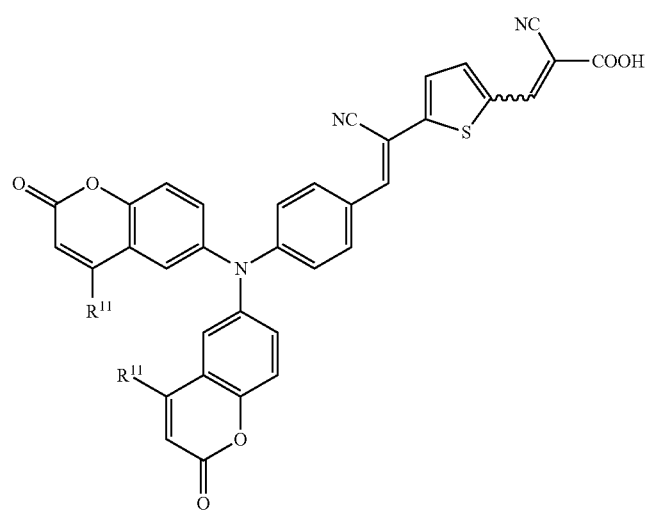

-continued
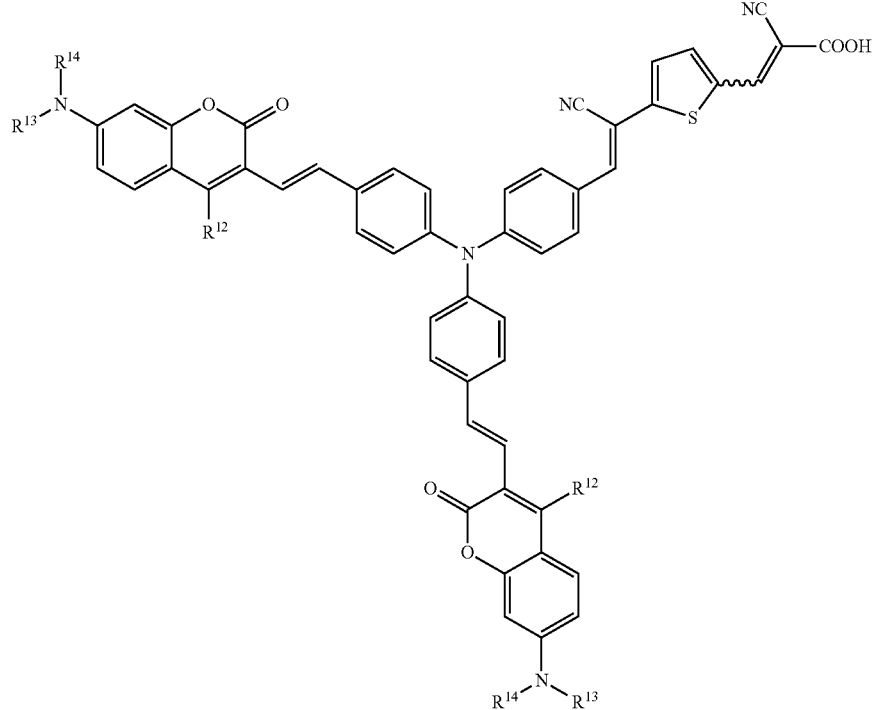
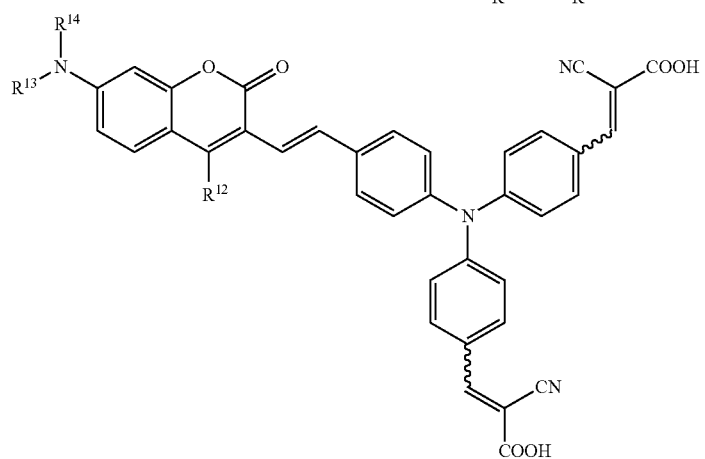
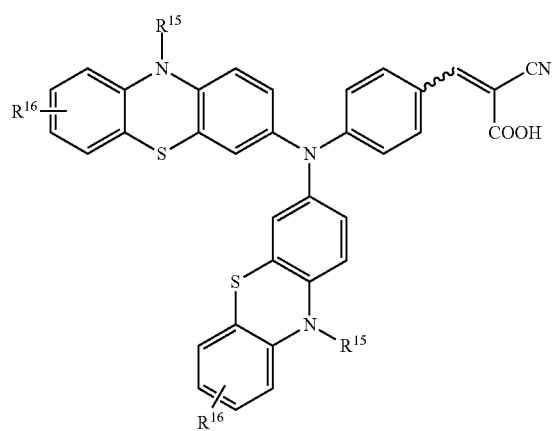

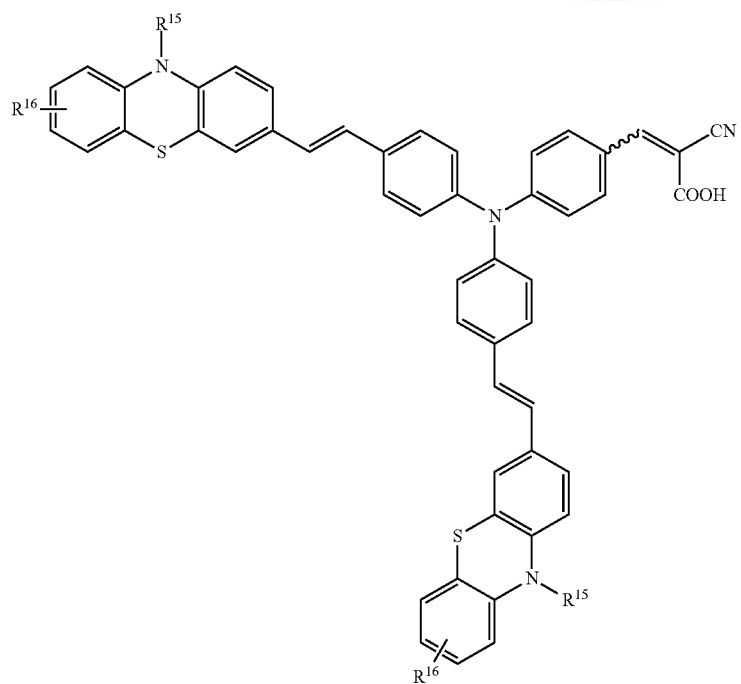
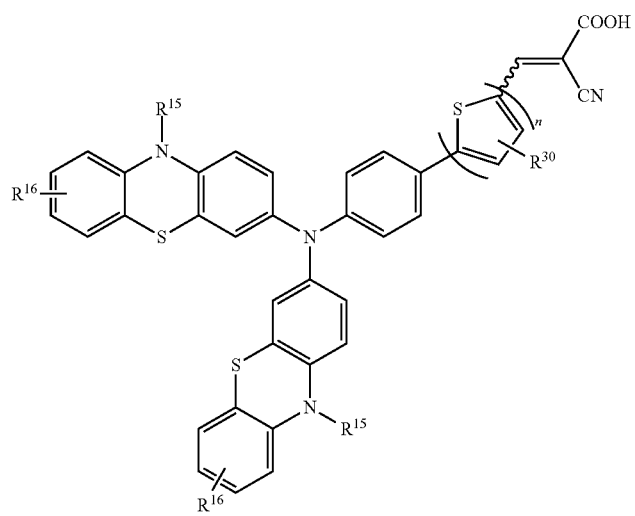

-continued
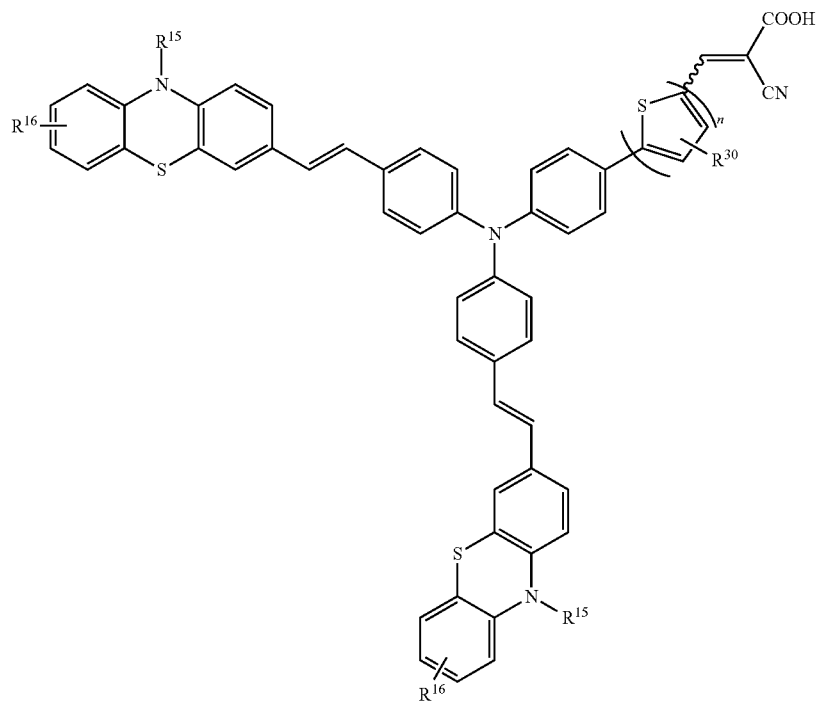
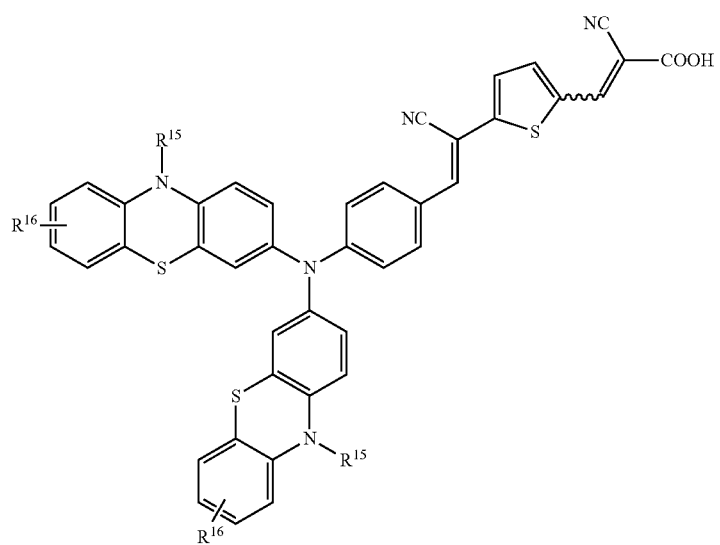

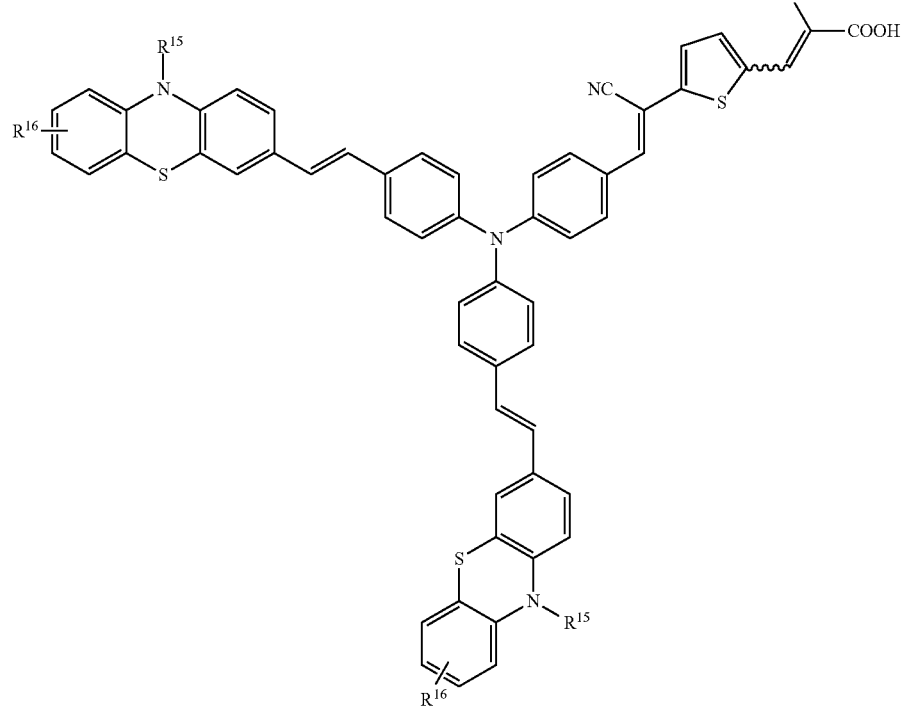
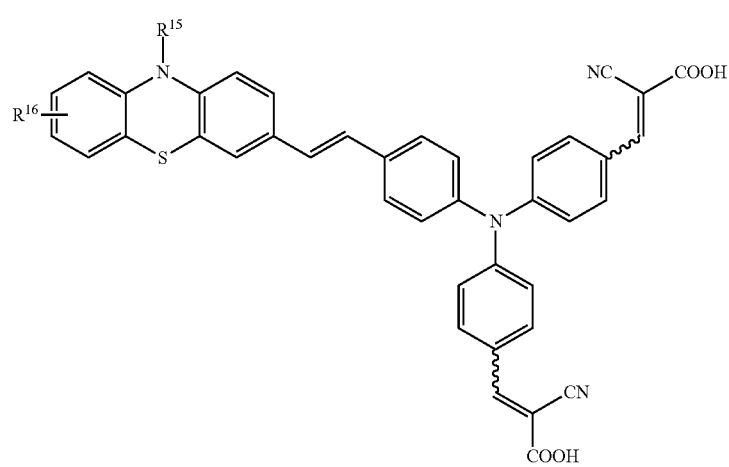

-continued
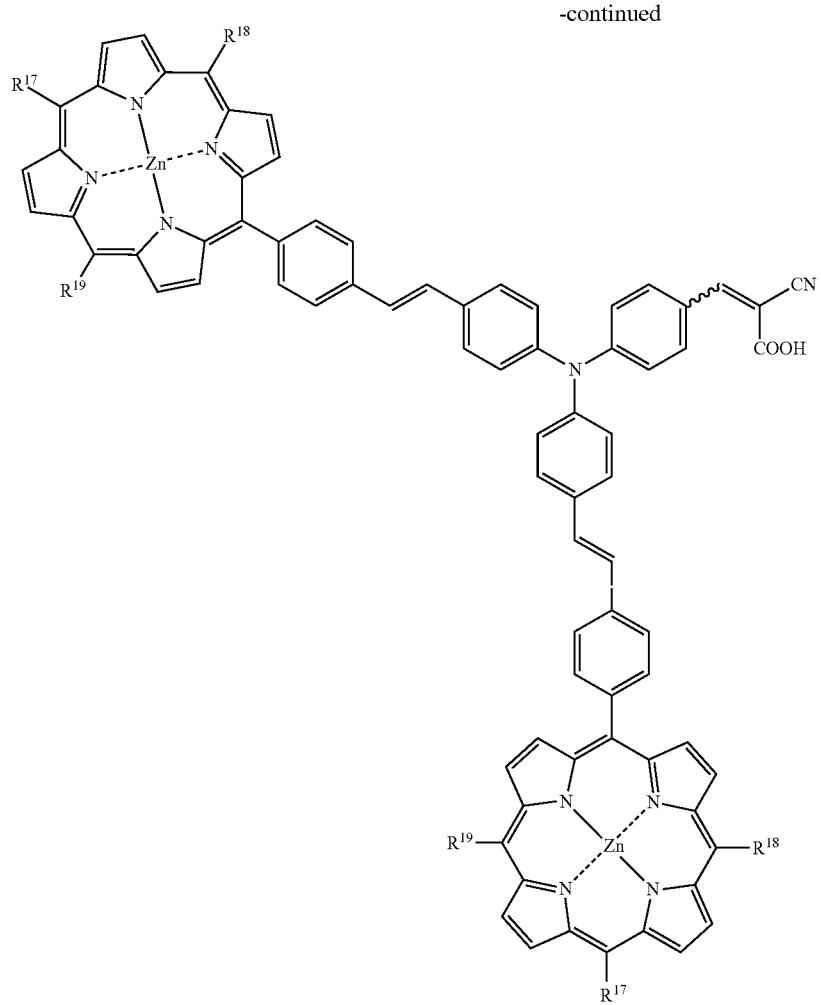
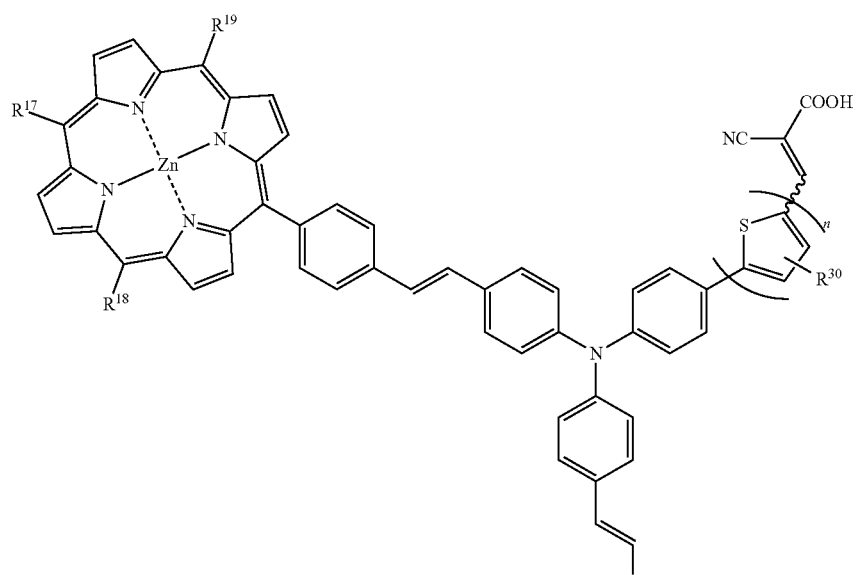

-continued
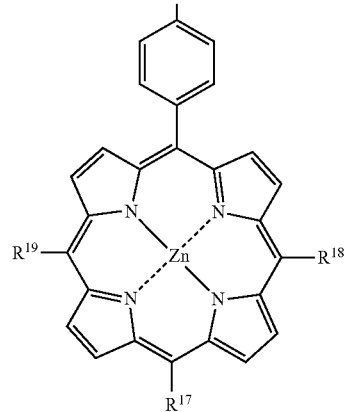
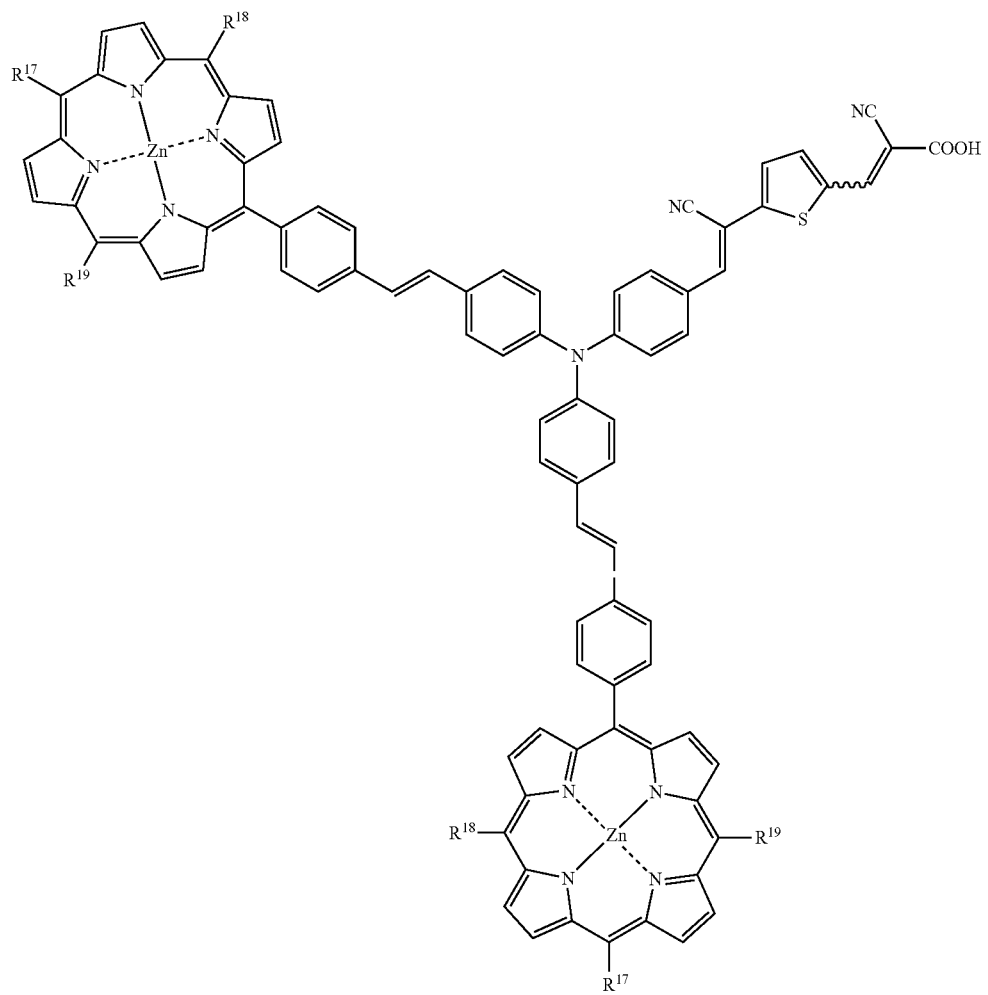

-continued
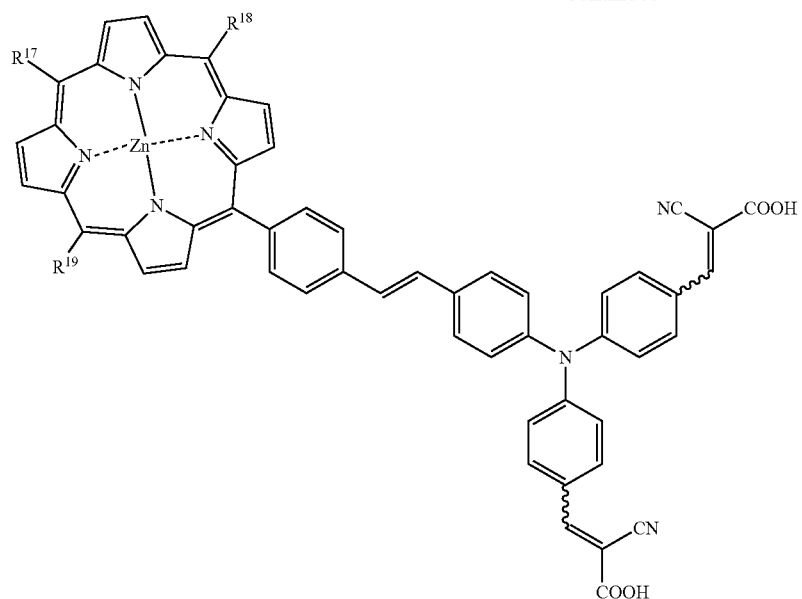
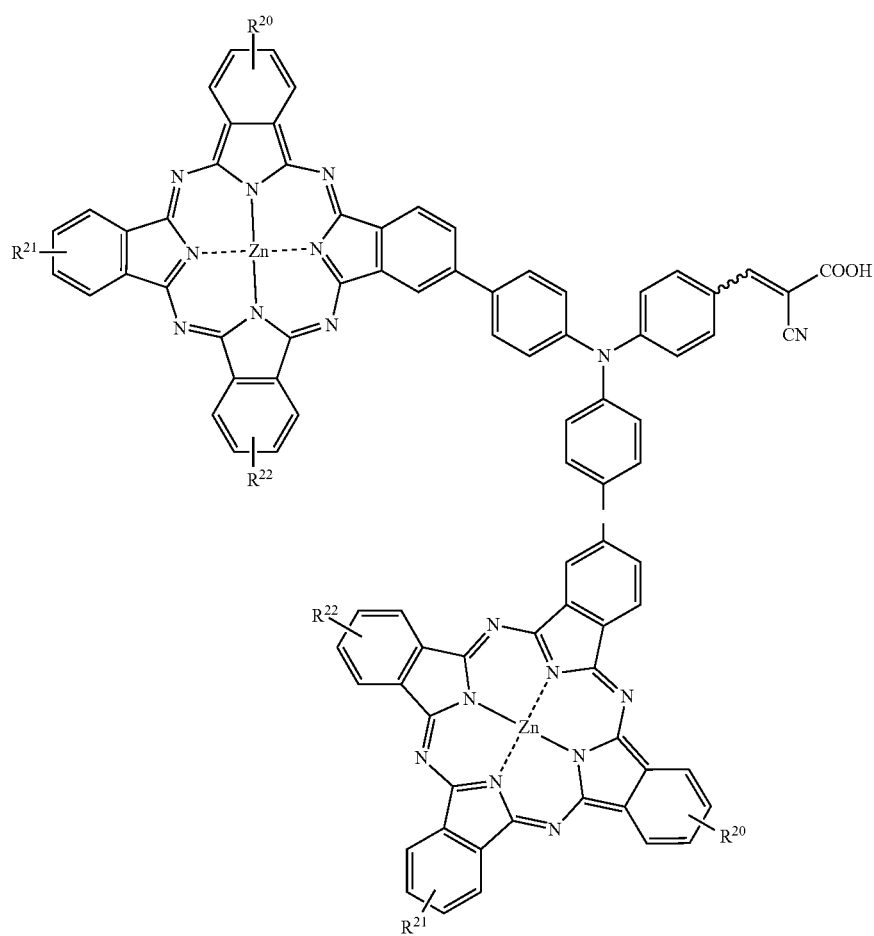

-continued
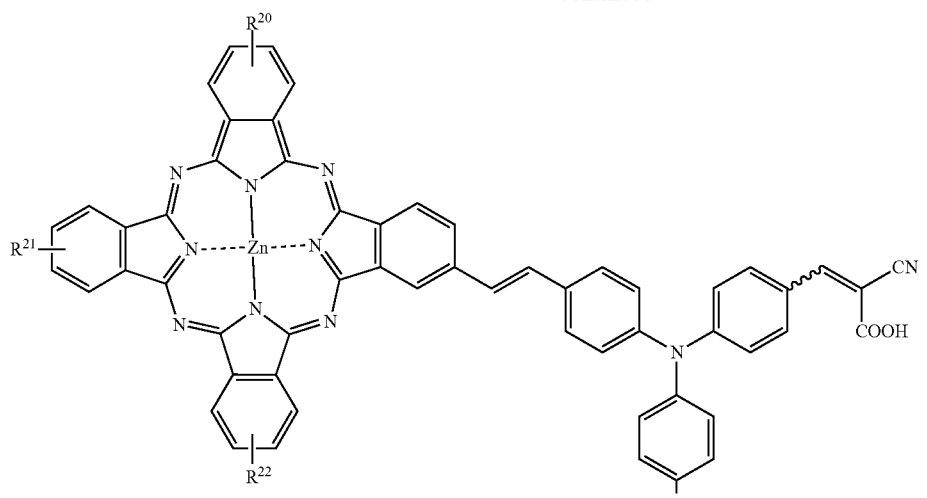
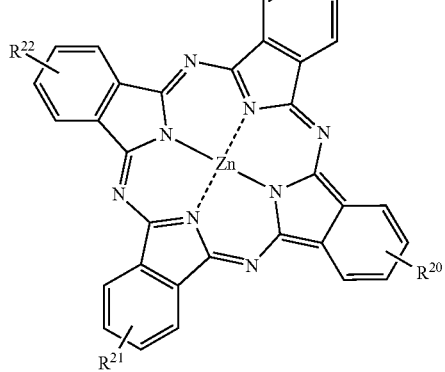
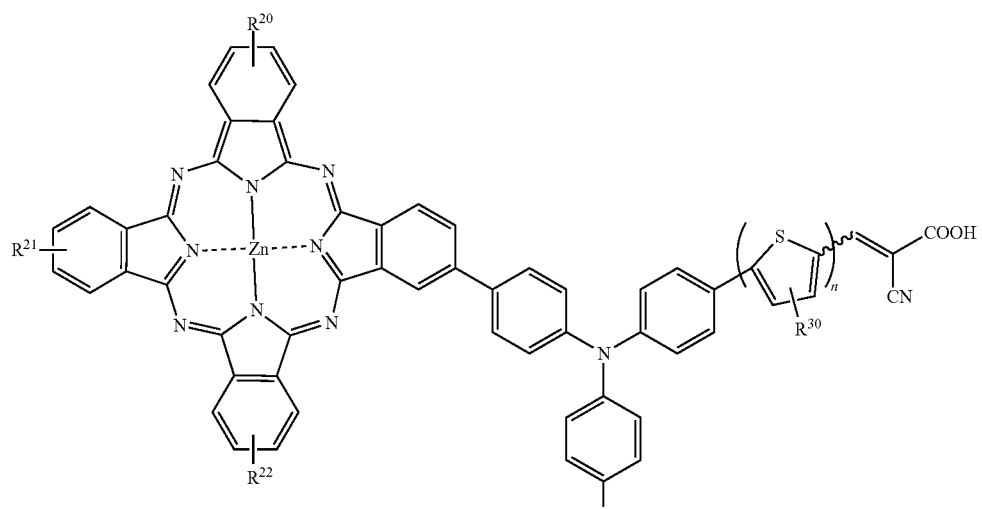

-continued
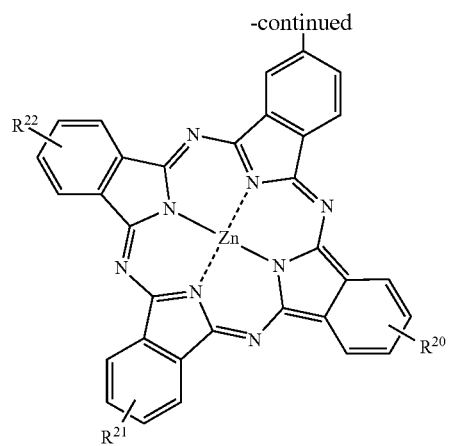
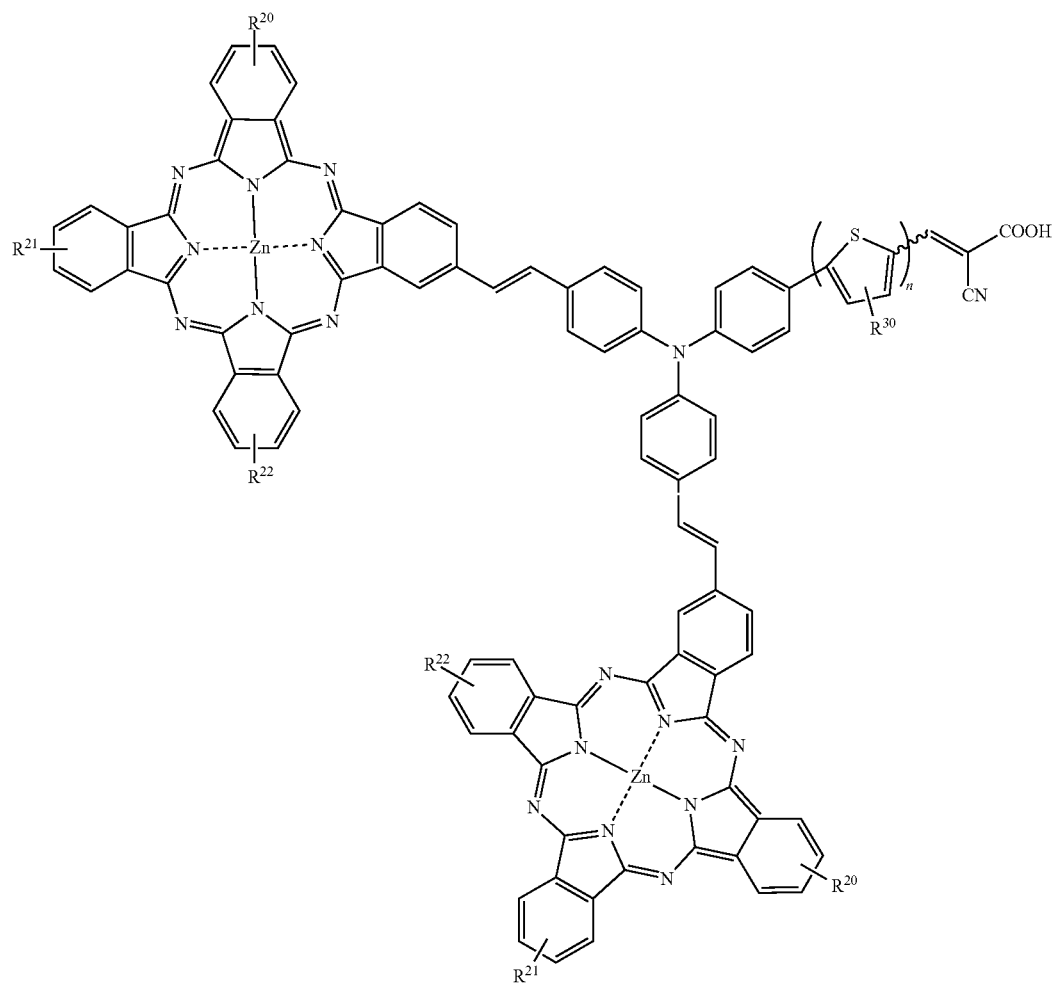

123
124
-continued
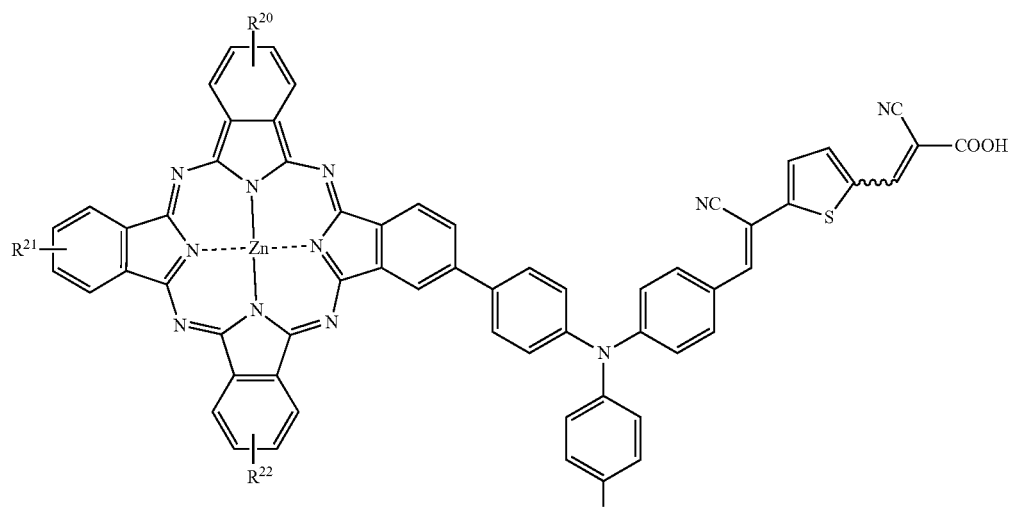
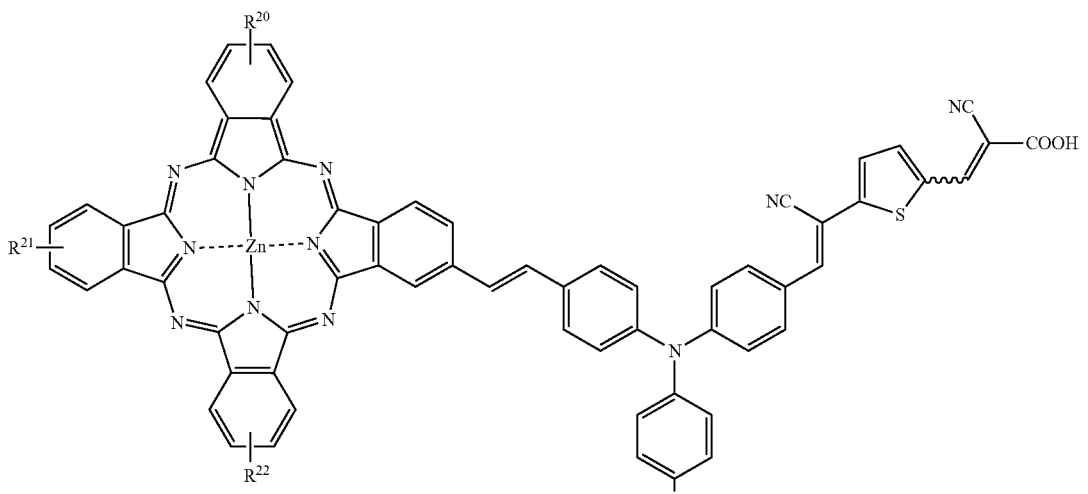

-continued
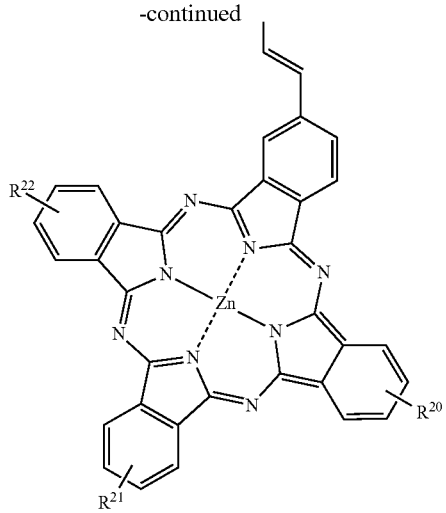
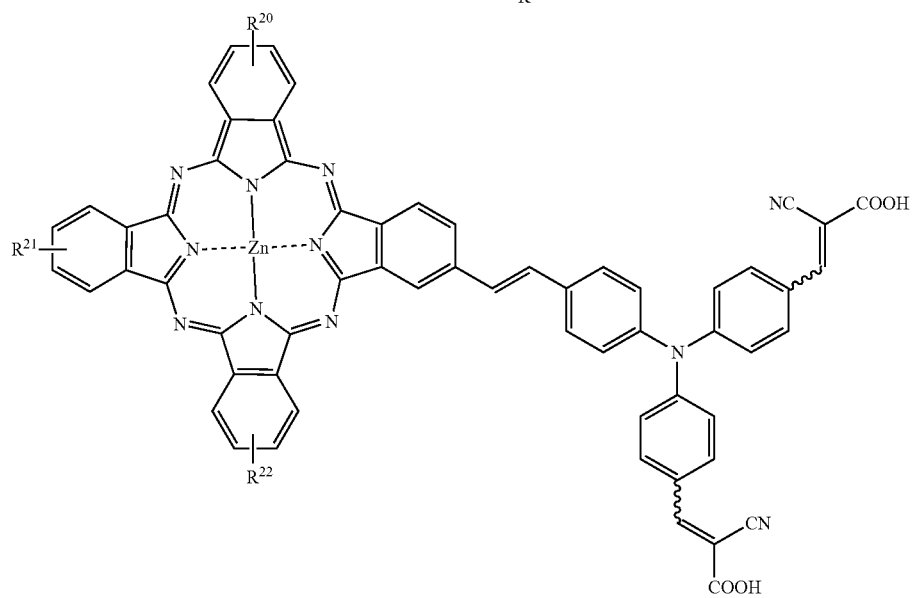
wherein
R$^{11}$ through R$^{22}$ and R$^{30}$ are independently selected from hydrogen and (C1-C20)alkyl; and n is an integer from 0 to 4.
3. A solar cell device comprising the dye as defined in claim 1 in a light-absorbing layer.
* * * * *

UNITED STATES PATENT AND TRADEMARK OFFICE
CERTIFICATE OF CORRECTION

PATENT NO.       : 8,629,269 B2                                                     Page 1 of 1
APPLICATION NO. : 12/866347
DATED            : January 14, 2014
INVENTOR(S)      : Kay et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 344 days.

Signed and Sealed this
Twenty-second Day of September, 2015

Michelle K. Lee
*Director of the United States Patent and Trademark Office*